US012358949B2

(12) United States Patent
Wehkamp et al.

(10) Patent No.: US 12,358,949 B2
(45) Date of Patent: Jul. 15, 2025

(54) DEFENSIN FRAGMENTS FOR USE IN THERAPY OR PROPHYLAXIS

(71) Applicant: Aesculus Bio ApS, Copenhagen N (DK)

(72) Inventors: Jan Wehkamp, Reutlingen (DE); Dirk Ehmann, Tübingen (DE)

(73) Assignee: Aesculus Bio ApS, Copenhagen N (DK)

( * ) Notice: Subject to any disclaimer, the term of this patent is extended or adjusted under 35 U.S.C. 154(b) by 935 days.

(21) Appl. No.: 17/420,155

(22) PCT Filed: Jan. 7, 2020

(86) PCT No.: PCT/EP2020/050186
§ 371 (c)(1),
(2) Date: Jul. 1, 2021

(87) PCT Pub. No.: WO2020/144166
PCT Pub. Date: Jul. 16, 2020

(65) Prior Publication Data
US 2022/0064217 A1  Mar. 3, 2022

(30) Foreign Application Priority Data

Jan. 7, 2019 (DE) .......................... 102019100230.3
Apr. 2, 2019 (DE) .......................... 102019108626.4

(51) Int. Cl.
*C07K 7/08* (2006.01)
*A61K 38/00* (2006.01)

(52) U.S. Cl.
CPC ............... *C07K 7/08* (2013.01); *A61K 38/00* (2013.01)

(58) Field of Classification Search
None
See application file for complete search history.

(56) References Cited

FOREIGN PATENT DOCUMENTS

| DE | 102014213654 A1 | 3/2016 |
|----|----|----|
| WO | 2003/101394 A2 | 12/2003 |
| WO | 2006/008162 A1 | 1/2006 |
| WO | 2007/081486 A2 | 7/2007 |
| WO | 2017/129195 A1 | 8/2017 |
| WO | WO2017/186250 A1 | 11/2017 |
| WO | 2018/108971 A2 | 6/2018 |

OTHER PUBLICATIONS

Hajdin et al., PLoS ONE 5(5): e10445 (Year: 2010).*
Mass General Brigham, downloaded from URL:<https://www.massgeneralbrigham.org/en/about/newsroom/articles/prevent-inflammatory-bowel-disease#:~:text=IBD%20prevention%20and%20risk%20factors,Genetics> (Year: 2024).*
Mayo clinic (downloaded from URL:<https://www.mayoclinic.org/diseases-conditions/asthma/symptoms-causes/syc-20369653#:~:text=Prevention,and%20managing%20an%20asthma%20attack>) (Year: 2024).*
Cleveland clinic (downloaded from URL:< https://my.clevelandclinic.org/health/diseases/12174-rosacea>) (Year: 2024).*
Leslie (Science Now, May 2012) (Year: 2012).*
Panos et al., Am J Med. Apr. 1990;88(4):396-404 (Year: 1990).*
Costello et al. (Pancreat Disord Ther; Suppl 4; doi:10.4172/2165-7092.S4-002) (Year: 2013).*
American optometric association (downloaded from URL:< https://www.aoa.org/healthy-eyes/eye-and-vision-conditions/anterior-uveitis?sso=y >) (Year: 2024).*
Compass Oncology (downloaded from URL:< A Simple Test Could Reveal if You're at High Risk for Colon Cancer>; 2024) (Year: 2024).*
Brinckerhoff et al., Terminal modifications inhibit proteolytic degradation of an immunogenic mart-1-27-35 peptide: implications for peptide vaccines, Int. J. Cancer, 83: 326-334, 1999.
Chu et al., Human a-defensin 6 promotes mucosal innate immunity through self-assembled peptide nanonets, Science, 337(6093): 477-481, Jul. 27, 2012.
Ericksen et al., Antibacterial Activity and Specificity of the Six Human α-Defensins, Antimicrobial Agents and Chemotherapy, p. 269-275, Jan. 2005.
Hong et al., Effect of D-Amino Acid Substitution on the Stability, the Secondary Structure, and the Activity of Membrane-Active Peptide, Biochemical Pharmacology, 58: 1775-1780, 1999.
Lehrer et al. α-Defensins in human innate immunity Immunological Reviews, 245: 84-112, 2012.
Mathew et al., Antimicrobial activity of human a-defensin 5 and its linear analogs: N-terminal fatty acylation results in enhanced antimicrobial activity of the linear analogs; Peptides, 71: 128-140, 2015.
Peschel et al., *Staphylococcal* resistance to antimicrobial peptides of mammalian and bacterial origin, Peptides, 22 1651-1659, 2001.
Rajabi et al., The Conserved Salt Bridge in Human α-Defensin 5 is required for its precursor processing and Proteolytic Stability, The Journal of Biological Chemistry, 283(31): 21509-21518, 2008.
Rajabi et al., Functional Determinants of Human enteric α-Defensin HD5, The Journal of Biological Chemistry, 287 (26): 21615-21627, 2012.
Schroeder et al., Reduction of disulphide bonds unmasks potent antimicrobial activity of human β-defensin 1, Nature, 469: 419-423, 2011.

(Continued)

*Primary Examiner* — Sergio Coffa
(74) *Attorney, Agent, or Firm* — Weston R. Gould; Dinsmore & Shohl LLP

(57) ABSTRACT

The present invention relates to new peptides derived from HD-5 or HNP-4 having antimicrobial activity for use in modulating the microbiome of intestines, the lungs, the skin, the mouth, the eye, the ear, the vagina or other bodily surfaces and/or for use as an antimicrobial agent in a human or other mammals, as well as to medicaments containing these peptides.

13 Claims, 49 Drawing Sheets
Specification includes a Sequence Listing.

(56) References Cited

OTHER PUBLICATIONS

Schroeder et al., Waking the wimp: Redox-modulation activates human beta-defensin 1, Gut Microbes, 2(4), 262-266, 2011.
Szyk et al., Crystal structures of human a-defensins HNP4, HD5 and HD6. Protein Science, 15: 2749-2760, 2006.
Wanniarachchi et al., Human Defensin 5 Disulfide Array Mutants: Disulfide Bond Deletion Attenuates Antibacterial Activity against *Staphylococcus aureus*. Biochemistry, 50(37): 8005-8017, Sep. 20, 2011.
Wendler et al., Bacterial Periplasmic Oxidoreductases Control the Activity of Oxidized Human Antimicrobial β- Defensin 1, Infection and Immunity, 86(4): e00875-17, 2018.
Examination Report No. 1 for Australian Patent Application No. 2020207527, dated Jan. 16, 2025, 4 pages.

\* cited by examiner

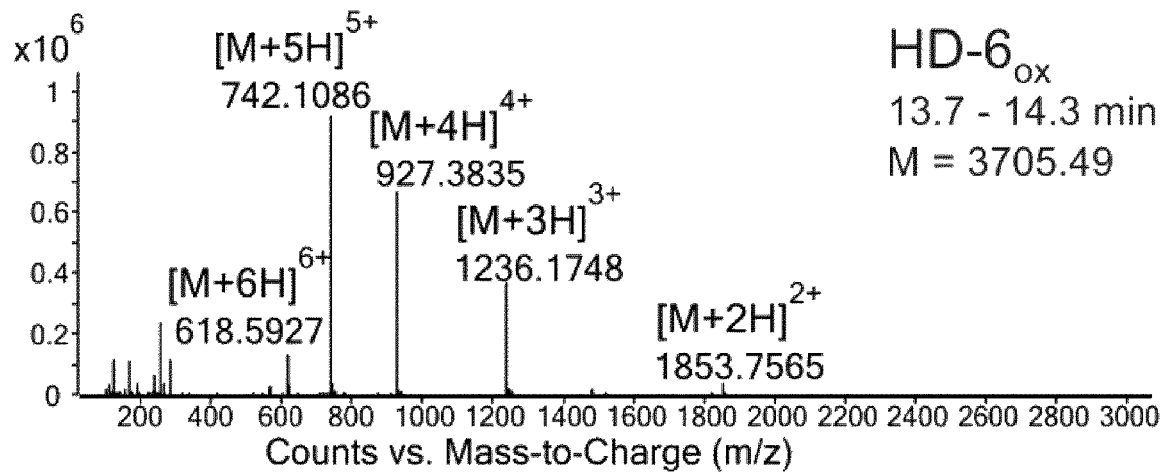
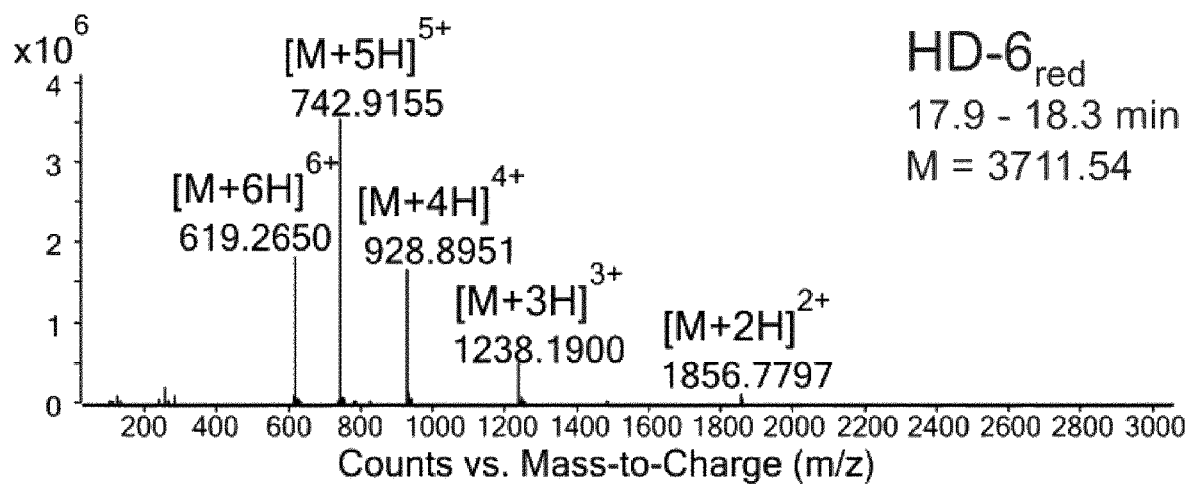
Fig. 1A Contd.

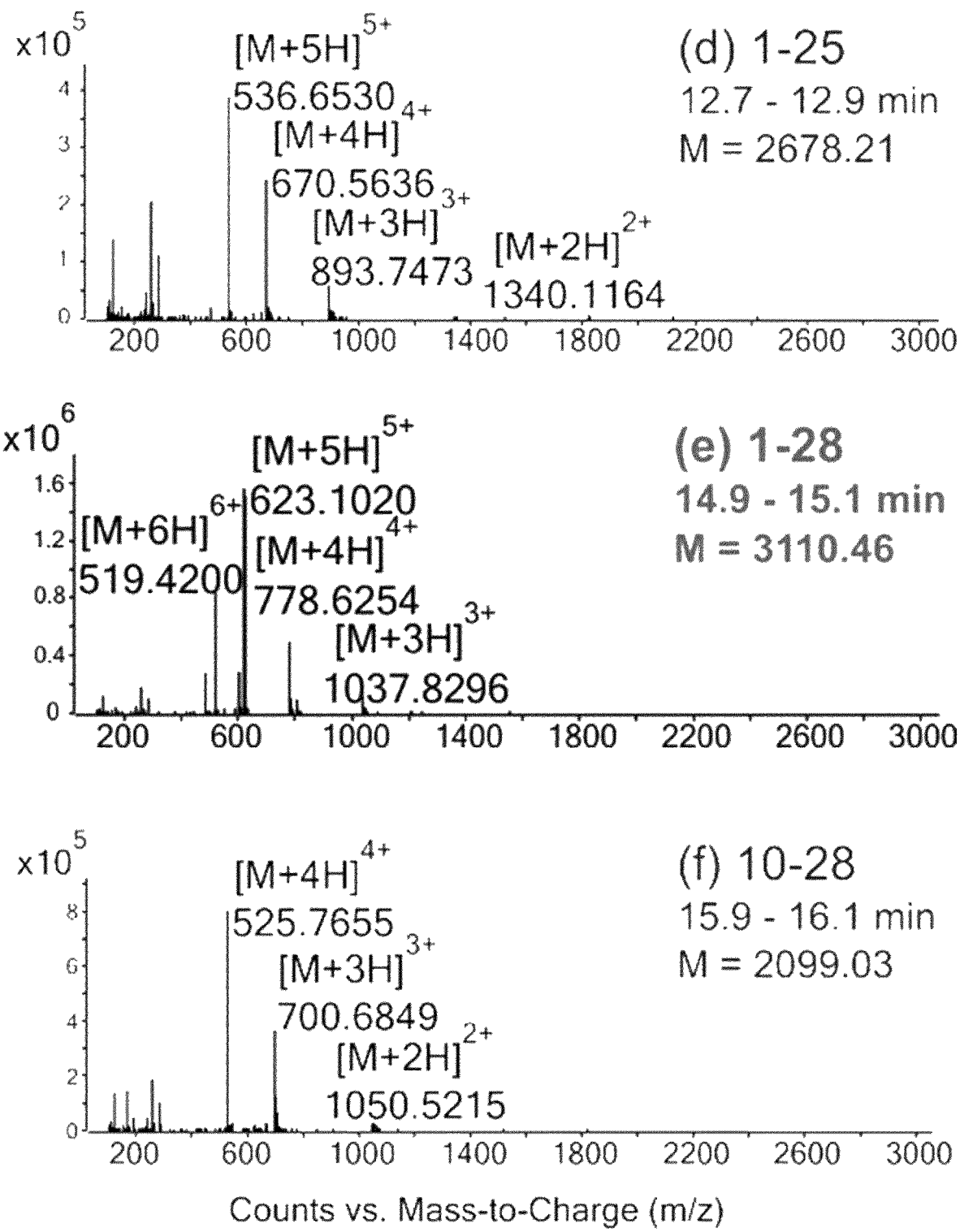
Fig. 2B Contd.

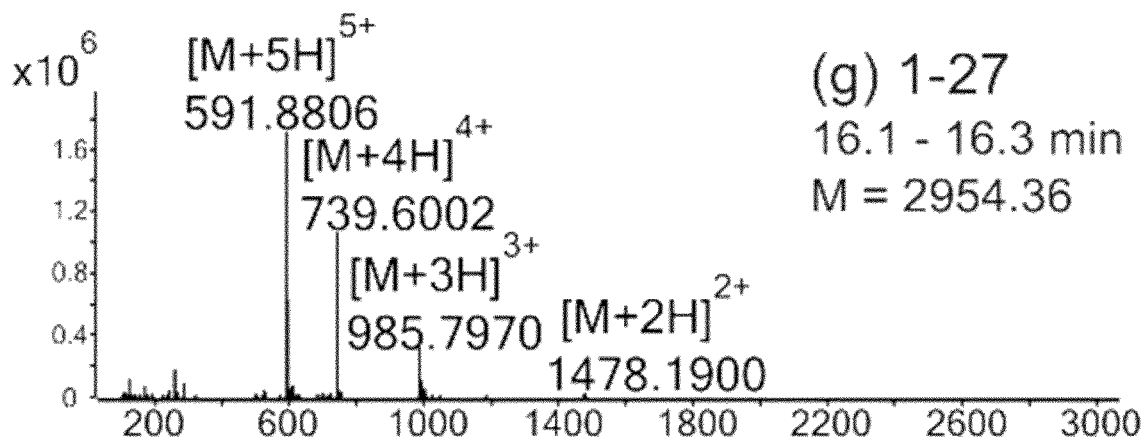
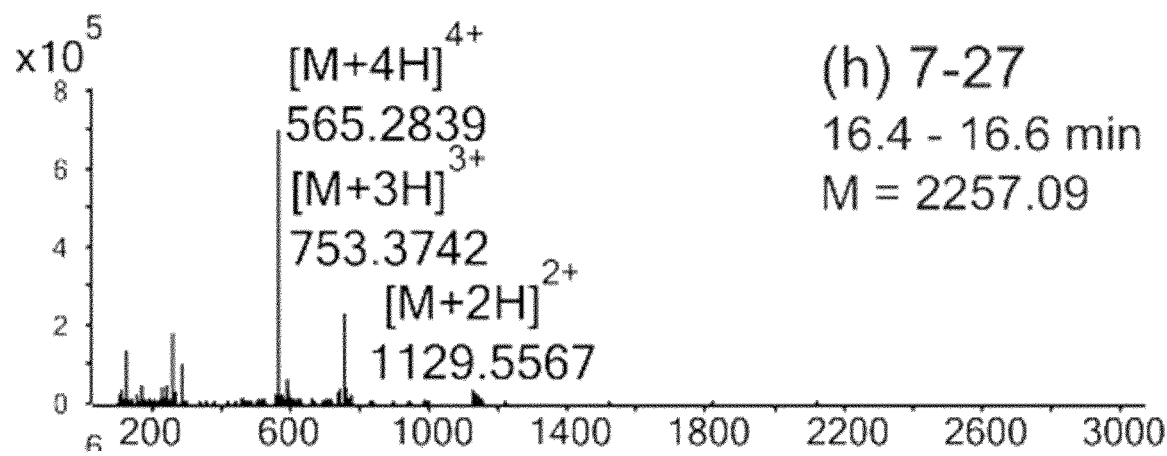
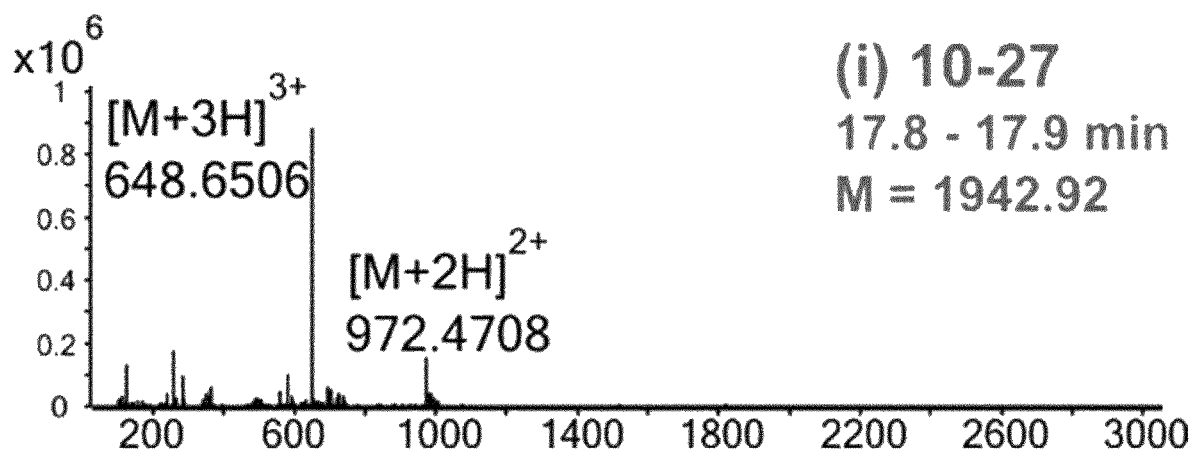
Fig. 2B Contd.

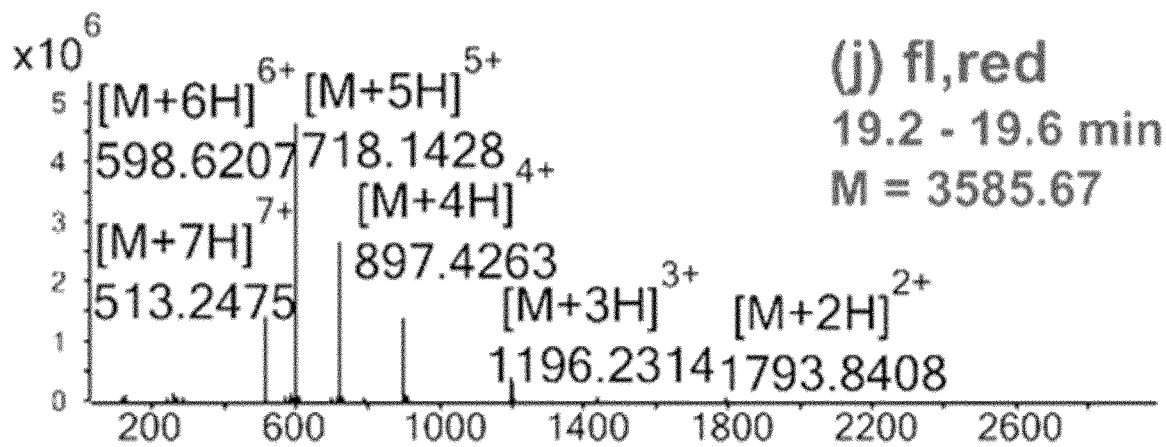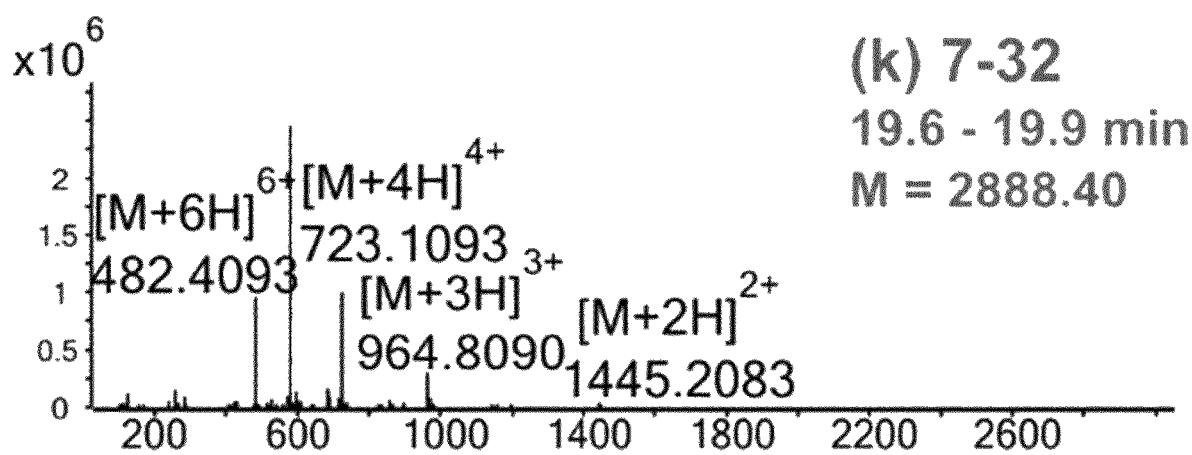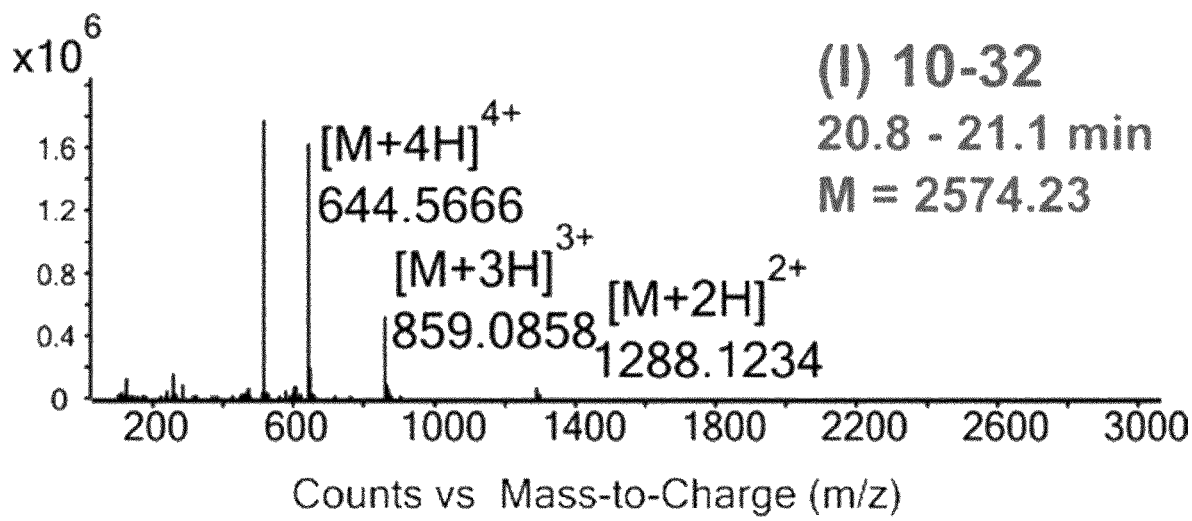
Fig. 2B Contd.

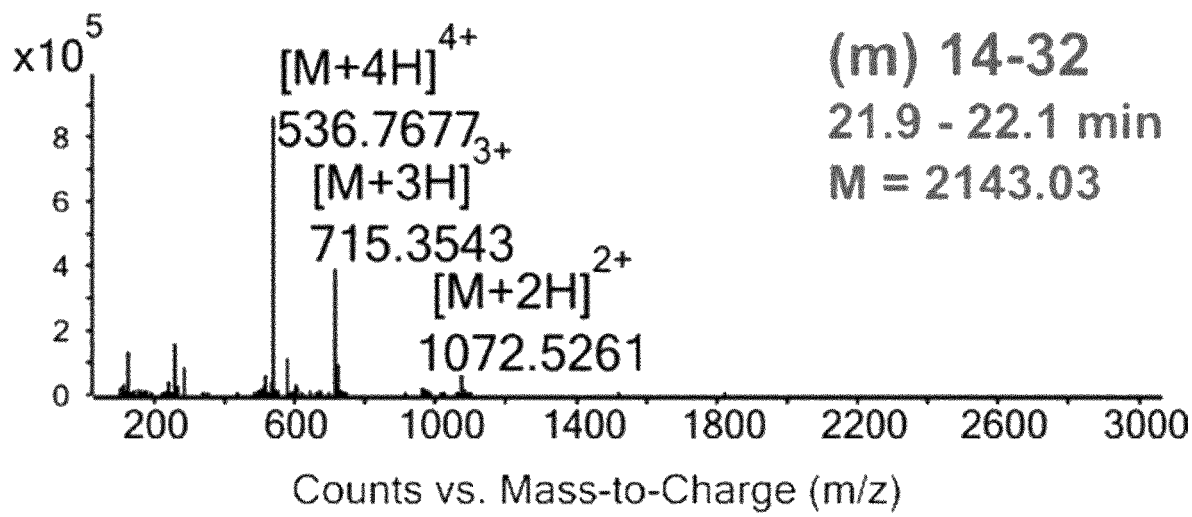
Fig. 2B Contd.
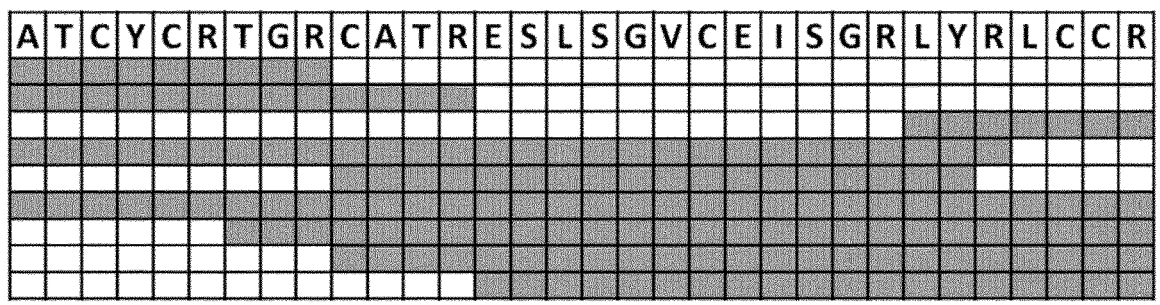
Fig. 2C

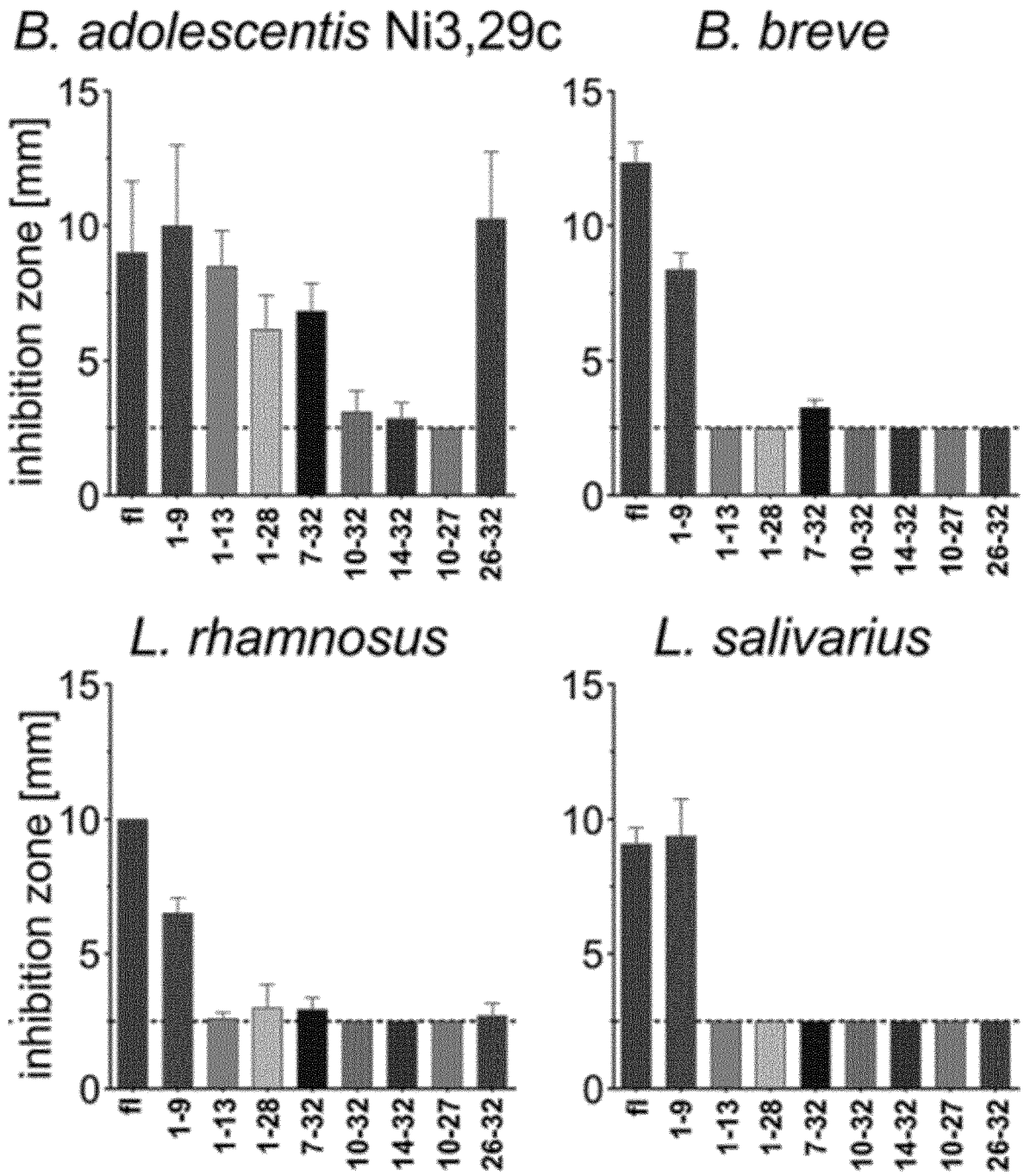
Fig. 3B Contd.

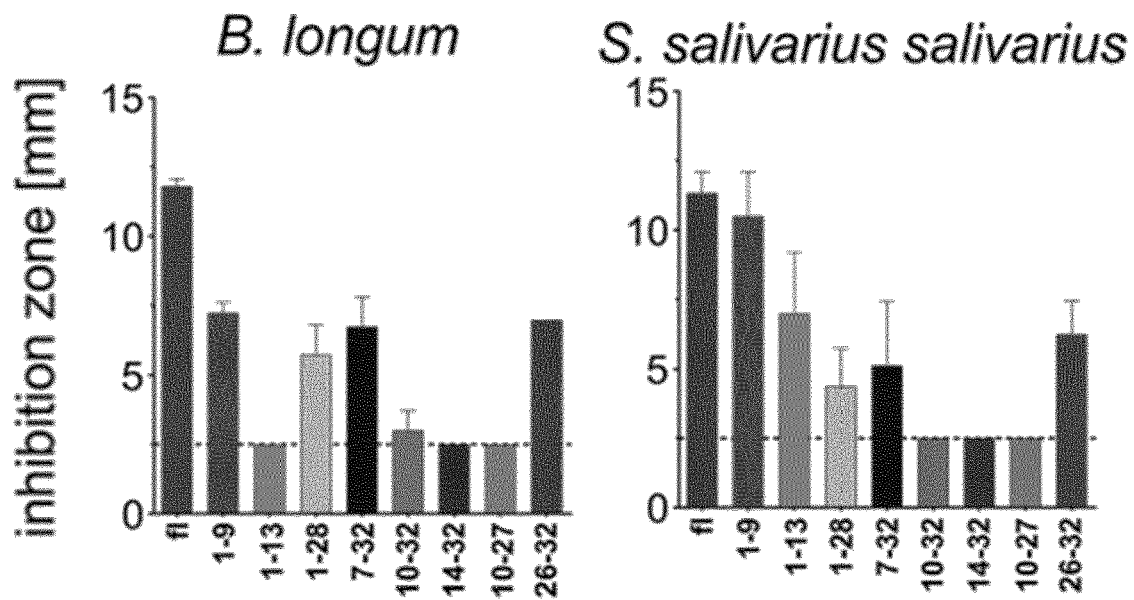
Fig. 3B Contd.
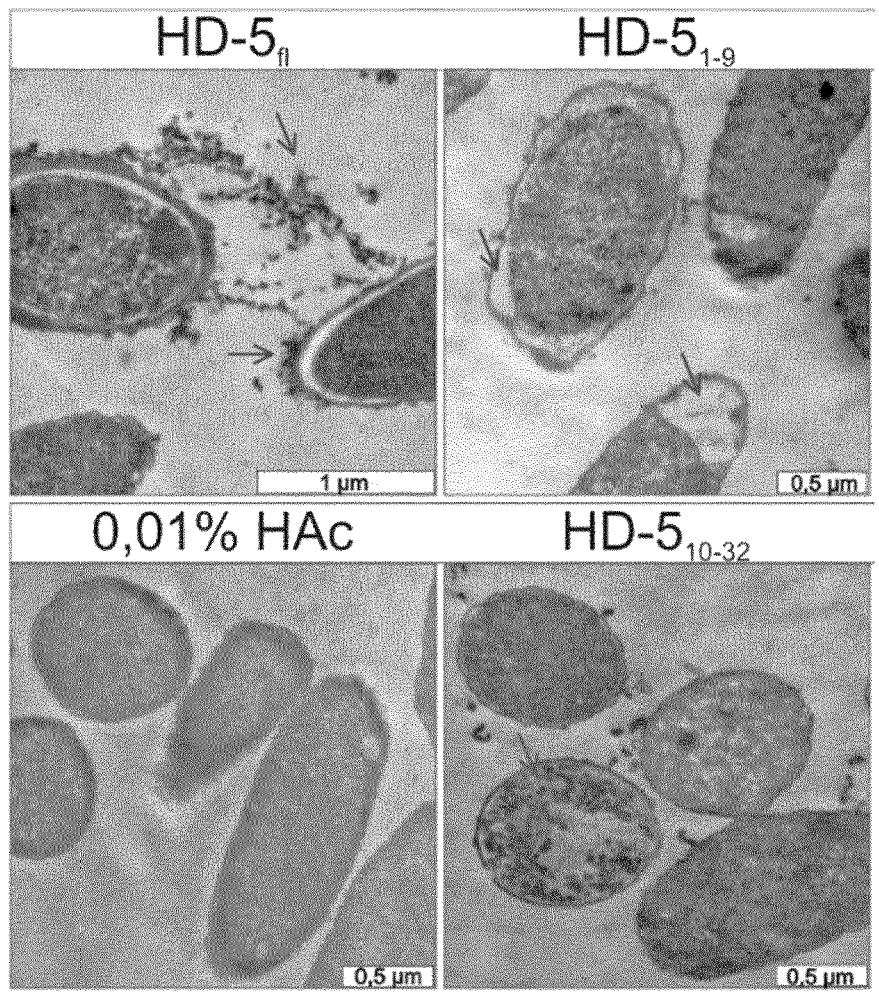
Fig. 3C

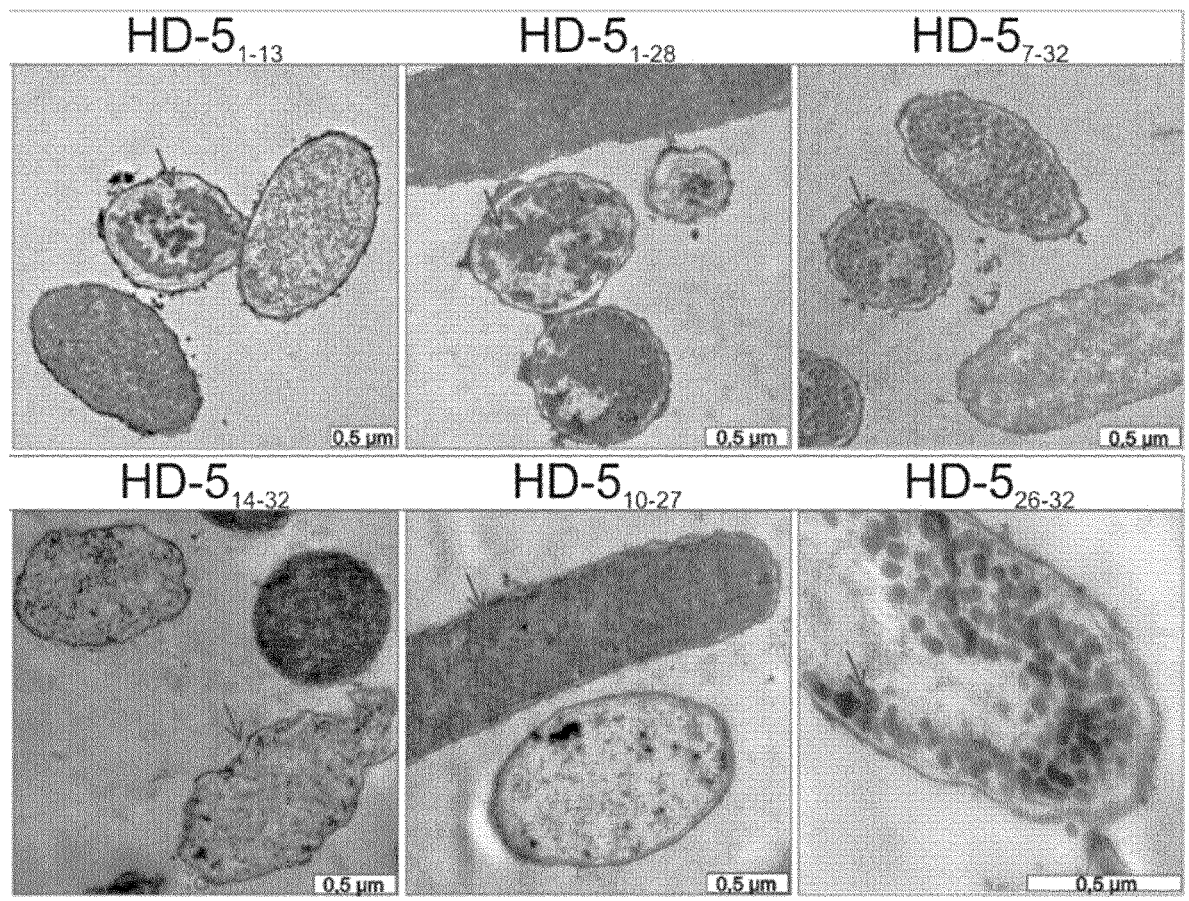
Fig. 3C Contd.

Fig. 4A

| pathogenic bacteria | fl | 1-9 | 1-13 | 1-28 | 7-32 | 10-32 | 14-32 | 10-27 | 26-32 |
|---|---|---|---|---|---|---|---|---|---|
| | | | | | HD-5 | | | | |
| A. baumannii 4-MRGN | | | | | | | | | |
| K. pneumoniae 3-MRGN | | | | | | | | | |
| P. aeruginosa ATCC 27853 | | | | | | | | | |
| E. faecium 475747 | | | | | | | | | |
| S. aureus USA300 | | | | | | | | | | high activity | low activity | no activity

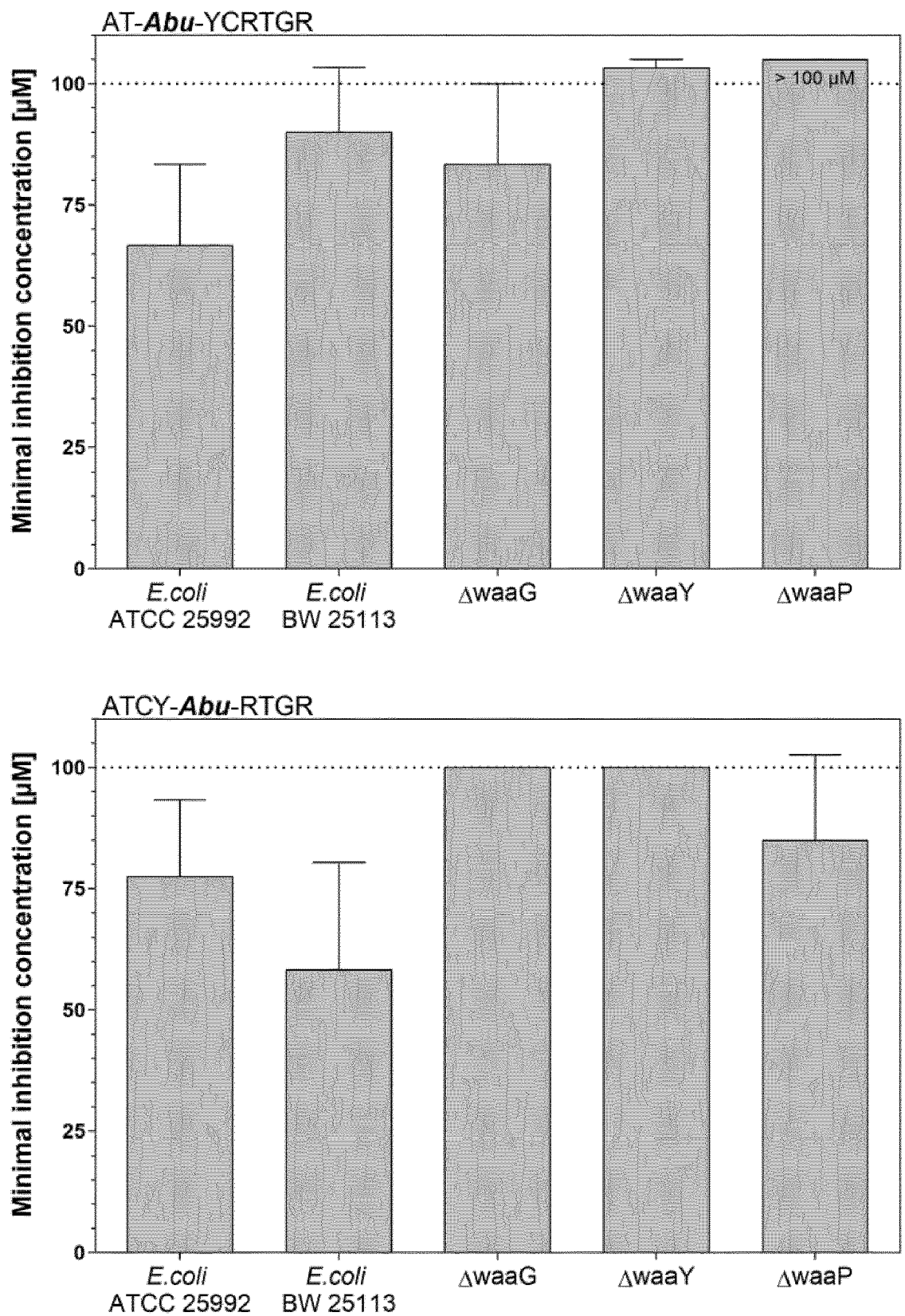
Fig. 5A Contd.

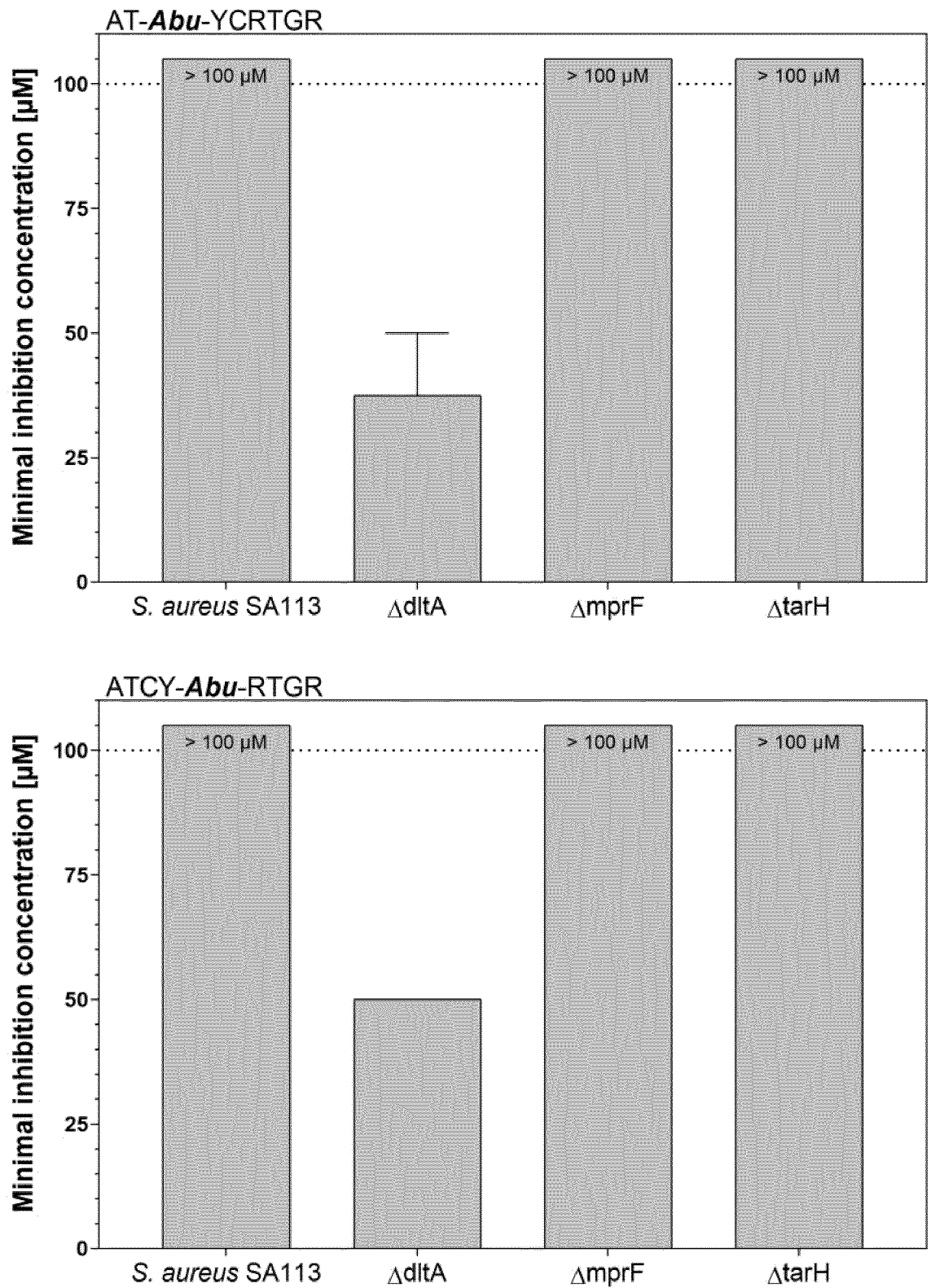
Fig. 5B Contd.

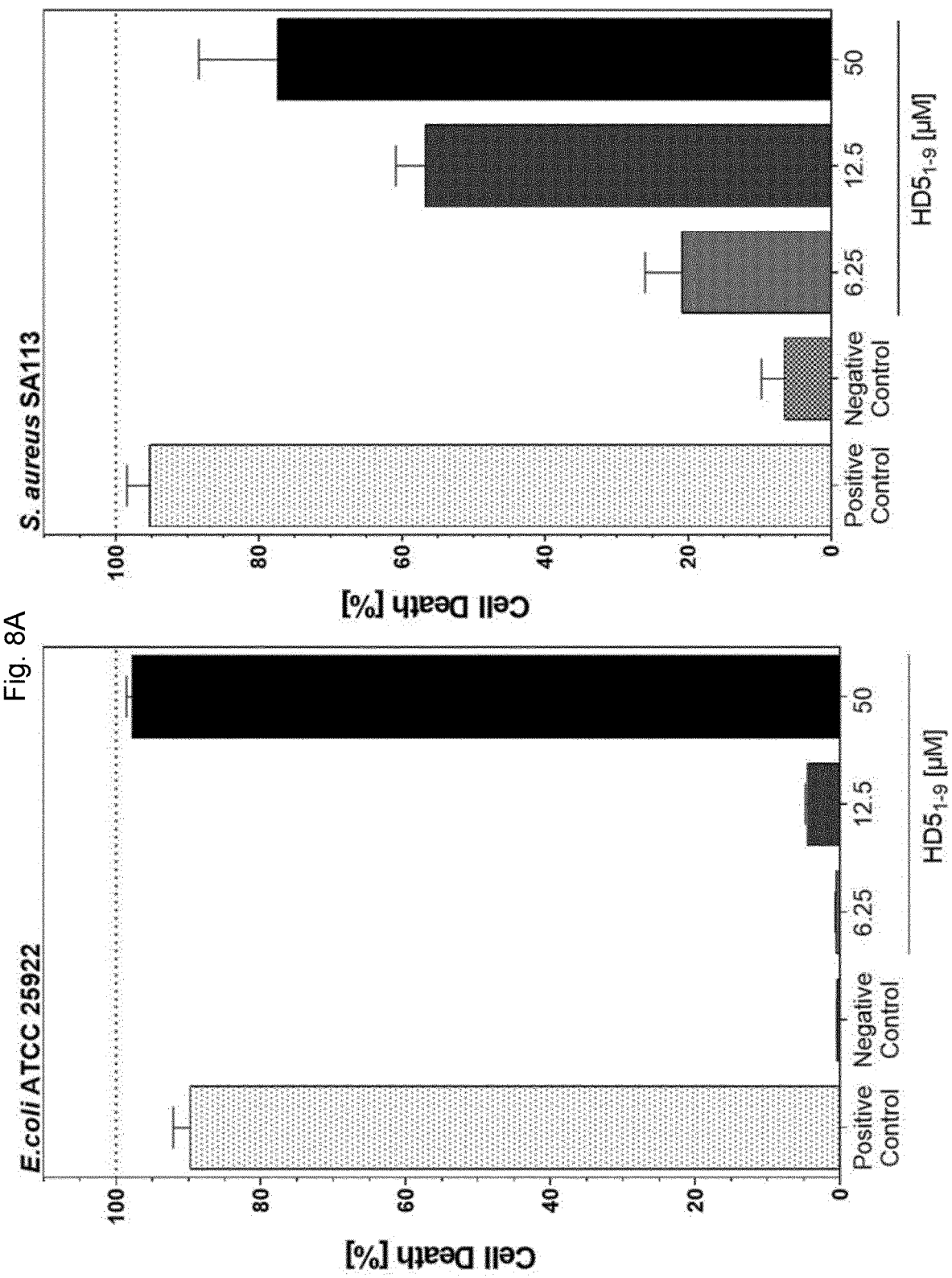

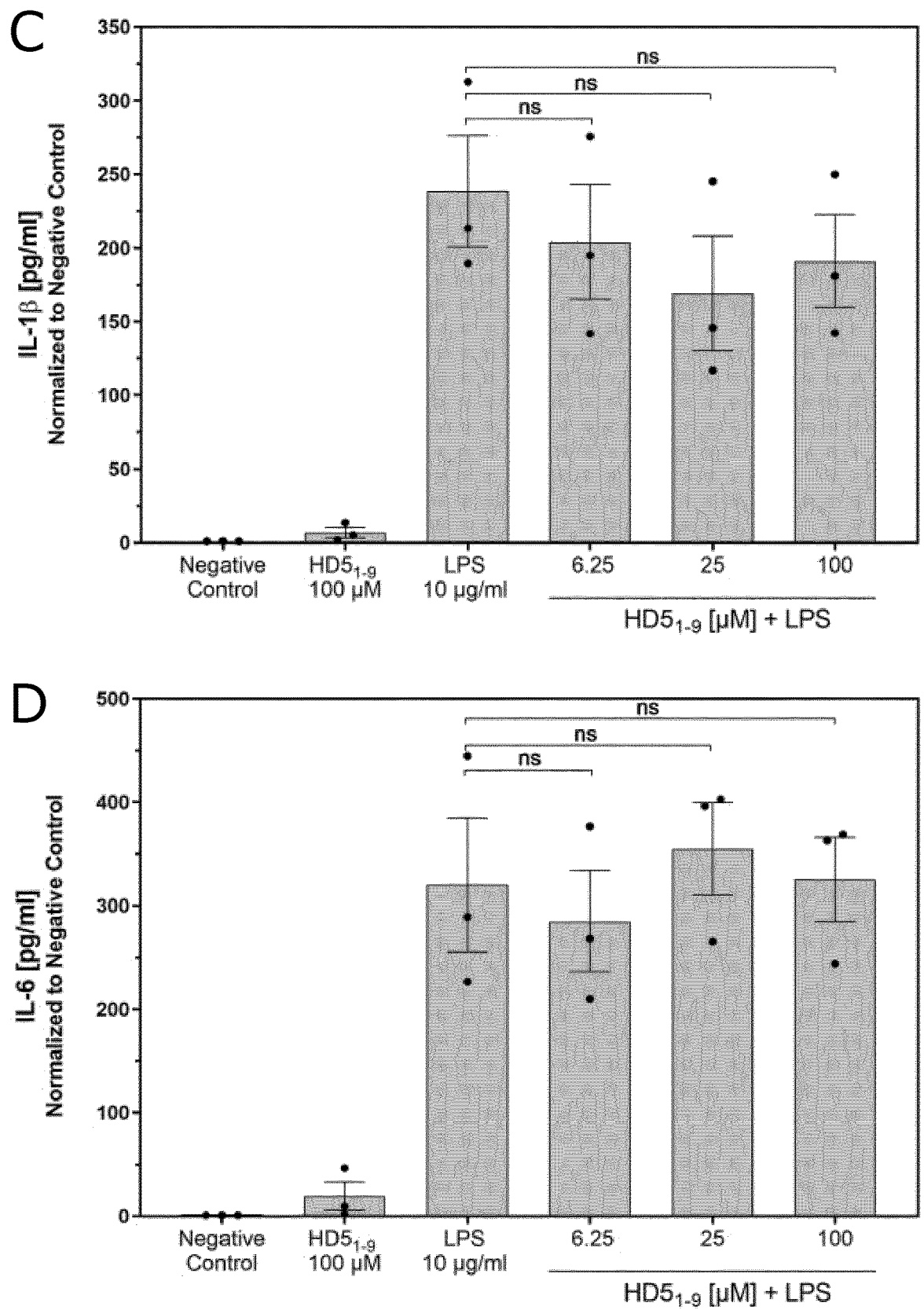
Fig. 10 Contd.

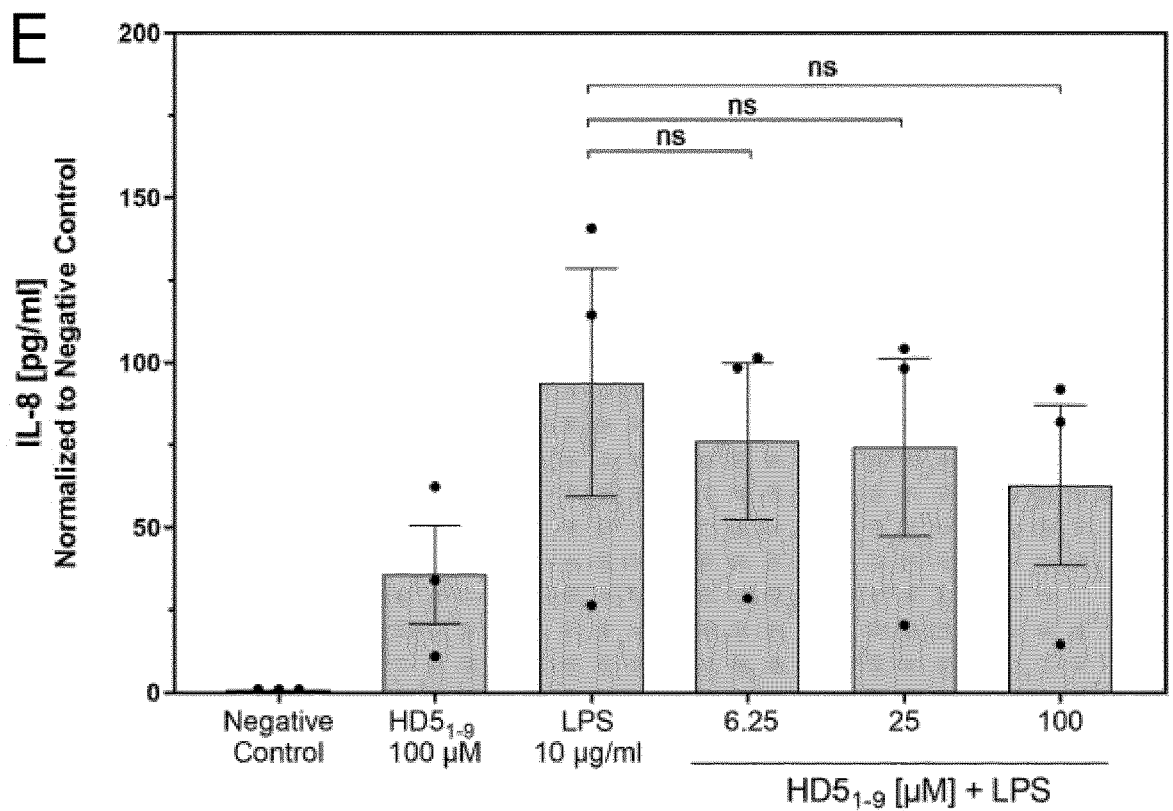
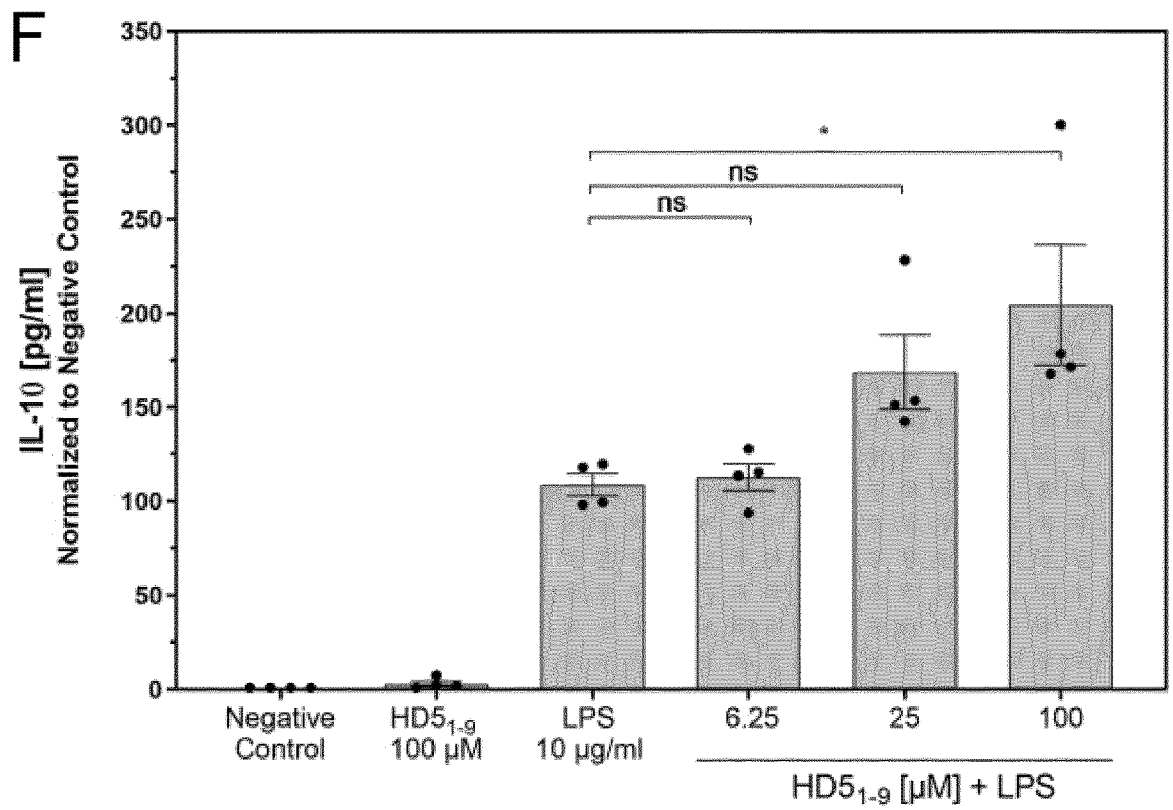
Fig. 10 Contd.

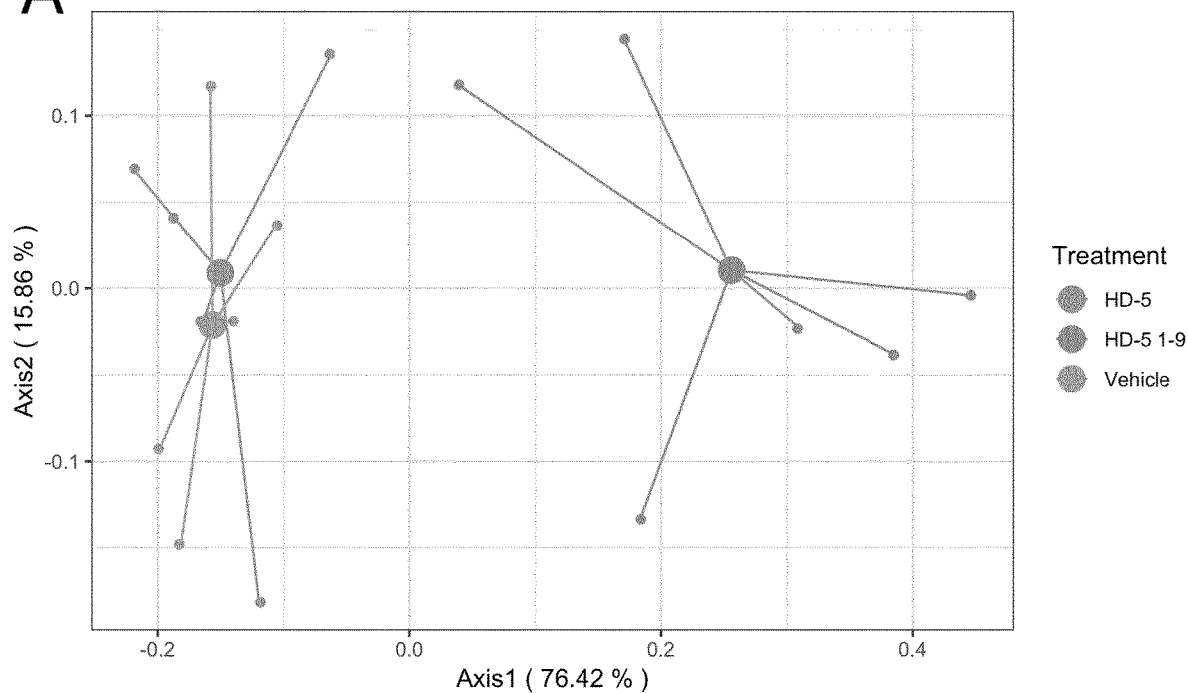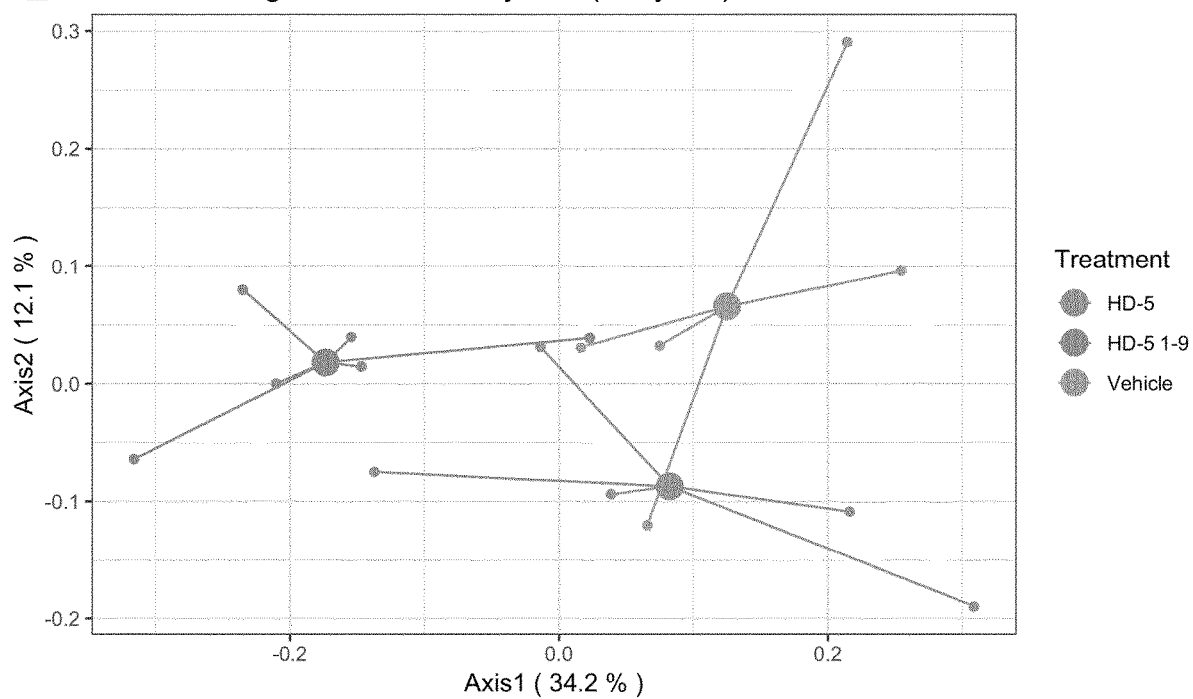
Fig. 14

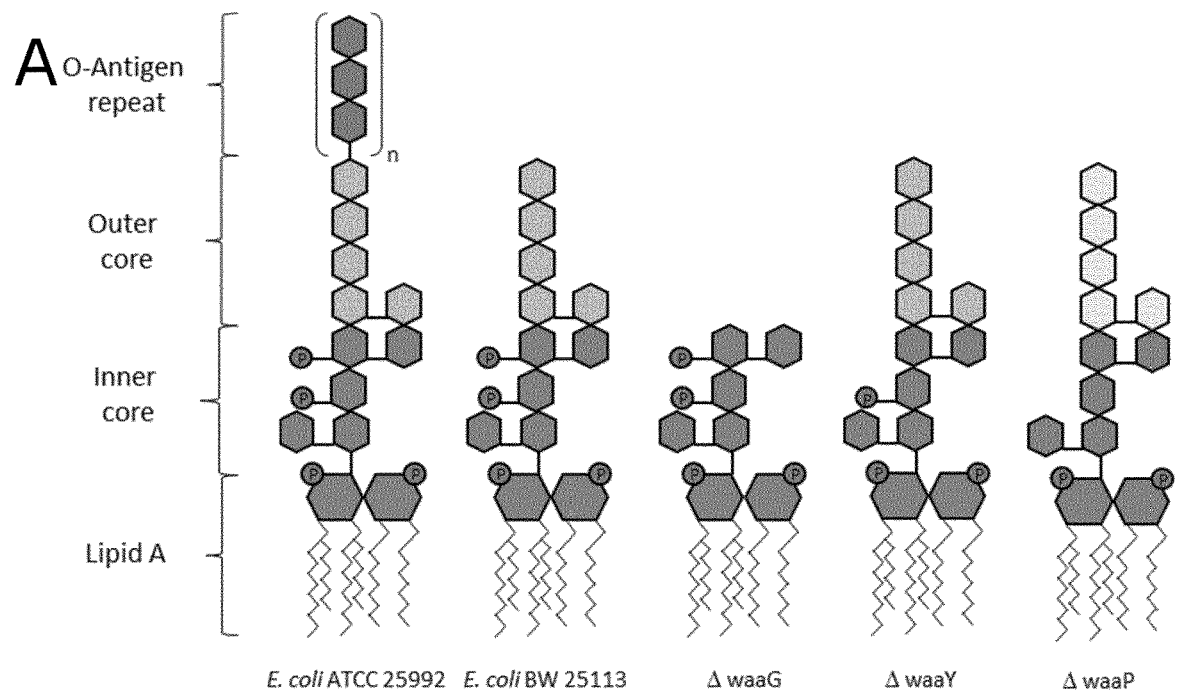
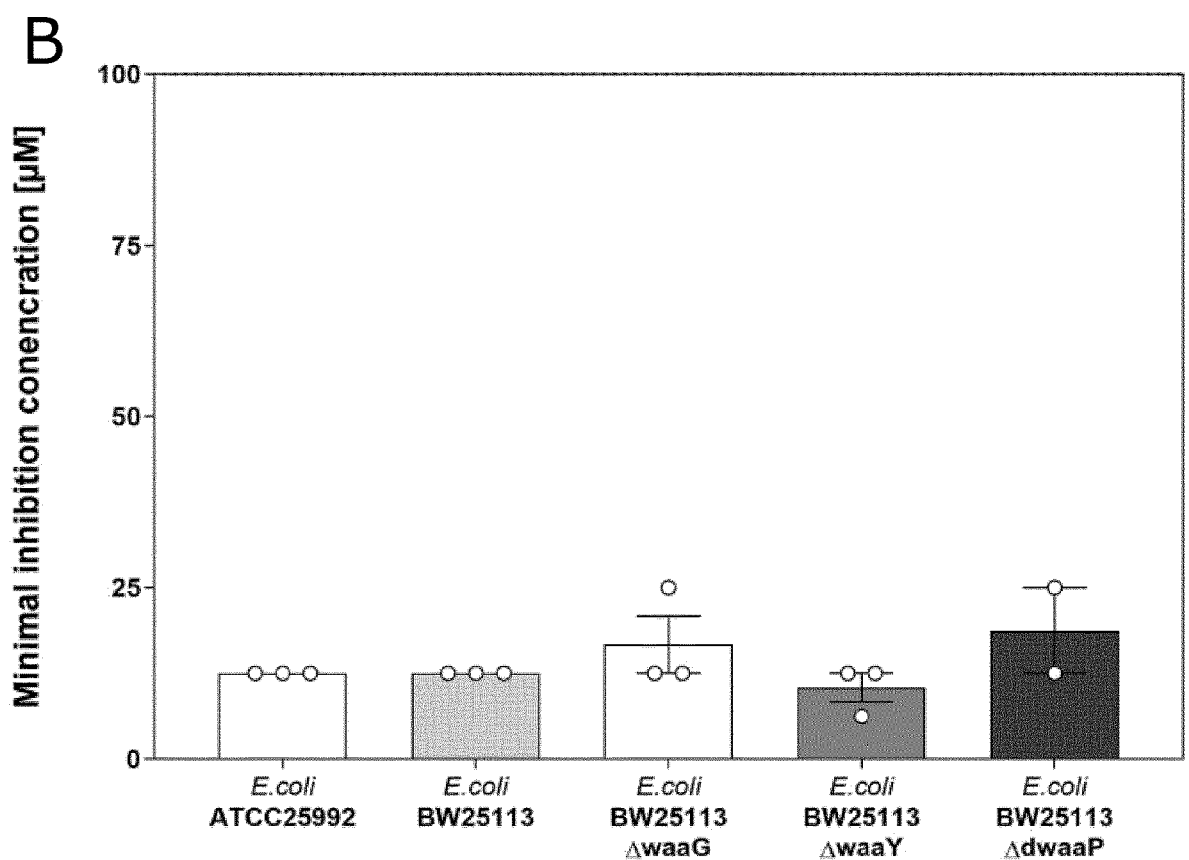
Fig. 16

Fig. 21

| Commensal bacteria | HNP-4 | | | pathogenic bacteria | HNP-4 | | |
|---|---|---|---|---|---|---|---|
| | fl | 1-11 | 1-11mod | | fl | 1-11 | 1-11mod |
| B. subtilis 168trpC | | | | A. baumannii DSM 30007 | | | |
| B. breve | | | | E. coli EPEC | | | |
| B. longum | | | | E. coli UPEC | | | |
| B. adolescentis Ni3,29c | | | | K. pneumoniae DSM 30104 | | | |
| B. vulgatus | | | | P. aeruginosa ATCC 27853 | | | |
| E. coli MC1000 | | | | S. enterica serovar enteriditis | | | |
| L. fermentum | | | | E. faecalis DSM 20478 | | | |
| L. rhamnosus | | | | E. faecalis ATCC 29212 | | | |
| L. salivarius | | | | E. faecium DSM 20477 | | | |
| S. salivarius salivarius | | | | S. aureus ATCC 25923 | | | |
| | | | | S. epidermidis DSM 20044 | | | | high activity | low activity | no activity

DEFENSIN FRAGMENTS FOR USE IN THERAPY OR PROPHYLAXIS

The present invention relates to specific peptide sequences derived from alpha defensins and their use in medical therapy and/or prophylaxis.

Anaerobic and aerobic microorganisms, especially bacteria and yeasts, i.e. unicellular microorganisms that live with oxygen, without oxygen or are oxygen-tolerant, can cause various clinical pictures, for example wound infections and abscesses, sepsis, infections, especially in the abdominal cavity, in the urogenital tract, on the skin or in the mouth, eyes, ears, and jaw region. Thus, these pathogenic species are often already found in the region of the skin and oral cavity, especially in the inflamed skin/eczema, the periodontium, the eyes and ears and in the region of the stomach in the mucosal folds of the stomach, and in the duodenum, which can then cause local, but also in some circumstances systemic acute and chronic inflammations. Even in the rather thinly colonized small intestine, a number of facultative anaerobes can cause pathological changes of the highly sensitive mucosa of the small intestine; in the rectum, the principal site of the bacterial flora, admittedly aerobic bacteria predominate, but here too, anaerobic representatives are also capable of causing serious inflammatory reactions of the mucosa of the colon. *Candida* ssp. are also found in the stool of many individuals and are potentially pathogenic.

At present, in particular such diseases are treated with antibiotics, which mainly attack and destroy the cell walls of the bacteria. A big problem that arises when these inflammatory diseases are treated with antibiotics is the development of resistance to the antibiotics used, which in recent times has progressed even further. This enables the pathogenic bacteria/microorganisms to weaken or completely neutralize the action of antibiotic substances. If a microorganism then proves to be resistant to the common antibiotics, diseases can become life-threatening. The reason why in the past the number of multi resistant bacterial strains has increased considerably is that, owing to their rapid growth and their short culture period, the bacteria are continually able to develop new strategies for neutralizing the antibiotics. Therefore at present, in addition to antibiotics, for example also natural, especially plant, and synthetic oils and emulsions are used.

In recent years, antimicrobial peptides, which are part of the natural immune system and are vitally important for epithelial defense against infection by microorganisms, have gained research and therapeutic appliance interests.

In a healthy person the skin and mucosa form a physical barrier to infection by microorganisms. The physical barrier is made up of the stratum corneum in healthy skin and, in the mucosa, of the mucous layer in which desquamation and mucous secretion cause a constant renewal of the surfaces, simultaneously with continuous elimination of microorganisms that are adhering to the surfaces. In interaction with the lipids that are also present in the skin, this physical barrier prevents microorganisms from penetrating into the living epidermis.

Leaving aside this physical barrier, however, further factors are also necessary in order for the healthy skin and mucosa to defend against infection; among these factors are endogenous antimicrobial peptides (AMPs). Lysozyme, for example, is an antimicrobial peptide that is present in nasal secretions and can in particular kill Gram-positive bacteria. Also known as antimicrobial peptides in the intestinal mucosa are defensins, whose presence appears to be necessary especially given that the intestinal epithelia is exposed to very large quantities of bacteria. In addition to having a mucous layer that is difficult for microorganisms to penetrate, the intestinal mucosa contains Paneth cells that secrete human defensin-5—an alpha defensin—that among other functions, protect the stems cells that are important for continuous renewal of the intestinal mucosa. In humans, only alpha- and beta-defensins are expressed. While alpha-defensins are expressed primarily in neutrophils as well as in NK cells and certain T-lymphocyte subsets, human defensin 5 and defensin 6 are expressed exclusively in Paneth cells of the small intestine, where they contribute in regulating and maintaining microbial balance in the intestinal lumen. On the other hand, beta-defensins are most widely distributed, being secreted by leukocytes and epithelial cells of many kinds. Further known AMPs are a peptide known as psoriasin, as well as RNas-7, which represents an effective endogenous broad-spectrum antibiotic in humans.

In addition to the known endogenous antimicrobial peptides, numerous antibiotics are also known in the existing art; these include both substances of biological origin and synthetically manufactured substances, which are therefore either (as in the original sense) naturally formed low-molecular-weight metabolic products of fungi or bacteria, or chemically synthesized therapeutic agents.

Especially in light of the fact that the development of resistance to natural and synthetic antibiotics is making microbial infectious diseases increasingly difficult to treat, a need also frequently arises for novel antimicrobial active agents that are notable for few side effects and for simple manufacture and handling.

The gastrointestinal microenvironment is comprised of a single cell layer epithelia, a mucus layer, a local immune system, and the microbiome, and together these four components play a crucial role in maintaining homeostasis during times of health. The human colon harbors a highly dense microbial community of $10^{11}$-$10^{12}$ cells per gram of gut content, and human health is closely linked to the diverse set of microorganisms in the intestine collectively known as the gut microbiota. While on one hand, their abundance and prevalence are associated with disease—as it can be the case with *Faecalibacterium prausnitzii* in, e.g., inflammatory bowel disease (IBD) and infectious colitis, it has been shown, on the other hand, that mucosal species such as *Bacteroides fragilis*, and *Lactobacillus reuteri* can protect against colitis.

As a consequence, when applying antibiotics in case of an infection, the microbiome composition in human colon gets majorly affected, and the microbe balance disturbed. Defensins are small cationic molecules, characterized by three conserved disulphide bonds and represent a main group of AMPs. To date, six alpha-defensins have been identified in humans, namely the four Human Neutrophil Peptides (HNP) 1, 2, 3 and 4, and the two Human Defensin (HD) 5 and 6. While the HNPs form part of the armory of neutrophils, where they participate in systemic innate immunity, the HDs are expressed in intestinal Paneth cells. As mentioned above, in the small intestine, Paneth cells play a key role in balancing the microbiota composition and in protecting the host from invading pathogens by secretion of a variety of AMPs but most abundantly the two α-defensin 5 (HD 5) and -6 (HD 6).

While HNP-1, HNP-2 and HNP-3 only differs in a single amino acid, HNP-4 varies in its sequence, has one additional positive charge and exhibits improved bactericidal activity compared to HNP-1-3[1,2]. The activity of full length antimicrobial peptides are influenced by environmental conditions including salt concentration, pH or redox potential 3-6. Based on its strong antimicrobial activity we used HNP-4 as a precursor for a new therapeutic agent with antimicrobial abilities. While large-scale expression of accurately folded defensins is a major issue, we focused on small fragments of HNP-4. We used a natural occurring protease to digest the full length peptide and subsequently identified the generated fragments. We tested these fragments for their antibacterial and antifungal potential and analyzed their cytotoxic and hemolytic abilities.

The antimicrobial activity of alpha-defensins has been intensively studied in the past, and it has been acknowledged that alterations in their specific sequences can contribute to major changes of their activity and may even lead to a complete loss of antimicrobial activity.

SUMMARY OF THE INVENTION

The problem to be solved by the present invention is therefore to provide a new or alternative preventive and/or therapeutic approach, by means of which infectious diseases but also other diseases associated with dysbiotic conditions, e.g. metabolic diseases, lung diseases, urogenital diseases, diseases of the mouth, eyes and ears and skin diseases, can be prevented and/or effectively treated.

According to the invention, this and other problems are solved by the provision of peptides having antimicrobial activity and having an amino acid sequence derived from an alpha-defensin fragment, which peptide consists of between 6 and 27, in particular the shorter peptide fragments, which can be synthesized as linear peptides, for example those having 7, 9, 11, or 13, successive amino acids.

Common for the peptides is that they are fragments of naturally occurring alpha defensins, HD-5 and HNP-4 and can be produced by reducing the naturally occurring peptides and subjecting them to cleavage using proteases activity. Surprisingly, a related peptide, HD-6 which includes a number of predicted cleavage sites, could not be cleaved under the same conditions.

These short fragments of naturally occurring alpha-defensins have the advantage that they can be synthesized chemically as small linear peptide thus reducing the cost significantly compared to the manufacture of full length peptides. Furthermore, several of the peptides have retained the antibiotic effects of the naturally occurring full length defensins, while being non-toxic at efficacious concentrations.

These peptides can be used for modulating the microbiome of intestines and/or as an antimicrobial agent without inducing major shifts/disturbing the balance of the healthy microbiome.

Within the present invention, peptide sequences of alpha-defensins have been identified which, in antimicrobial tests, showed to have an increased antimicrobial effect on certain (in particular: pathogenic) bacteria as compared to the full length peptide on one hand, while on the other hand there was no effect of the newly identified peptides on the microbial diversity.

These results allow the appliance of the peptides according to the invention not only for treating microbial infections and bacterially caused diseases, even those diseases that are caused by antibiotic-resistant bacteria, but also for preventing bacterial infections and for modulating the gut microbiome and potentially the microbiome of other epithelial surfaces e.g. lung, skin, genitourinary tract, mouth, eyes, ears etc.

Accordingly, within the present invention, and as generally understood in the field, "modulating the microbiome" means the beneficial influence of the peptides on the microorganisms present in the gut and epithelial surfaces. As mentioned above, gut microbes are key to many aspects of human health including immune, metabolic and neuro behavioral traits. With the peptides for use according to the invention, the bacterial diversity of the gut microbiome and potentially the bacterial diversity of other epithelial surfaces can be supported and promoted.

With "gut microbiome" the gut of a mammal, in particular of a human, is meant. Accordingly, a preferred embodiment of the invention is directed to the peptide for use in modulating the gut microbiome of humans.

According to an embodiment of the peptide of the invention the alpha-defensin fragment is a fragment of HD-5 or HNP4.

HD-5, as mentioned at the outset, is expressed in Paneth cells of the small intestine. Including a signal peptide and a prodomain, HD 5 comprises 94 amino acids, with the mature peptide comprising amino acid numbers 63 to 94.

HNP4, also as mentioned at the outset, expressed in the granules of neutrophils. Including the signal peptide and a prodomain, HNP4 comprises 97 amino acids, with the mature HNP4 peptide comprising amino acid numbers 64 to 96.

According to a preferred embodiment of the invention, the peptide for use according to the invention consists of between 6 and 27 successive amino acids derived from HD-5 and consists of the sequence HD-5$_{1-9}$ ATCYCRTGR (SEQ ID No. 1) or the reverse sequence of SEQ ID No. 1, RGTRCYCTA (SQ ID No. 2), modified HD-5$_{1-9}$: Ac-atcycrtGr-NH$_2$ (SEQ ID No. 5), HD-5$_{1-13}$,
(SEQ ID No. 34)
ATCYCRTGRCATR, HD-5$_{1-28}$,
(SEQ ID No. 12)
ATCYCRTGRCATRESLSGVCEISGRLYR, HD-5$_{7-32}$,
(SEQ ID No. 14)
TGRCATRESLSGVCEISGRLYRLCCR HD-5$_{10-32}$,
(SEQ ID No. 19)
CATRESLSGVCEISGRLYRLCCR, HD-5$_{14-32}$,
(SEQ ID No. 25)
ESLSGVCEISGRLYRLCCR HD-5$_{10-27}$
(SEQ ID No. 28)
CATRESLSGVCEISGRLY or HD-5$_{26-32}$
(SEQ ID No. 41)
LYRLCCR of the attached sequence listing.

In general for amino acid sequences, capital letters designate L-amino acids and small letters designate D-amino acids.

In a preferred embodiment the peptide consists of the sequence of

ATCYCRTGR, (SEQ ID No. 1)

RGTRCYCTA, (SEQ ID No. 2)

Ac-atcycrtGr-NH$_2$, (SEQ ID No. 5)

LYRLCCR, (SEQ ID No. 41)

ATCYCRTGRCATR, (SEQ ID No. 34)

ATCYCRTGRCATRESLSGVCEISGRLYR, or (SEQ ID No. 12)

TGRCATRESLSGVCEISGRLYRLCCR. (SEQ ID NO. 14)

More preferably the peptide consists of the sequence of

ATCYCRTGR, (SEQ ID No. 1)

RGTRCYCTA, (SEQ ID No. 2)

Ac-atcycrtGr-NH$_2$, or (SEQ ID No. 5)

LYRLCCR. (SEQ ID NO. 41)

Preferred peptide include those based on HD-5$_{1-9}$:

ATCYCRTGR, (SEQ ID No. 1)

RGTRCYCTA, or (SEQ ID No. 2)

Ac-atcycrtGr-NH$_2$, (SEQ ID NO. 5)

According to a preferred embodiment of the invention, the peptide for use according to the invention consists of either 7, 9, 11, or 13 successive amino acids.

According to a preferred embodiment of the invention, the peptide for use according to the invention consists of 9 successive amino acids derived from HD-5, and preferably consists of the sequence ATCYCRTGR (SEQ ID No. 1) or the reverse sequence of SEQ ID No. 1, RGTRCYCTA (SEQ ID No. 2) of the attached sequence listing.

According to another preferred embodiment of the invention, the peptide for use according to the invention consists of 11 successive amino acids derived from HNP4, and preferably consists of the sequence VCSCRLVFCRR (SEQ ID No. 3), of the reverse sequence of SEQ ID No. 3, RRCFVLRCSCV (SEQ ID No. 4), or of the modified HNP-4$_{1-11}$: Ac-vcscrlvfcrr-NH$_2$ (SEQ ID NO. 6).

In one embodiment, the invention relates to a method of manufacturing the peptides of the invention comprising subjecting reduced HD5 or HNP-4 to protease activity, e.g. trypsin or chymotrypsin, followed by purification.

The peptides as herein disclosed and described, being derived from HD-5 or HNP4, have been shown to exhibit excellent antimicrobial activities against pathogenic bacteria, while at the same time not notably influencing the commensal microbiota, e.g. the gut microbiota.

According to a preferred embodiment, the peptide for use according to the invention comprises L- and/or D-amino acids.

Presently and as generally understood, an "L-amino acid" refers to a stereoisomer of a particular amino acid whose amino group is on the left side in its Fisher projection while D-amino acid refers to the other stereoisomer of the amino acid whose amino group is on the right side in its Fisher projection. In sequences herein, L-amino acids are shown in capital and D-amino acids in small letters.

While most naturally occurring peptides are composed of amino acids in the L-configuration, D-amino acids have shown strong resistance to proteolytic degradation.

Thus, according to a preferred embodiment, the peptides according to the invention consist of D-amino acids.

According to another embodiment, the peptides according to the invention consist of L-amino acids.

According to another embodiment, the peptides according to the invention consist of a mixture of D- and L-amino acids, preferably alternating D- and L-amino acids, or comprises preferably one L-amino acid, with the remaining amino acids being D-amino acids.

According to a preferred embodiment, the peptide for use according to the invention comprises N- and/or C-terminal modifications.

With N- and/or C-terminal modifications it is possible to influence/enhance, e.g., the stability or the half-life of the peptide according to the invention, in particular in environments that promote degradation and/or modification of the free N-/C-terminal ends of peptides, e.g. due to proteases present in those environments.

Presently, and as generally understood, the C-terminus (also known as the carboxyl-terminus, carboxy-terminus, C-terminal tail, C-terminal end, or COOH-terminus) is the end of an amino acid chain (protein or polypeptide), terminated by a free carboxyl group (—COOH), and the N-terminus (also known as the amino-terminus, NH$_2$-terminus, N-terminal end or amine-terminus) is the start of a protein or polypeptide referring to the free amine group (—NH$_2$) located at the end of a polypeptide. The convention for writing peptide sequences is to put the C-terminal end on the right and write the sequence from N- to C-terminus.

According to a preferred embodiment, in the peptide for use according to the invention, the C-terminal modification is selected from one of the group consisting of: -Amide, -Acid, —N-alkyl-Amide, -Aldehyde, -Ester, -p-Nitroanilide, and -7-Amino-4-Methylcoumarin.

With these modifications, the C-terminal end of the peptide can be protected without influencing the antimicrobial activity of the peptide to a major extent.

According to a preferred embodiment, in the peptide for use according to the invention, the N-terminal modification is selected from one of the group consisting of Acetyl-, Formyl-, Pyroglutamyl-, Fatty acids-, urea-, Carbamate-, and alkylamine-.

It is to be understood, that either both ends, i.e. the N-terminus and the C-terminus can be modified with any of the above described modifications, or only one of the ends, i.e. either the N- or the C-terminus.

According to a preferred embodiment, in the peptide for use according to the invention, the N-terminus, carries an acetyl-(ac) modification, and no modification at the C-terminus.

According to a preferred embodiment, the peptide for use according to the invention, the peptide consists of (or comprises) D-amino acids, and carries, at the N-terminus, an acetyl-(ac) modification, and no modification at the C-terminus.

With an N-terminal acetylation, the charge from the amino terminus of a peptide is removed; also, with an acetyl modification, a peptide is meant to imitate its natural structure in a protein. In addition, this modification stabilizes the resulting peptide towards enzymatic degradation resulting from exopeptidases.

According to a preferred embodiment, the peptide according to the invention carries a N-terminal acetyl-modification and a C-terminal amide-modification.

With a C-terminal amide modification, the peptide is meant to imitate its natural structure in a protein. In addition, this modification avoids the introduction of additional charges in the peptide molecule.

According to a preferred embodiment, the peptide according to the invention comprises 9 amino acids, wherein 8 amino acids are D-amino acids, and 1 amino acid is a L-amino acid, and further preferably, this peptide comprises an N-terminal acetyl-modification and a C-terminal amide-modification.

According to a preferred embodiment, the peptide according to the invention comprises 11 amino acids, wherein all amino acids are D-amino acids, and further preferably this peptide comprises an N-terminal acetyl-modification and a C-terminal amide-modification.

According to another preferred embodiment, the peptide according to the invention is a chemically synthesized peptide or a biologically expressed peptide.

A wide variety of methods for chemically synthesizing peptides are known in the art; while the chemical synthesis of peptides can be carried out using classical solution-phase techniques, these have been replaced in most research and development settings by solid-phase methods. An overview of peptide synthesis can be found, e.g. in Stawikowski et al., ("Introduction to peptide synthesis", Cur. Prot. Prot. Sci., (2012), suppl. 69, 18.1.1-18.1.13)[7].

According to an embodiment of the peptide for use of the invention, the peptide is in an oxidized or reduced state.

In this connection, "oxidized" refers to the state of the peptide where disulfide bridges, which occur in peptides having amino acid residues such as cysteine, methionine, tryptophan, histidine and tyrosine. The "reduced" state or from designates the form of the peptide not having formed disulfide bonds.

"Biologically expressed" peptide, within the present invention, shall encompass the expression of the peptide(s) for use according to the invention by a genetically engineered host cell that has been modified to express said peptide(s).

As used herein, the term "host cell" is presently defined as a cell which has been transformed or transfected, or is capable of transformation or transfection by an exogenous polynucleotide sequence encoding the peptide for use according to the invention.

A variety of host-expression vector systems may be utilized to express the gene coding a peptide for use according to the invention. Such host-expression systems represent vehicles by which the coding sequences of interest may be produced and subsequently purified, but also represent cells which, when transformed or transfected with the appropriate nucleotide coding sequences, exhibit the peptide for use gene product of the invention in situ.

For recombinant production, host cells can be genetically engineered to incorporate expression systems or portions thereof or polynucleotides encoding the peptides for use of the invention. Introduction of a polynucleotide into the host cell can be effected by methods described in many standard laboratory manuals, such as Davis et al., Basic Methods in Molecular Biology, (2012)[8], and Sambrook et al., 1989[9].

Thus, the polynucleotide encoding the peptide according to the invention, may, e.g., be comprised in a vector which is to be stably transformed/transfected into host cells. In the vector, the polynucleotide encoding the peptide(s) of the invention is under control of an, e.g., inducible promoter, so that the expression of the gene/polynucleotide can be specifically targeted, and, if desired, the gene may be overexpressed in that way.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., see above According to a preferred embodiment, the peptide for use according to the invention is selected from at least one of the followings:

HD-5$_{1-9}$:
ATCYCRTGR
(SEQ ID No. 1)

HD-5$_{1-9rev}$:
RGTRCYCTA
(SEQ ID No. 2)

HD-5$_{1-9mod}$:
Ac-atcycrtGr-NH$_2$
(SEQ ID No. 5)

HNP-4$_{1-11}$:
VCSCRLVFCRR
(SEQ ID No. 3)

HNP-4$_{1-11rev}$:
RRCFVLRCSCV
(SEQ ID No. 4)

HNP-4$_{1-11mod}$:
Ac-vcscrlvfcrr-NH$_2$
(SEQ ID NO. 6)

According to another aspect of the invention, the use of the peptide in modulating the microbiome consists of the use in the treatment and/or prophylaxis of intestinal, lung, urogenital, mouth, eye, ear or skin or other conditions or diseases associated with a dysbiotic condition.

As mentioned above, a healthy gut microbiome, containing diverse bacterial microorganisms, is mandatory not only for an intact gut, but for overall health in mammals, in particular humans. A lower bacterial diversity has been reproducibly observed in people with diseases such as, inter alia, inflammatory bowel disease, coeliac disease, but also metabolic diseases like obesity and type 2 diabetes and the efficacy of e.g. check point inhibitor treatment of cancer is also highly influenced by the microbiome and even CNS diseases like schizophrenia has been reported to be influenced by the microbiome. The association between reduced diversity and disease indicates that a species-rich gut ecosystem is more robust against environmental influences, as functionally related microbes in an intact ecosystem can compensate for the function of other missing species.

Apart from genetically influenced intestinal diseases, also specific food and dietary patterns as well as medications can influence the abundance of different types of bacteria in the gut. While often associated with a change of the nutrition or diet positive effects on the gut microbiome can be observed, and also by using pre- and probiotic foods, the peptide according to the invention, due to its natural origin, provides for a broader, more convenient and highly efficient tool. Also with the peptide according to the invention, a treatment of subjects is possible that are otherwise highly sensitive towards nutritional changes and influences.

With the peptide for use according to the invention, intestinal diseases but also diseases of the lungs, the skin and the brain can be efficiently prevented and/or treated, by positively influencing the natural microbiome of the gut.

Thus, in a preferred embodiment, the peptide according to the invention is used in preventing/treating a disease that is selected from inflammatory bowel disease, in particular Crohn's disease, ulcerative colitis, coeliac disease, necrotizing enterocolitis, irritable bowel syndrome, tourist diarrhea, gastro-intestinal cancers and intestinal graft versus host disease, and from metabolic diseases, preferably diabetes and pre-diabetes, obesity, NAFLD, NASH, dyslipidemia, and from diseases of the lung, preferably asthma and COPD, and from diseases of the brain, preferably schizophrenia, Parkinsonism, bipolar disorder, autism and depression.

With the peptide according to the invention, diseases associated with the simple microbiomes of the skin, mouth, eye, ear, vagina or circulation can be efficiently prevented and/or treated.

Thus, in a preferred embodiment, the peptide according to the invention is used in preventing/treating a disease that is selected from sepsis, atopic dermatitis, rosacea, seborrheic dermatitis, eczema, carbuncles, staph infection, candidiasis, cellulitis, impetigo, acne, pilonidal cyst, Athletes food, ringworm, molluscum, cutaneous lymphoma, periodontitis, caries, Dry eye, Sjögrens Disease, conjunctivitis, blepharitis, hordeola, chalazia, periorbital cellulitis, dacryocystitis, endolphalmitis, uveitis, iritis, mastoiditis, vestibular neuronitis, bullous myringitis, granular myringitis, otitis externa, otitis media, bacterial vaginosis, *Trichomonas* vaginitis, *candida*, non-infectious vaginitis, inflammatory vaginitis.

According to another aspect, the peptide as described herein can also be used as an antimicrobial agent against multi drug resistant bacteria induced infections. Within the present invention it has been found that the peptide according to the invention can not only be used to positively influence the natural gut microbiome, but also as a tool for specifically targeting multi drug resistant bacteria, thus, being an efficient tool for treating/preventing infections caused by multi-drug resistant bacteria. According to another object, the present invention also relates to a medicament comprising the peptide according to the invention and a pharmaceutically acceptable carrier.

Presently, and as generally understood in the field, a "pharmaceutically acceptable carrier" is understood to mean any excipient, additive, or vehicle that is typically used in the field of the treatment of the mentioned diseases and which simplifies or enables the administration of the product according to the invention to a living being, and/or improves its stability and/or activity. The pharmaceutical composition can also incorporate binding agents, diluting agents or lubricants. The selection of a pharmaceutical carrier or other additives can be made on the basis of the intended administration route and standard pharmaceutical practice. As pharmaceutical acceptable carrier use can be made of solvents, extenders, or other liquid binding media such as dispersing or suspending agents, surfactant, isotonic agents, spreaders or emulsifiers, preservatives, encapsulating agents, solid binding media, depending upon what is best suited for the respective dose regime and is likewise compatible with the compound according to the invention. An overview of such additional ingredients can be found in, for example, Rowe (Ed.) et al.: Handbook of Pharmaceutical Excipients, 7th edition, 2012, Pharmaceutical Press[10].

A peptide of the present invention can be used for treatment of skin-conditions when formulated for topical administration. Methods for topical administration are known in the art.

When formulated for topical administration, the composition of the present invention may contain ingredients typical in topical pharmaceutical or cosmetic compositions, such as a carrier, vehicle or medium. Specifically, the carrier, vehicle, or medium is compatible with the tissues to which it will be applied, such as the skin, hair, nail, vagina, urethra, ear, oral cavity, nasal passage, respiratory system, opthalmic region, and/or mucosa. The compositions and components of the invention are suitable for contacting infected tissues or for use in patients in general without undue toxicity, incompatibility, instability, allergic response, and the like. As appropriate, compositions of the invention may comprise any ingredient conventionally used in the fields under consideration.

In terms of their form, compositions of this invention may include solutions, emulsions (including microemulsions), suspensions, creams, lotions, gels, powders, or other typical solid or liquid compositions used for application to skin and other tissues where the compositions may be used. Such compositions may contain: additional antimicrobials, moisturizers and hydration agents, penetration agents, preservatives, emulsifiers, natural or synthetic oils, solvents, surfactants, detergents, gelling agents, emollients, antioxidants, fragrances, fillers, thickeners, waxes, odor absorbers, dyestuffs, coloring agents, powders, viscosity-controlling agents and water, and optionally including anesthetics, anti-itch actives, botanical extracts, conditioning agents, darkening or lightening agents, glitter, humectants, mica, minerals, polyphenols, silicones or derivatives thereof, sunblocks, vitamins, and phytomedicinals. In certain embodiments, the composition of the invention is formulated with the above ingredients so as to be stable for a long period of time, as may be beneficial where continual or long-term treatment is intended.

The compositions of the invention may be in the form of controlled-release or sustained-release compositions, wherein the antimicrobial peptide along with additional active agents are encapsulated or otherwise contained within a material, such that they are released onto the skin or affected area in a controlled manner over time. The compositions of the invention may be contained within or on matrixes, liposomes, vesicles, microcapsules, microspheres and the like, or within or on a solid particulate material.

Administration of the composition of the invention may be to any affected or susceptible region, for example, to the legs, shoulders, back (including lower back), axilla, palms, feet, neck, groin, dorsa or the hands or feet, elbows, upper arms, knees, upper legs, buttocks, torso, pelvis, or any other part of the body for which treatment or prevention of infection may be desired. Such treatment is also contemplated for treating and/or dressing wounds, such as cuts, scrapes, and burns to the skin, so as to treat or prevent infection of the wounded area.

The compositions of the invention are suitable for use in physiologic environments with a pH ranging from about 4.5 to about 6.3, and thus, the compositions may be formulated at a similar or equivalent pH. The compositions according to this invention may be stored either at room temperature or under refrigerated conditions. The composition of the invention contains an amount of antimicrobial peptide effective for antimicrobial action. Generally, the composition contains from about 0.01% (wt./vol.) to about 20% antimicrobial peptide. In certain embodiments, the composition contains from about 0.5% to about 10% antimicrobial peptide, such as about 0.5%, about 1%, about 5%, or about 10% antimicrobial peptide.

The features, characteristics and advantages of the peptide according to the invention apply likewise to the medicament according to the invention. Accordingly, the medicament containing the peptide according to the invention can also be used for treating and/or preventing a disease that is selected from inflammatory bowel disease, in particular Crohn's disease, ulcerative colitis, coeliac disease, necrotizing enterocolitis, irritable bowel syndrome, tourist diarrhea, gastro-intestinal cancers and intestinal graft versus host disease, but also metabolic diseases, preferably diabetes and pre-diabetes, obesity, NAFLD, NASH, dyslipidemia, and diseases of the lung, preferably asthma and COPD; and diseases of the skin such as atopic dermatitis, rosacea, seborrheic dermatitis, eczema, carbuncles, staph infection, candidiasis, cellulitis, impetigo, acne, pilonidal cyst, Athletes food, ringworm, molluscum, cutaneous lymphoma; diseases of the mouth such as periodontitis and caries; diseases of the eye such as Dry eye, Sjögrens Disease, conjunctivitis, blepharitis, hordeola, chalazia, periorbital cellulitis, dacryocystitis, endolphalmitis, uveitis, iritis; diseases of the ear such as mastoiditis, vestibular neuronitis, bullous myringitis, granular myringitis, otitis externa, otitis media; diseases of the vagina such as bacterial vaginosis, *Trichomonas* vaginitis, *candida*, non-infectious vaginitis, inflammatory vaginitis as well as sepsis and psychiatric diseases, preferably schizophrenia, Parkinsonism, bipolar disorder, depression or autism.

According to another preferred embodiment, the peptide is present as dimer, preferably a homodimer. The dimers are preferably bound via a covalent bond, suitably a disulfide bond.

Dimerization of peptides is known in the art. The chemistry currently used for peptide dimerization involves chemoselective reactions between unprotected peptides. Examples are the formation of the following bonds, e.g., Cys-maleimide thioethers, disulfides or triazoles.

It is to be understood that the before-mentioned features and those to be mentioned in the following cannot only be used in the combination indicated in the respective case, but also in other combinations or in an isolated manner without departing from the scope of the invention.

The invention is now further explained by means of embodiments resulting in additional features, characteristics and advantages of the invention. The embodiments are of pure illustrative nature and do not limit the scope or range of the invention.

The features mentioned in the specific embodiments are also features of the invention in general, which are not only applicable in the respective embodiment but also in an isolated manner in the context of any embodiment of the invention.

The invention is also described and explained in further detail by referring to the following drawings:

FIG. 1 shows the results of experiments for proving that HD-6 nanonet formation is not affected by duodenal fluid: (A) shows the chromatograph of HD-6 incubated with duodenal fluid after reduction with 2 mM TCEP. Only the oxidized and reduced full-length peptides were detected, due to their retention time with their m/z graphs and their 2-, 3-, 4-, 5- and 6-fold protonated ions and neutral masses. (B) shows incubated reduced beads with 200 µg/ml HD-6 or 0.01% HAc (control) and duodenal fluid or 0.9% NaCl (control). The nanonet formation was not affected as these nets look the same as HD-6 with 0.9% NaCl. Magnification bar=0.2 µm.

FIG. 2 shows the results of experiments where incubation of HD-5 and duodenal fluid led to many different fragments. HD-5 was incubated with duodenal fluid after reduction with 2 mM TCEP. (A) shows the overview of the chromatogram from incubation of reduced HD-5 with duodenal fluid. All detectable fragments were marked in grey (a-m) and listed due to their retention time in (B). The mass-to-charge (m/z) graphs of all identified fragments with the detected ions and their neutral masses. The peptides (a), (b), (c), (e), (i), (j), (k), (l) and (m) were chosen for synthesis and deeper investigation of their abilities. (C) Here the chosen fragments are listed (in grey) with their amino acid sequence and their distribution over the HD-5 sequence.

FIG. 3 shows the results of experiments proving that HD-5 fragments are antimicrobial active peptides against commensal bacteria: (A) shows a table summarizing the testing of different commensal bacteria due to their susceptibility to HD-5 fragments. In this heat map all bacteria are listed and the activity of the fragments in RDA against them. In the RDA 2 µg of the full length and 4 µg of each fragment were used. An inhibition zone greater than 5 mm was determined as high activity, between 2.5 and 5 mm as low activity and 2.5 mm were the diameter of the punched well and therefore no activity. (B) Here, in diagrams, the original data from (A) are placed with mean and standard deviation from at least three independent experiments. (C) shows electron microscopy pictures investigating the mode of action of the different peptides: *E. coli* MC1000 was incubated with all different fragments and transmission electron microscopy was performed and the resulting phenotypes were analyzed. Magnification bars of all pictures are 0.5 µm except the full-length peptide, HD-5 (1 µm).

FIG. 4 shows the results of experiments proving the antimicrobial activity of the different fragments against pathogenic bacteria: (A) shows a table summarizing the testing of the antimicrobial activity of HD-5 fragments against pathogenic bacteria. A heat map system with high activity (inhibition zone in the RDA>5 mm), low activity (2.5 to 5 mm) and no activity (2.5 mm) was used. (B) Shows diagrams of the data of (A) with mean and standard deviation from at least three independent experiments.

FIG. 5 shows the results of experiments proving that $HD5_{1-9}$ containing cysteine and arginine substitutions show hardly any antimicrobial effects against *E. coli* and *S. aureus* mutants. The minimal inhibition concentration (MIC) of $HD5_{1-9}$ and its variants was determined against (A) *E. coli* BW 25113 mutants and (B) *S. aureus* SA113 mutants due to the measurement of the optical density ($OD_{600}$) after 18 h. Results from three independent experiments with +/−SEM are represented.

FIG. 6 shows diagrams of experiments summarizing that reduction of $HD5_{1-9}$ and synthetic $HD5_{1-9}$ causes complete dissolving of its antimicrobial activity. The minimal inhibition concentration (MIC) was determined of (A) E. coli BW 25113 and (B) S. aureus SA113 with several concentrations of reduced and oxidized $HD5_{1-9}$ and dimer due to the measurement of the optical density after 18 h. Afterwards bacteria were plated out to confirm MIC. Results from three independent experiments with +/−SEM are represented.

FIG. 7 shows diagrams of experimental data showing that almost no reduction in the metabolic activity of $HD5_{1-9}$ treated cells was observed. To analyze the metabolic activity of $HD5_{1-9}$ and dimer treated cells, a WST-1 assay was performed. Cell lines were stimulated either with $HD5_{1-9}$ or $HD5_{1-9}$ dimer with concentrations between 3.123-100 µM and incubated for 24 h or 48 h. The activity is normalized to the negative control. As positive control, cells were treated with 2% Triton X-100 while treatment with 0.01% acetic acid was used as negative control. The results show the mean with +/−SEM of three independent experiments (A, B, C).

FIG. 8 shows the anti-microbial mode of action of $HD5_{1-9}$. Cell wall damages induced due to $HD5_{1-9}$ differ between E. coli ATCC 25922 and S. aureus SA113. In order to detect bacterial cell damages caused by $HD5_{1-9}$, a flow cytometry analysis was performed. $1.5 \times 10^6$ E. coli ATCC 25922 and S. aureus SA113 were incubated with different concentrations of $HD5_{1-9}$ (6.25 µM, 12.5 µM and 50 µM) for 1 h. Either (A) propidium iodide or the (B) membrane-sensitive $DiBAC_3$ (3) dye was used to stain bacteria. As positive control, 12.5 µM hBD3 was used while untreated cells function as negative control. Results from three independent experiments with +/−SEM are represented. (C) Transmission electron microcopy was performed to evaluate morphological changes of $HD5_{1-9}$ (200 µg/ml) treated E. coli MC1000. For comparison, the full length HD5 (HD5f) was used while treatment with 0.01% acetic acid (HAc) functions as negative control. Bars: Upper left panel: 1 µm; Upper right and lower left: 0.5 µm; lower right panel: 2 µm.

FIG. 9 shows results of investigations and experiments regarding Akkermansia in feces and susceptibility to $HD-5_{1-9}$ treatment: (A) The amount of Akkermansia sp. in feces samples (day 0, 7, 14) collected from mice treated for 7 days with $HD-5_{1-9}$ or PBS is increased in $HD-5_{1-9}$ treated animals compared to PBS treated ones (linear mixed-effect model; p=0.075). Here the mean is shown with the 80% confidence interval from n=6 per group. In (B) it was tested if Akkermansia muciniphila is susceptible to $HD-5_{1-9}$ treatment. (B) shows the growth rate compared to an untreated control in % after 72 hours of incubation at 37° C. in an anaerobic jar. A MIC from $HD-5_{1-9}$ against of Akkermansia could not be detected in this assay. The graph shows the mean with standard deviation of n=3.

FIG. 10 shows the pro- and anti-inflammatory immune response of $HD5_{1-9}$ stimulated human PBMCs. Human peripheral blood mononuclear cells (PBMCs) were isolated and stimulated with 10 µg/ml LPS (S. typhimurium) and different concentrations of $HD5_{1-9}$ followed by an incubation of 24 h. Supernatant of PBMCs was used to quantify the number of produced cytokines by a multi-analyte kit (LEG-ENDplex). The following cytokines were evaluated: Pro-inflammatory cytokines (A) TNF-α (B) IFN-γ (C) IL-1β (D) IL-6 (E) IL-8 and anti-inflammatory cytokine (F) IL-10. As negative control untreated cells were used and the cytokine concentration normalized to the negative control. The results show the mean with +/−SEM of three independent experiments. For statistical analysis a Kruskal-Wallis Test was performed. p>0.05=ns; p≤0.05=*; p≤0.01=; p≤0.001=*; p<0.0001=****.

FIG. 11 shows that the toxicity profile of $HD5_{1-9}$ and its dimerized form displays no cytotoxicity effects on human cell line. The (A) metabolic activity and (B) cytotoxicity of $HD5_{1-9}$ and dimer was determined using a WST-1 assay and LDH assay. HT29-MTX-E12 cells were stimulated either with $HD5_{1-9}$ or $HD5_{1-9}$ dimer with concentrations between 3.123-100 µM and incubated for 48 h. The activity was either normalized to the negative or positive control. As positive control, cells were treated with 2% Triton X-100 while treatment with 0.01% acetic acid was used as negative control. The results show the mean with +/−SEM of three independent experiments. (C) Further, the hemolytic activity of $HD5_{1-9}$ was analyzed. Red blood cell suspension was incubated with different concentrations of $HD5_{1-9}$. Hemolytic activity was normalized to the hemolytic activity of 0.1% Triton X-100. The experiments were carried out in duplicates.

FIG. 12 shows additional tox data. Almost no cytotoxic effects of TR 146 cells were observed after peptide treatment. An LDH assay was performed in order to evaluate cytotoxic effects of $HD5_{1-9}$ and dimer. Cell lines were stimulated either with $HD5_{1-9}$ or $HD5_{1-9}$ dimer with concentrations between 3.123-100 µM and incubated for 24 h or 48 h. The activity was normalized to the positive control. As positive control, cells were treated with 2% Triton X-100 while treatment with 0.01% acetic acid was used as negative control. The results show the mean with +/−SEM of three independent experiments. Cytotoxic effects of TR146 cells were evaluated for (A) $HD5_{1-9}$ after 24 h and 48 h as well as (B) $HD5_{1-9}$ dimer after 24 h and 48 h. Additional, the cytotoxicity of (C) $HD5_{1-9}$ and dimer was determined of HT29-MTX-E12 cells after 24 h.

FIGS. 14A and 14B show the overall small intestinal microbial community. PCoA of weighted and unweighted UniFrac distances using all mice sacrificed week 1 (n=6 per group) after 1 week of treatment comparing HD5 fl with $HD5_{1-9}$.

FIGS. 15A and 15B show the bacterial genera differently affected by full length and fragmented HD-5 treatment. Linear mixed model adjusted for cages on fecal microbiota day 0, 7 and 14 using all mice (note that n=12 per group day 0 and 7 and n=6 per group day 14). Only significantly different genera presented.

FIG. 16: Antimicrobial activity of $HD5_{1-9}$ against E coli ATCC 25922 and E. coli BW 25113 as well its LPS mutants. (A) Cell wall construction of E. coli BW 25113 mutants. E. coli ATCC 25922 contains the full-length LPS whereas the O-antigen is missing in E. coli BW 25113. The E. coli BW 25113 mutant ΔwaaG miss the outer core in contrast to ΔwaaY lacking some phosphate residues in the inner core. The last mutant ΔwaaP contains an outer core but no phosphate residues in the inner core. (B) The minimal inhibition concentration (MIC) of $HD5_{1-9}$ was determined against E coli ATCC 25922 and E. coli BW 25113 mutants with different peptide concentrations due to the optical density after 18 h. Results from at least two independent experiments with Mean+/−SEM are represented.

Figure 17A:
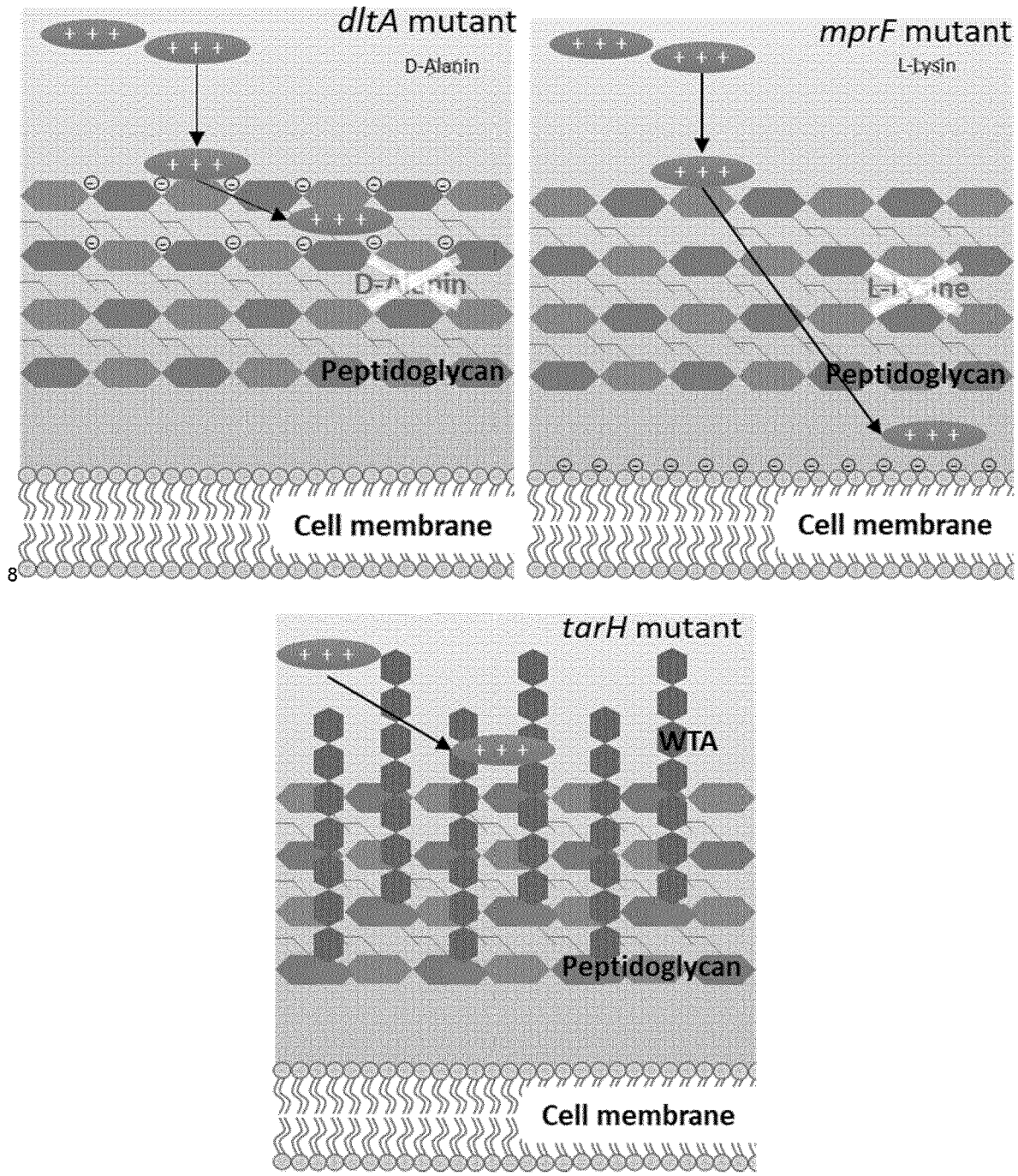
Figure 17B:
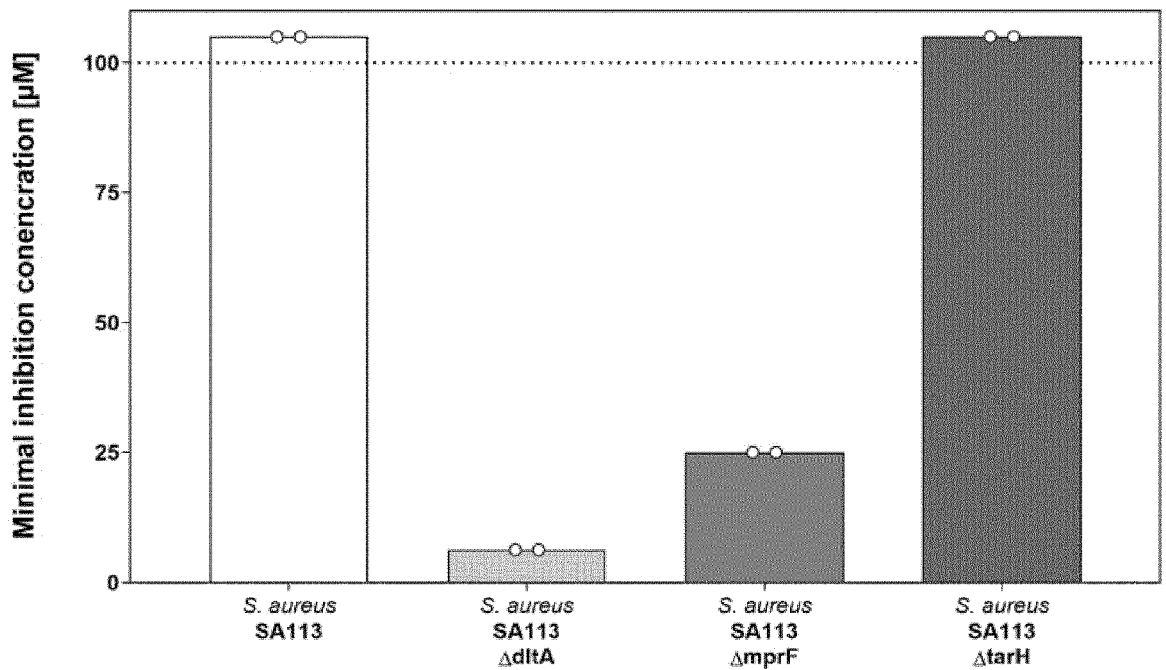

FIG. 17: Antimicrobial activity of $HD5_{1-9}$ against S. aureus SA113 as well its cell wall mutants. (A) S. aureus SA113 cell wall mutants were used to analyze charge-dependent antimicrobial effects of $HD5_{1-9}$. S. aureus mutant ΔdltA lacks D-Alanine leading to a more negative charge of the peptidoglycan layer. Similar characteristics possess the mutant ΔmprF missing L-Lysin causing a negative charge of the cell membrane. The S. aureus mutant ΔtarH contains additional teichoic acid resulting in a strengthening of the peptidoglycan layer. (B) The minimal inhibition concentration (MIC) of $HD5_{1-9}$ was determined against S. aureus SA113 and mutants with different peptide concentrations due to the optical density after 18 h. Results from two independent experiments with +/−SEM are represented.

Figure 18:
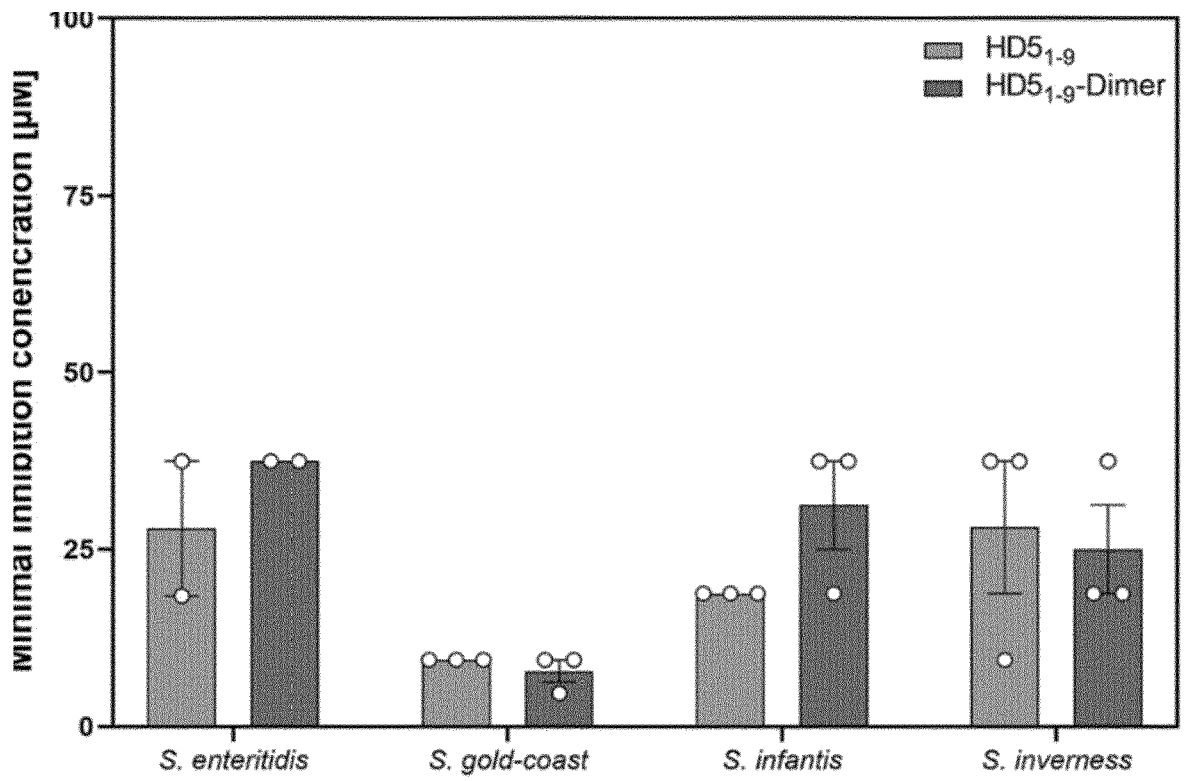

FIG. 18: Antimicrobial effects of $HD5_{1-9}$ differentiate compared to the dimer form against Gram-negative bacteria. The minimal inhibition concentration (MIC) of $HD5_{1-9}$ and $HD5_{1-9}$-dimer was determined against different Salmonella species with different peptide concentrations due to the optical density after 18 h. Results from at least two independent experiments with Mean+/−SEM are represented.

Figure 19:
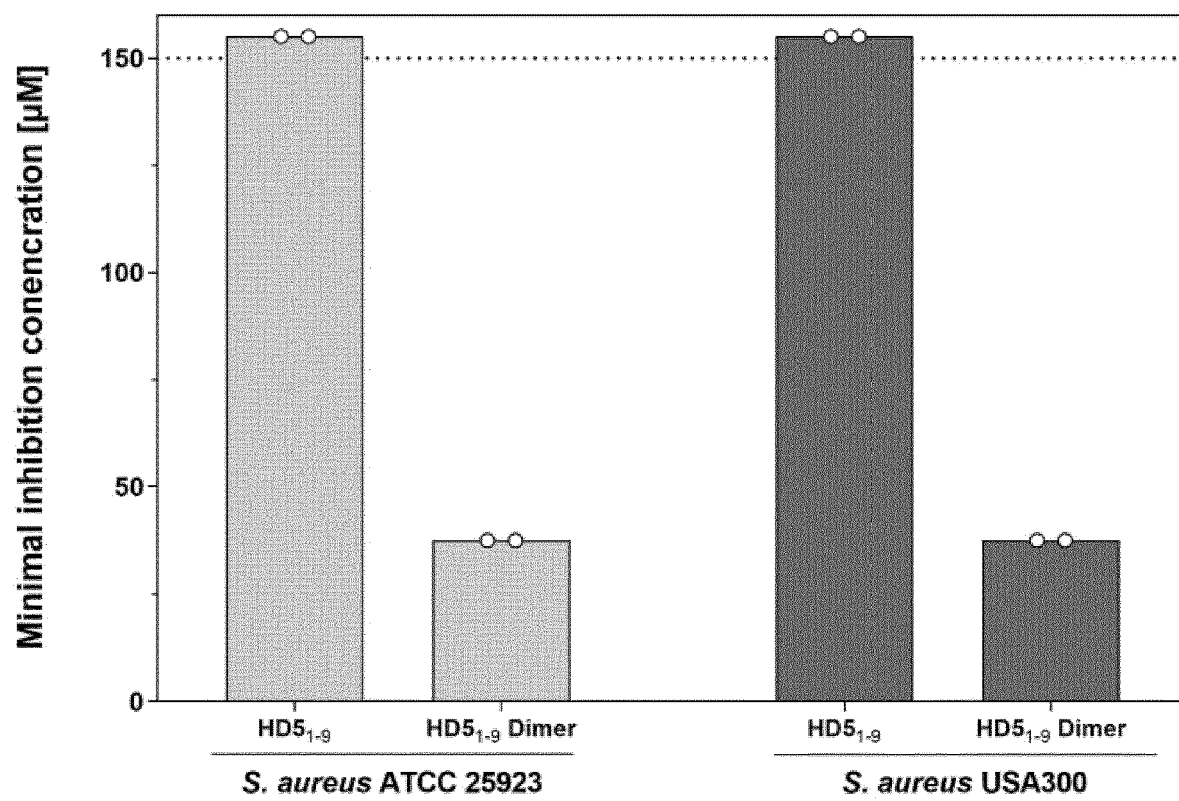

FIG. 19: Antimicrobial effects of $HD5_{1-9}$ differentiate compared to the dimer form against Gram-positive bacteria. The minimal inhibition concentration (MIC) of $HD5_{1-9}$ and $HD5_{1-9}$-dimer was determined against S. aureus ATCC25923 and the clinical isolate S. aureus USA300 with different peptide concentrations due to the optical density after 18 h. Results from two independent experiments with +/−SEM are represented.

Figure 20:
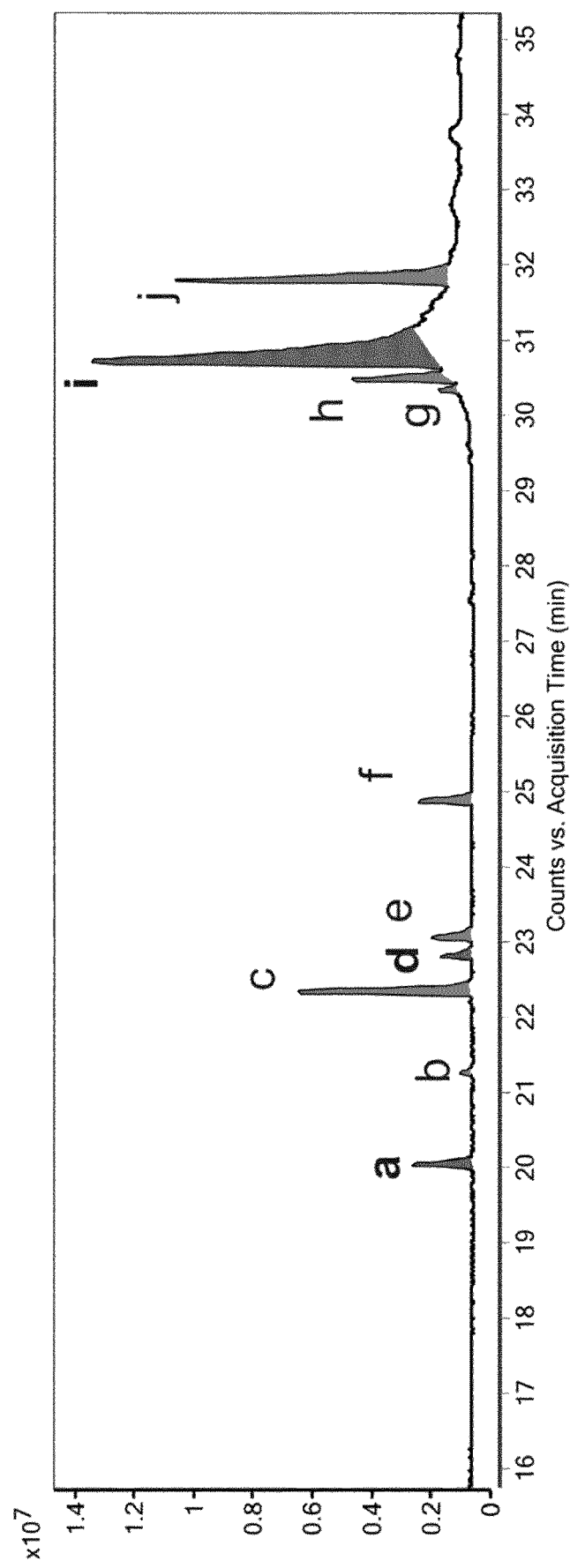

FIG. 20: Reduced HNP-4 is digested by trypsin. (A) Displays an overview of the chromatogram from an incubation of reduced HNP-4 with trypsin after reduction with 2 mM TCEP. All detectable fragments were marked in red or grey (a-j) and listed due to their retention time. The full length peptide is marked as (i) and the fragment $HNP-4_{1-11}$ (d).

FIG. 21: HNP4-derivates display a high antimicrobial activity against commensal and pathogenic bacteria We analyzed the antimicrobial potential of the identified fragment and its modified version against commensal and pathogenic bacteria using a RDA. Showing a heat map, an inhibition zone greater than 5 mm was determined as highly active, between 2.5 and 5 mm as low active, while a diameter of 2.5 mm (diameter of the punched well) was marked as not active. The heat map is based on at least three independent experiments.

Figure 22A:
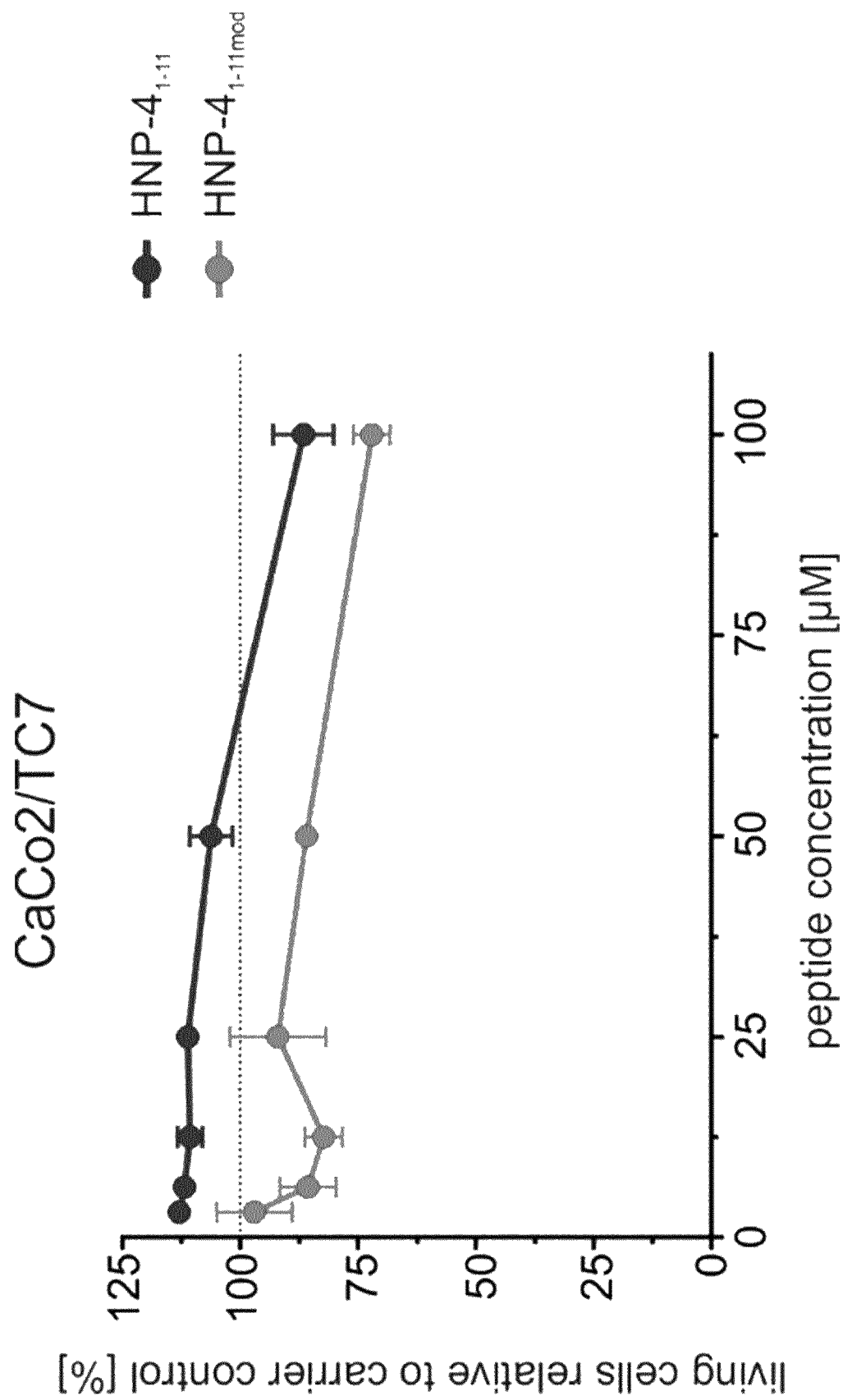

FIG. 22: HNP-41-11 and HNP-41-11mod show only minor cytotoxic and hemolytic activity at high concentrations. We investigated the cytotoxic activity of $HNP-4_{1-11}$ and $HNP-4_{1-11mod}$ against (A) CaCo2/TC7 or (B) HT29 MTX E 29 cells. We seeded 1500 cells per well and treated them after 24 hours with different peptide concentrations. Living cells were determined after 96 hours treatment using a CellTiter Glo2.0 assay. (C) Hemolytic activity on human erythrocytes of the peptides compared to 0.1% Triton-X treatment.

Material and Methods
Bacterial Strains

A. baumannii 4-MRGN, K. pneumoniae 4-MRGN, P. aeruginosa ATCC27853, E. faecium 475747, B. longum, L. fermentum, L. salivarius and S. salivarius salivarius were obtained as clinical isolates from the Robert-Bosch-Hospital (Stuttgart, Germany). Akkermansia muciniphila, B. subtilis 168trpC and S. aureus USA300 were received from the Institut für Mikrobiologie und Infektionsmedizin (Tübingen, Germany). B. adolescentis Ni3,29c, B. breve were provided by Ardeypharm. B. vulgatus DSM1447 was obtained from DSMZ and L. rhamnosus were provided by InfektoPharm (Heppenheim, Germany). Escherichia coli ATCC 25922 was obtained from Deutsche Sammlung von Mikroorganismen und Zellkulturen GmbH (Bonn, Germany). Clinical isolate of Salmonella species as well as Staphylococcus aureus USA300, Staphylococcus aureus ATCC 25923, Staphylococcus aureus SA133 and its mutants were provided by the Institute of Medical Microbiology and Hygiene Tübingen, Germany. Escherichia coli BW25113 as well as its mutants were obtained from the Interfaculty Institute for Microbiology and Infection Medicine, Tübingen, Germany. Peptides For all experiments oxidized peptides HD-5 and HD-6 (Peptide Institute, Osaka, Japan) were used. All fragments, i.e. $HD-5_{1-9}$ and $HNP-4_{1-11}$, $HD-5_{1-13}$, $HD-5_{1-28}$, $HD-5_{7-32}$, $HD-5_{10-32}$, $HD-5_{14-32}$, $HD-5_{10-27}$ and $HD-5_{26-32}$ (all peptides of the invention), were synthesized by EMC microcollections GmbH (Tübingen, Germany). All peptides were dissolved in 0.01% acetic acid (HAc) in similar concentrations.

The following sequences (peptides according to the invention) were tested (N→C-terminus):

$HD-5_{1-9}$: (SEQ ID No. 1)
ATCYCRTGR $HD-5_{1-9rev}$: (SEQ ID No. 2)
RGTRCYCTA $HD-5_{1-9mod}$: (SEQ ID No. 5)
Ac-atcycrtGr-NH$_2$ $HNP-4_{1-11}$: (SEQ ID No. 3)
VCSCRLVFCRR $HNP-4_{1-11rev}$: (SEQ ID No. 4)
RRCFVLRCSCV $HNP-4_{1-11mod}$: (SEQ ID NO. 6)
Ac-vcscrlvfcrr-NH$_2$ Collection of Duodenal Fluid During Gastroscopy.

The human duodenal fluid was collected during a routine gastroscopy from three healthy individuals. The duodenum was washed with 0.9% NaCl solution, which was recollected. Patients gave their written and informed consent after they were informed. The sample collection had been previously approved by the Ethical Committee of the University Hospital of Tuebingen, Germany.

Screening for Fragments of HD-5 and HD-6 Using LC/MS 2.5 µg of HD-5 or HD-6 were incubated in 50 mM $NH_4HCO_3$ buffer (pH 8.0) (Fluka) with 2 mM tris(2-carboxyethyl) phosphine for 15 minutes at 37° C. Afterwards human duodenal fluid was added and incubated for additional 30 minutes at 37° C. At last, formic acid and acetonitrile was added in a final concentration of 0.5% and 10%, respectively, and analyzed the samples by mass spectrometry. Mass spectrometry was performed as a LC/MS system using an Agilent 1200 series HPLC with an Agilent Advanced Bio Peptide Map (2.1×150 mm, 2.7 µm) column with a flow of 0.4 ml/min at 55° C. column temperature and a 6540 UHD Q-TOF LC/MS system (Agilent) for mass analysis. The samples were separated by a gradient of acetonitrile in 0.1% formic acid. The gradient started at 2% acetonitrile for 4 minutes and then increased during 35 minutes to 45%. Mass spectrometric analyses were performed in single MS mode from 100 to 3400 m/z with positive ion polarity and were analyzed by Agilent MassHunter Quantitative Analysis B 06.00 software.

Scanning-Electron-Microscopy

Scanning-Electron-Microscopy was performed as previously described. Briefly, Protein A coated beads (Spherotech Inc.) were incubated with reduced HD-6 (200 µg/ml) in 10 mM sodium phosphate buffer with 1% (w/v) TSB for 1.5 hours at 37° C. to allow net formation. We subsequently incubated the whole sample with duodenal fluid for additional 30 minutes at 37° C. As a control 0.01% acetic acid (HAc) was used. Beads were centrifuged and fixed in Karnovsky's reagent. The samples were washed with PBS and additional fixed with 1% $OsO_4$ in $H_2O$. Then, they were dehydrated to 100% ethanol and critical point dried from $CO_2$ and analyzed by scanning electron microscopy at the Max Planck Institute for Developmental Biology (Tuebingen, Germany).

Transmission Electron Microscopy

Transmission electron microcscopy experiments were performed as previously described[11]. $6 \times 10^8$ cfu E. coli MC1000 was incubated with 200 µg/ml of each peptide for 2 hours. Bacteria were fixed in Karnovsky's fixative, embedded in agarose, coagulated, cut in small blocks and fixed again in Karnovsky's solution. After post-fixation and embedding in glycid ether blocks were cut using an ultramicrotome. Sections (30 nm) were mounted on copper grids and analyzed using a Zeiss LIBRA 120 transmissions electron microscope.

Radial Diffusion Assay

Antimicrobial activity of all peptides was tested with a modified radial diffusion assay from Lehrer et al[12] Shortly described, log-phase bacteria grew (anaerobic bacteria with AnaeroGen, Oxoid in anaerobic jars) in liquid tryptic soy broth (TSB) (Becton Dickinson). After several wash steps in 10 mM sodium phosphate buffer pH 7.4, $4 \times 10^6$ cfu/ml was used per assay. To measure the antibacterial effect of the identified peptide fragments, the bacteria were incubated in 10 mM sodium phosphate (pH 7.4) containing 0.3 mg/ml TSB powder and 1% (w/v) low EEO-agarose (Applichem). Peptide fragments were then pipetted into punched wells and allowed to diffuse for 3 hours at 37° C. After that a nutrient rich gel with 6% TSB (w/v) and 1% agarose in 10 mM sodium phosphate buffer was poured on top of the first gel. After 24 hours the inhibition zones were measured. We used 0.01% acetic acid as a negative control, which did not show inhibition zones greater than the diameter of the punched well. All experiments were carried out at least three times.

Turbidity Broth Assay

The tested bacteria were incubated overnight in 1×TSB broth, centrifuged and washed with 10 mM sodium phosphate buffer containing 1% (w/v) TSB broth. $5 \times 10^5$ cfu/ml bacteria were mixed with different peptide concentrations in 10 mM sodium phosphate buffer with 1% (w/v) TSB (final volume 100 µl) and incubated for 2 hours at 37° C. Afterwards we added 100 µl 2×TSB broth and we measured the optical density at 600 nm (Spark 10M, Tecan, Austria). Bacterial growth was monitored for 12 hours, growing at 37° C. with shaking during the measurements each 30 minutes, except for Akkermansia muciniphila which were incubated at 37° C. in an anaerobic jar and growth was measured after 72 hours.

Bactericidal activity of the E. coli and S. aureus strains in the cell wall target experiments as well as the HD5 dimer experiments was assessed as described previously. Logphase bacteria were collected by centrifugation (2500 rpm, 10 min, 4 15° C.), washed twice with 10 mM sodium phosphate buffer containing 1% (w/v) TSB broth and the optical density at OD600 nm (OD600=0.1) was determined. Approximately $5 \times 10^5$ CFU/ml bacteria were incubated with serial peptide concentrations (1.17-150 µM) in a final volume of 100 µl in 10 mM sodium phosphate buffer containing 1% (w/v) TSB broth for 2 hours at 37° C. After incubation, 100 µl of 6% TSB (w/v) were added and absorbance was measured at 600 nm (Tecan, Switzerland) and monitored for 18 hours. Afterwards, 100 µl per well were plated on LB-plates to determine the numbers of viable bacteria microbiologically. Bactericidal activity is expressed as the LC99.9, the lowest concentration that killed ≥99.9% of bacteria. The experiment was repeated at least three times independently.

Cell Cytoxicity Assay

CaCo2/TC7 (X, X) and HT29 MTX E29 (X, X) were seed in a 96 well plate in 90 µl media (1500 cells/well) and incubated at 37° C. for 24 hours. Afterwards peptide treatment with different concentrations started (volume of 10 µl solved in 0.01% acetic acid) and cells were incubated for 96 hours. Untreated and 1% Triton-X treated cells were used as controls. After the incubation we added 100 µl of CellTiter Glo2.0 solution and started our measurement protocol. The measurement was carried out in a Spark 10M (Tecan), starting with 12 minutes continuously shaking followed by the luminescence measurement with an integration time from 1 second per well. Experiments were carried out in duplicates.

Hemolytic Assay

Hemolytic activity was measured after an existing protocol[13]. We obtained blood from two voluntary donors (sample collection had been previously approved by the Ethical Committee of the University Hospital of Tübingen, Germany) and 1 ml blood was washed with PBS two times. Afterwards we centrifuged the blood at 1000 g and performed a 1% (v/v) blood suspension in PBS. The blood suspension was incubated with different peptide concentrations (final concentration 0.5%) for one hour at 37° C. Then the samples were centrifuged at 1000 g for 10 minutes and the supernatant was collected and measured at 414 nm. The hemolytic activity was relative determined to the hemolytic activity of 0.1% Triton X-100. These experiments were carried out in duplicates.

In Vivo Microbiota Analysis

To assess proof of concept of a functional impact on microbiota composition, HD-$5_{1-9}$ was administered to 9 weeks old healthy chow fed male mice housed in groups of 3 per cage. Mice were acclimatized for 3 weeks prior to the experiment start and stratified into experimental groups based on average body weight per cage, ensuring equal weight distribution between groups. In more detail, wildtype C57BL/6J mice were treated by oral gavage for 7 days with 7.19 µg/mouse HD-$5_{1-9}$ administered in 100 µL PBS solution. Control mice were treated with equal volume PBS. Initially, a 7-day experiment was performed with 6 mice per group. Based on these results, a new study was designed, also including 6 mice per group, to study the temporal impact of gut microbial modulations. In this study, a 7 days wash period was included, after 1 week of oral gavage. Fresh feces samples were collected from individual mice at day 0, 7 and 14 (treated and control group n=6 in each) at 9 AM the same time body weight was measured. At day 14, mice were euthanized and the small intestine content was collected.

Bacterial DNA was extracted from snap-frozen feces collected at day 0, 7 and 14, and content of small intestine at necropsy by the NuceloSpin 96 soil kit (Macherey-Nagel) following the manufacturer's instructions. BGI, Europe performed the subsequent library preparation and DNA sequencing using in-house standard operating procedures. In brief, 30 ng of bacterial DNA per sample was PCR amplified using the primers: 515F: GTGCCAGCMGCCGCGGTAA (SEQ ID No. 7), 806R: GGACTACHVGGGTWTCTAAT (SEQ ID No. 8) with Illumina adapters targeting the V4 16S rDNA region. PCR products were then purified with AmpureXP beads (AGENCOURT) to remove unspecific products. The average molecule length was determined by Agilent 2100 bioanalyzer (Agilent DNA 1000 Reagents). DNA quantification was evaluated by real-time quantitive PCR (EvaGreen™) before pair end sequencing on a HiSeq2500 system.

Processing and quality control of reads was performed using the R package DADA2, version $1.4.0^{14}$ and forward and reverse primers were trimmed off from reads. Next, all reads containing remaining uncalled bases or more than two expected errors were removed. Afterward, the parameters of the DADA2 error model were learned from a random subset of 1 million reads. This error model was then used to denoise all sequences; i.e., to infer the ASVs. Denoised reads (ASVs) were then merged and read pairs with one or more conflicting bases between the forward and reverse read were removed. ASVs shorter than 251 and longer than 254 bases were discarded. Chimeric sequences were then detected and removed using the function "removeBimeraDenovo." Finally, reads (ASVs) were classified from the kingdom to the genus level using the Silva reference 16S rRNA gene database, version 132 resulting in the construction of an ASV table with read counts of all ASVs in all samples.

All animal protocols were conducted according to guidelines set out by the Laval University Animal Care and Handling Committee. C57BL/6J male mice (Jackson Laboratories, Bar Harbor, ME) were housed in a pathogen-free, temperature-controlled environment under a 12:12 hour light-dark cycle and fed ad libitum standard rodent chow diet (Harlan Teklad T-2018) for the 5 weeks of accommodation in our vivarium (3 weeks of acclimatization and 2 weeks of experimental protocol).

Statistical Analysis

Apart from microbiome analyses, all data were analyzed with GraphPad Prism 7. Values of p<0.05 were considered as statistically significant. All results are depicted as mean and their ± standard deviation, with their standard error of the mean or as 80% confidence interval, as indicated in the figure legend. Bioinformatical analysis was carried out using R Studio (R version 3.4.2 and R Studio version 1.0.136) and packages phyloseq $1.22.3^{15}$, metagenomeSeq $1.20.0^{16}$, vegan $2.4$-$4^{17}$, lme4 1.1-15, and ggplot2 $2.2.1^{18}$. For our mice studies we used cage-adjusted p-values.

Software

For the in silico digest analysis the ExPASy PeptideMass tool from the SIB Bioinformatics Resource Portal (https://web.expasy.org/peptide_mass/) was used.

Results

Natural human duodenal fluid digests HD-5, while nanonet forming HD-6 is protease resistant Since Paneth cell defensins can be reduced by the natural occurring thioredoxin system, their susceptibility to a proteolytic digest was investigated. Before the experimental procedure was started, the possible fragmentation of HD-5 and HD-6 by intestinal proteases was investigated. The PeptideMass module of ExPASy (SIB Bioinformatics Resource Portal) was accordingly used to perform in silico digests of HD-5 and HD-6 with trypsin, chymotrypsin or a combination of both and allowed up to five missed cleavages. The possible fragments are listed in table 1 below on basis of their individual mass.

TABLE 1

In silico (normal letters) and ex vivo reality after duodenal mucus incubation (in bold letters) digest of Paneth cell HD-5 and HD-6 with trypsin or chymotrypsin or both in combination, maximum of 5 missed cleavages and fragments bigger than 500 Da. Determination of the different sequences with the ExPASy PeptideMass module. Fragments which can be identified with mass spectrometry after incubation of the human peptides with human duodenal mucus are bold. The first line in the table designates the two full-length peptides, which could be identified too.

| SEQ ID No. | position | missed cleavages | sequence |
|---|---|---|---|
| | HD-5 | | |
| 9 | 1-32 | 5 | ATCYCRTGRCATRESLSGVCEISGRLYRLCCR |
| 10 | 1-29 | 4 | ATCYCRTGRCATRESLSGVCEISGRLYRL |
| 11 | 5-32 | 4 | CRTGRCATRESLSGVCEISGRLYRLCCR |
| 12 | 1-28 | 4 | ATCYCRTGRCATRESLSGVCEISGRLYR |
| 13 | 1-27 | 3 | ATCYCRTGRCATRESLSGVCEISGRLY |
| 14 | 7-32 | 4 | TGRCATRESLSGVCEISGRLYRLCCR |
| 15 | 1-26 | 2 | ATCYCRTGRCATRESLSGVCEISGRL |
| 16 | 5-29 | 3 | CRTGRCATRESLSGVCEISGRLYRL |
| 17 | 1-25 | 3 | ATCYCRTGRCATRESLSGVCEISGR |
| 18 | 5-28 | 5 | CRTGRCATRESLSGVCEISGRLYR |
| 19 | 10-32 | 3 | CATRESLSGVCEISGRLYRLCCR |
| 20 | 5-27 | 2 | CRTGRCATRESLSGVCEISGRLY |

TABLE 1-continued

In silico (normal letters) and ex vivo reality after duodenal mucus incubation (in bold letters) digest of Paneth cell HD-5 and HD-6 with trypsin or chymotrypsin or both in combination, maximum of 5 missed cleavages and fragments bigger than 500 Da. Determination of the different sequences with the ExPASy PeptideMass module. Fragments which can be identified with mass spectrometry after incubation of the human peptides with human duodenal mucus are bold. The first line in the table designates the two full-length peptides, which could be identified too.

| SEQ ID No. | position | missed cleavages | sequence |
|---|---|---|---|
| 21 | 7-28 | 3 | TGRCATRESLSGVCEISGRLYR |
| 22 | 5-26 | 1 | CRTGRCATRESLSGVCEISGRL |
| 23 | 7-27 | 3 | TGRCATRESLSGVCEISGRLY |
| 24 | 5-25 | 3 | CRTGRCATRESLSGVCEISGR |
| 25 | 14-32 | 2 | ESLSGVCEISGRLYRLCCR |
| 26 | 10-28 | 2 | CATRESLSGVCEISGRLYR |
| 27 | 7-25 | 2 | TGRCATRESLSGVCEISGR |
| 28 | 10-27 | 2 | CATRESLSGVCEISGRLY |
| 29 | 17-32 | 3 | SGVCEISGRLYRLCCR |
| 30 | 1-16 | 1 | ATCYCRTGRCATRESL |
| 31 | 14-28 | 1 | ESLSGVCEISGRLYR |
| 32 | 10-25 | 1 | CATRESLSGVCEISGR |
| 33 | 14-27 | 1 | ESLSGVCEISGRLY |
| 34 | 1-13 | 2 | ATCYCRTGRCATR |
| 35 | 17-29 | 2 | SGVCEISGRLYRL |
| 36 | 5-16 | 0 | CRTGRCATRESL |
| 37 | 14-25 | 0 | ESLSGVCEISGR |
| 38 | 17-27 | 1 | SGVCEISGRLY |
| 1 | 1-9 | 1 | ATCYCRTGR |
| 39 | 5-13 | 2 | CRTGRCATR |
| 40 | 17-26 | 0 | SGVCEISGRL |
| 41 | 26-32 | 1 | LYRLCCR |
| 42 | 27-32 | 2 | YRLCCR |
| 43 | 7-13 | 1 | TGRCATR |
| 44 | 1-6 | 0 | ATCYCR |
| 45 | 28-32 | 1 | RLCCR |
| 46 | 5-9 | 1 | CRTGR |
| | HD-6 | | |
| 47 | 1-32 | 3 | AFTCHCRRSCYSTEYSYGTCTVMGINHRFCCL |
| 48 | 3-32 | 5 | TCHCRRSCYSTEYSYGTCTVMGINHRFCCL |
| 49 | 1-29 | 5 | AFTCHCRRSCYSTEYSYGTCTVMGINHRF |
| 50 | 1-28 | 2 | AFTCHCRRSCYSTEYSYGTCTVMGINHR |
| 51 | 3-29 | 4 | TCHCRRSCYSTEYSYGTCTVMGINHRF |
| 52 | 3-28 | 5 | TCHCRRSCYSTEYSYGTCTVMGINHR |

TABLE 1-continued

In silico (normal letters) and ex vivo reality after duodenal mucus incubation (in bold letters) digest of Paneth cell HD-5 and HD-6 with trypsin or chymotrypsin or both in combination, maximum of 5 missed cleavages and fragments bigger than 500 Da. Determination of the different sequences with the ExPASy PeptideMass module. Fragments which can be identified with mass spectrometry after incubation of the human peptides with human duodenal mucus are bold. The first line in the table designates the two full-length peptides, which could be identified too.

| SEQ ID No. | position | missed cleavages | sequence |
|---|---|---|---|
| 53 | 8-32 | 2 | RSCYSTEYSYGTCTVMGINHRFCCL |
| 54 | 9-32 | 1 | SCYSTEYSYGTCTVMGINHRFCCL |
| 55 | 1-23 | 4 | AFTCHCRRSCYSTEYSYGTCTVM |
| 56 | 8-29 | 5 | RSCYSTEYSYGTCTVMGINHRF |
| 57 | 3-23 | 3 | TCHCRRSCYSTEYSYGTCTVM |
| 58 | 8-28 | 1 | RSCYSTEYSYGTCTVMGINHR |
| 59 | 9-29 | 4 | SCYSTEYSYGTCTVMGINHRF |
| 60 | 12-32 | 4 | STEYSYGTCTVMGINHRFCCL |
| 61 | 9-28 | 0 | SCYSTEYSYGTCTVMGINHR |
| 62 | 1-17 | 3 | AFTCHCRRSCYSTEYSY |
| 63 | 12-29 | 3 | STEYSYGTCTVMGINHRF |
| 64 | 12-28 | 2 | STEYSYGTCTVMGINHR |
| 65 | 16-32 | 3 | SYGTCTVMGINHRFCCL |
| 66 | 3-17 | 2 | TCHCRRSCYSTEYSY |
| 67 | 1-15 | 2 | AFTCHCRRSCYSTEY |
| 68 | 18-32 | 2 | GTCTVMGINHRFCCL |
| 69 | 3-15 | 1 | TCHCRRSCYSTEY |
| 70 | 16-29 | 2 | SYGTCTVMGINHRF |
| 71 | 16-28 | 1 | SYGTCTVMGINHR |
| 72 | 1-11 | 1 | AFTCHCRRSCY |
| 73 | 12-23 | 2 | STEYSYGTCTVM |
| 74 | 18-29 | 1 | GTCTVMGINHRF |
| 75 | 8-17 | 3 | RSCYSTEYSY |
| 76 | 18-28 | 0 | GTCTVMGINHR |
| 77 | 3-11 | 2 | TCHCRRSCY |
| 78 | 9-17 | 2 | SCYSTEYSY |
| 79 | 24-32 | 1 | GINHRFCCL |
| 80 | 8-15 | 2 | RSCYSTEY |
| 81 | 1-8 | 2 | AFTCHCRR |
| 82 | 16-23 | 1 | SYGTCTVM |
| 83 | 9-15 | 1 | SCYSTEY |
| 84 | 1-7 | 0 | AFTCHCR |
| 85 | 3-8 | 1 | TCHCRR |
| 86 | 12-17 | 1 | STEYSY |

TABLE 1-continued

In silico (normal letters) and ex vivo reality after duodenal mucus incubation (in bold letters) digest of Paneth cell HD-5 and HD-6 with trypsin or chymotrypsin or both in combination, maximum of 5 missed cleavages and fragments bigger than 500 Da. Determination of the different sequences with the ExPASy PeptideMass module. Fragments which can be identified with mass spectrometry after incubation of the human peptides with human duodenal mucus are bold. The first line in the table designates the two full-length peptides, which could be identified too.

| SEQ ID No. | position | missed cleavages | sequence |
|---|---|---|---|
| 87 | 24-29 | 0 | GINHRF |
| 88 | 3-7 | 0 | TCHCR |
| 89 | 18-23 | 0 | GTCTVM |
| 90 | 8-11 | 1 | RSCY |

Figure 1A:
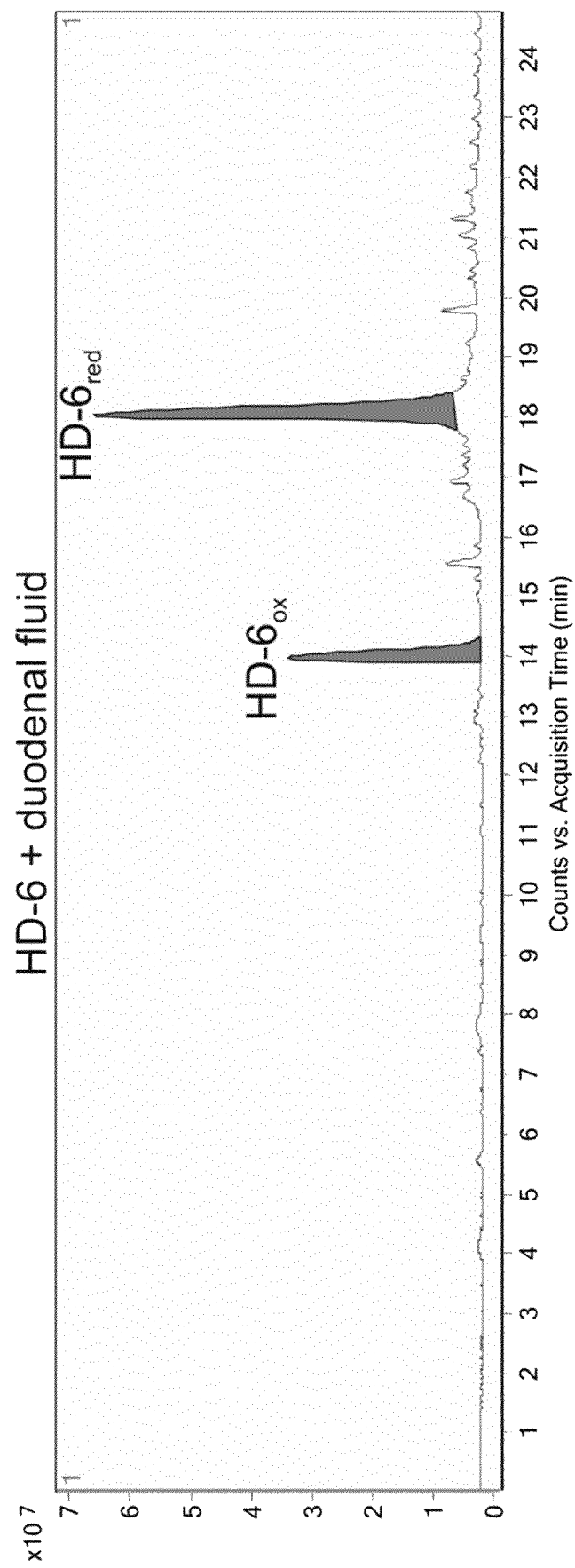
Figure 1B:
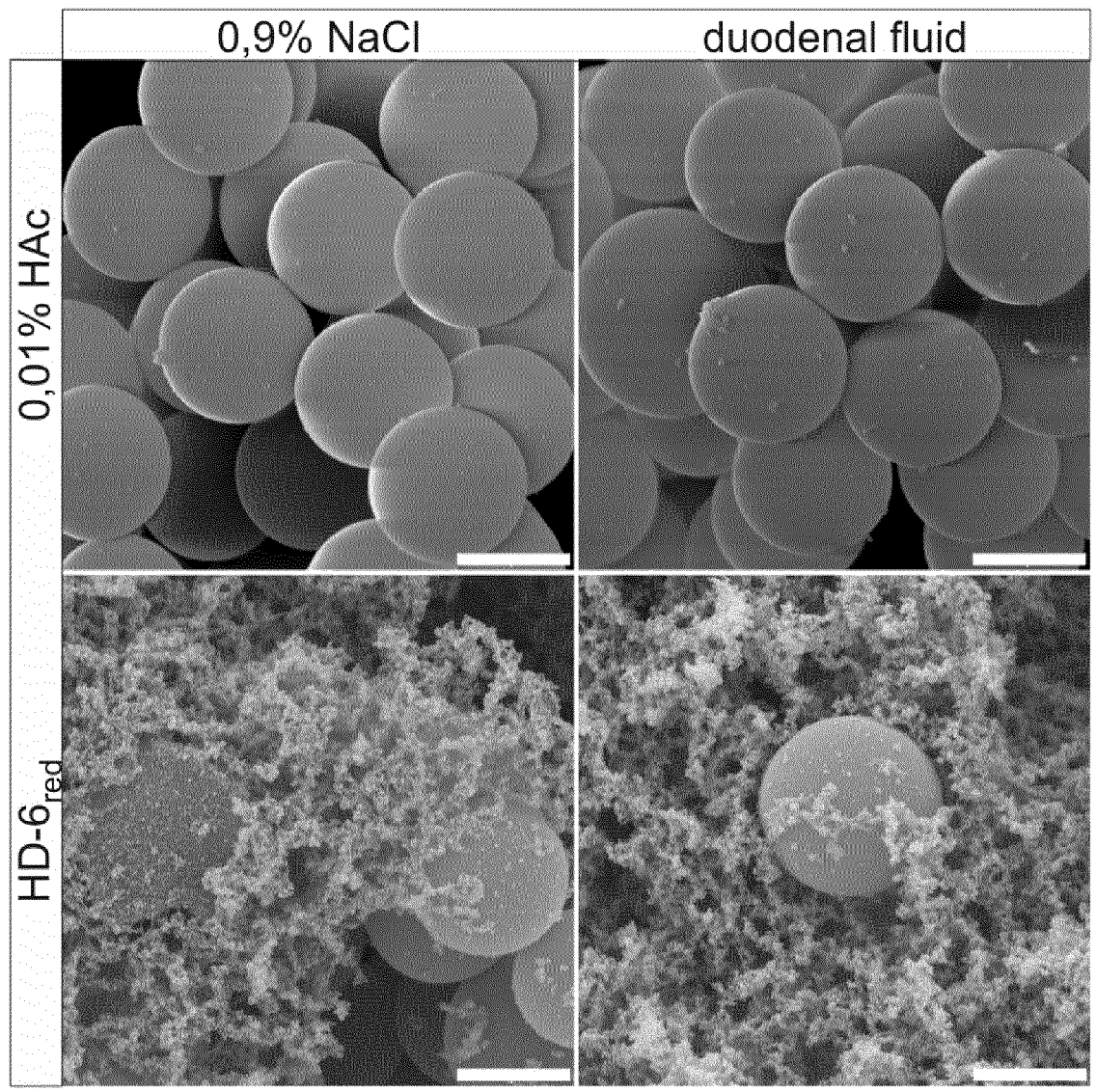

In theory, both Paneth cell defensins seemed to be susceptible to proteases while HD-6 showed a tendency of more fragmentation as compared to HD-5 (Table 1). In a second step, the reducing agent tris(2-carboxyethyl) phosphine (TCEP) was used to reduce HD-5 or HD-6 and the peptides were challenged to natural occurring duodenal fluid, which is known to be proteolytically active. After performing a mass-spectrometric analysis a partly reduction with 2 mM TCEP for HD-6 was found, which is consistent with previous published work. Beside the two full-length forms HD-6$_{ox}$ (expected: 3705.49 Da) and HD-6$_{red}$ (3711.54 Da), surprisingly no other fragments were identified, identifiable by mass-to-charge-ratio (m/z) signals indicating 2-, 3-, 4-, 5-, 6-fold protonated ions. This surprising observation demonstrates that HD-6$_{red}$ is protected against proteolytic digestion although the reason remains elusive, since proteolytic cleaving sites were bioinformatically predicted. It is known that both forms of HD-6 independent of its redox state (HD-6$_{ox}$ and HD-6$_{red}$) are able to form nanonets. Thus, it was hypothesized that net formation protects against protease degradation and thus might provide a mechanistic explanation for the observed peptide protection. To clarify if nanonet formation leads to a more stable structure, scanning electron microscopy from reduced HD-6 incubated with duodenal fluid was performed (FIG. 1). Consistent with this hypothesis, equal nanonets were observed independent of duodenal fluid incubation (FIG. 1B). Taken together, it appears that the nanonet formation at least contributes to prevent HD-6 from proteolytic digestion.

Figure 2A:
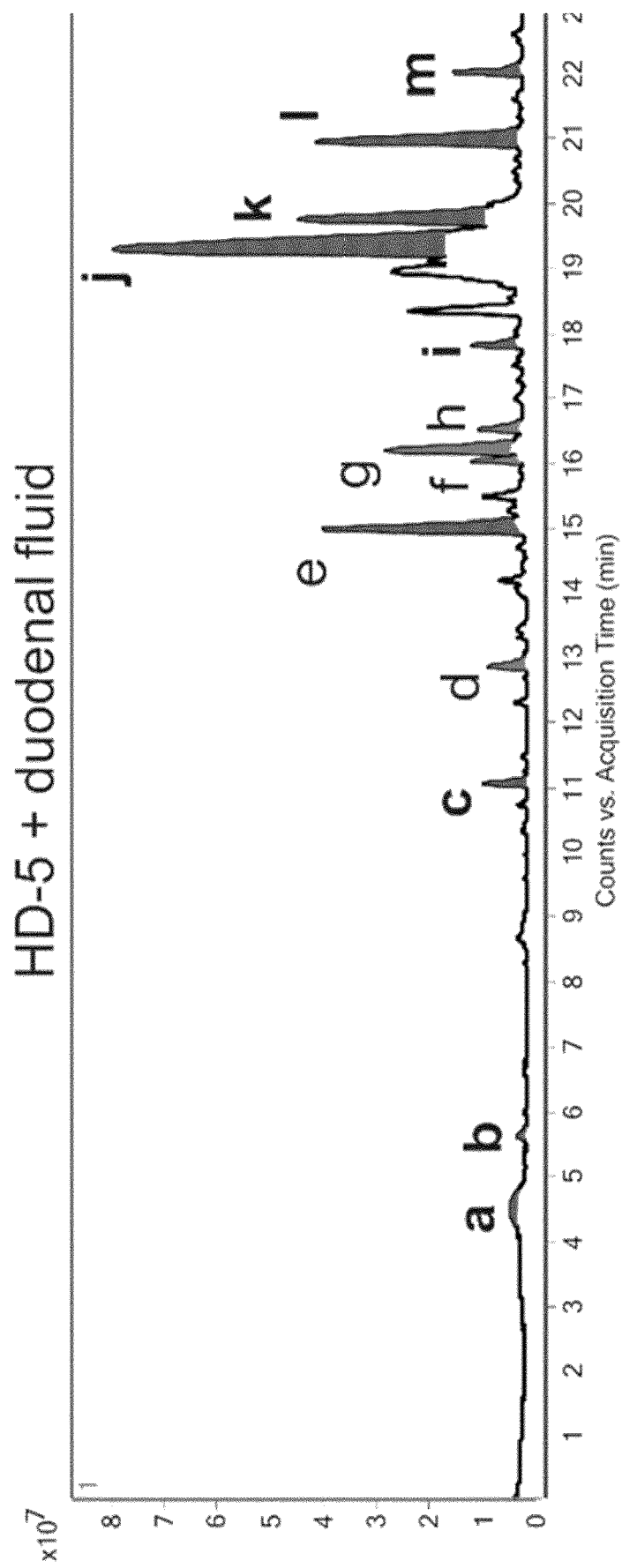
Figure 2B:
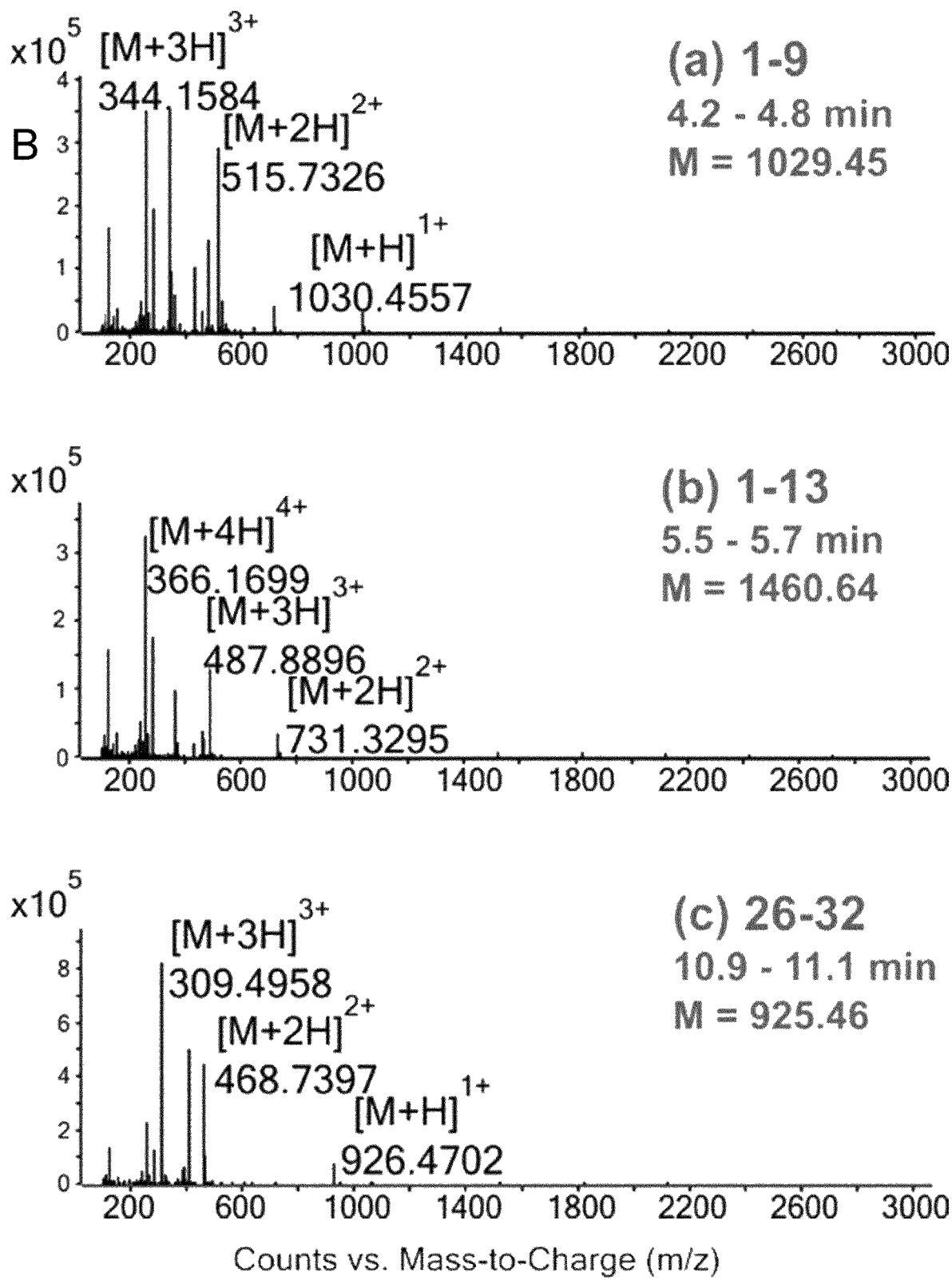

Next, the second and more abundant Paneth cell defensin, HD-5, was studied in an identical experimental setup. After incubation with 2 mM TCEP and duodenal fluid, HD-5$_{ox}$ was below limit of detection (LOD), whereas HD-5$_{red}$ was highly abundant. While HD-5 is not able to form nanonets, it was surprisingly observed that in contrast to HD-6, duodenal fluid had a differential effect on HD-5. Consistent with known protease cleaving sites, different fragments were identified which were not present before adding HD-5 (FIG. 2A, Table highlighted in bold letters). These fragments were analyzed and listed with their mass-to-charge ratios and the different observed protonated ions with their mass were shown for each fragment (FIG. 2B). The identified fragments were listed with their neutral mass and retention time, showing that the fragmentation of HD-5 with duodenal fluid led to abundant fragments derived from the entire peptide sequence. However, we still found detectable amounts of full length HD-5$_{red}$ suggesting that the proteolytic digestion was incomplete. It is known that Zn$^{2+}$ can protect HD-5$_{red}$ from proteolytic digestion, which was indeed confirmed in our setting (data not shown). In summary, it was shown that duodenal fluid surprisingly is affecting HD-5 and HD-6 differently and that changes of conditions in the local microenvironment have an impact on defensin fragmentation. Of note, HD-6 nanonet formation seems to protect against destruction of the reduced full length peptide and it is known that reduction of HD-6 unmasks antimicrobial activity. Therefore, reduction changes the activity of both Paneth cell defensins, but while HD-6 gains a direct antimicrobial activity, HD-5 is digested by intestinal proteases to form bioactive peptide fragments with potential bioactive antimicrobial activity.

HD-5 Fragments are Antimicrobial Active in Radial Diffusion Assays

Figure 3A:
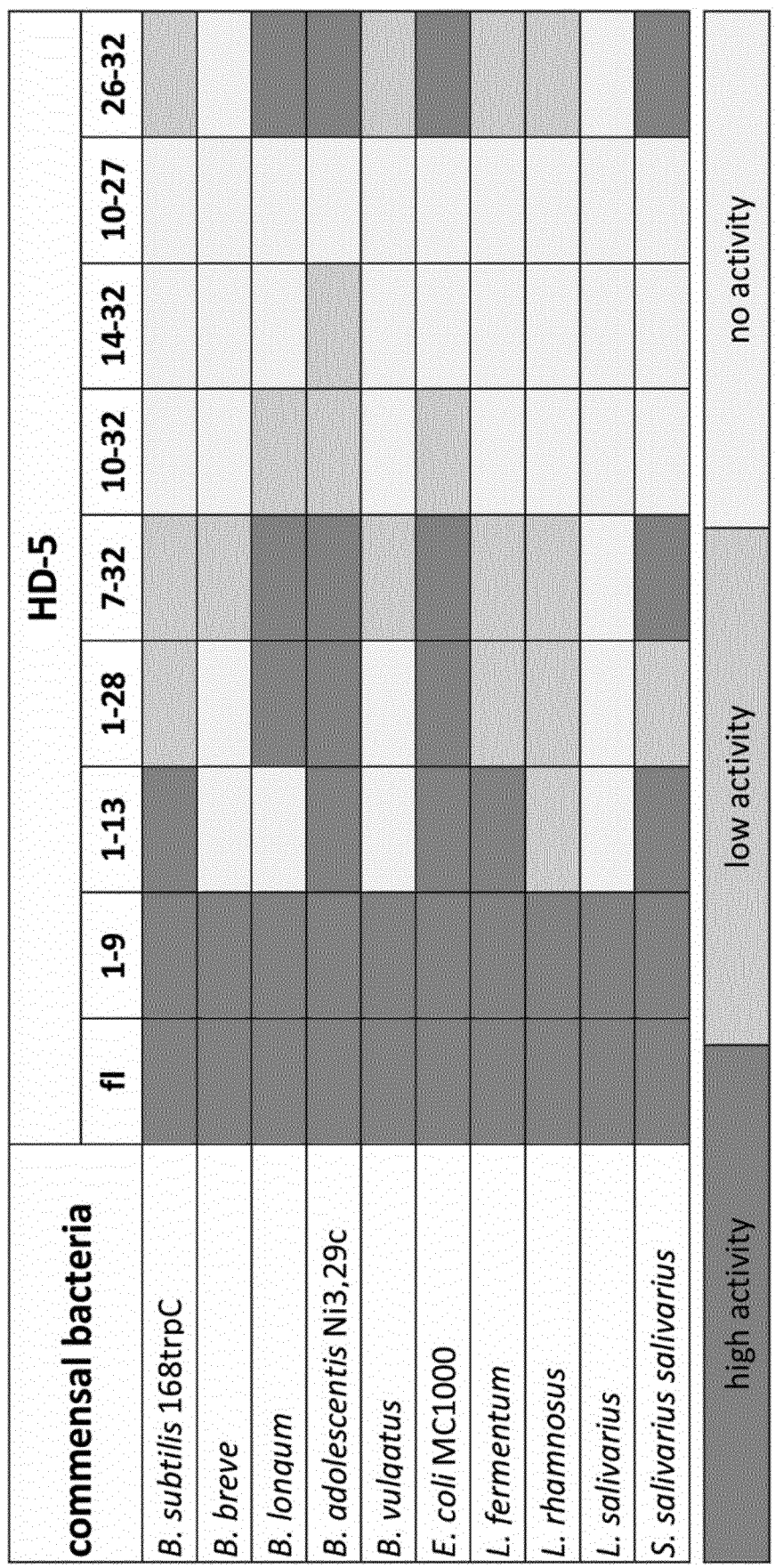
Figure 8B:
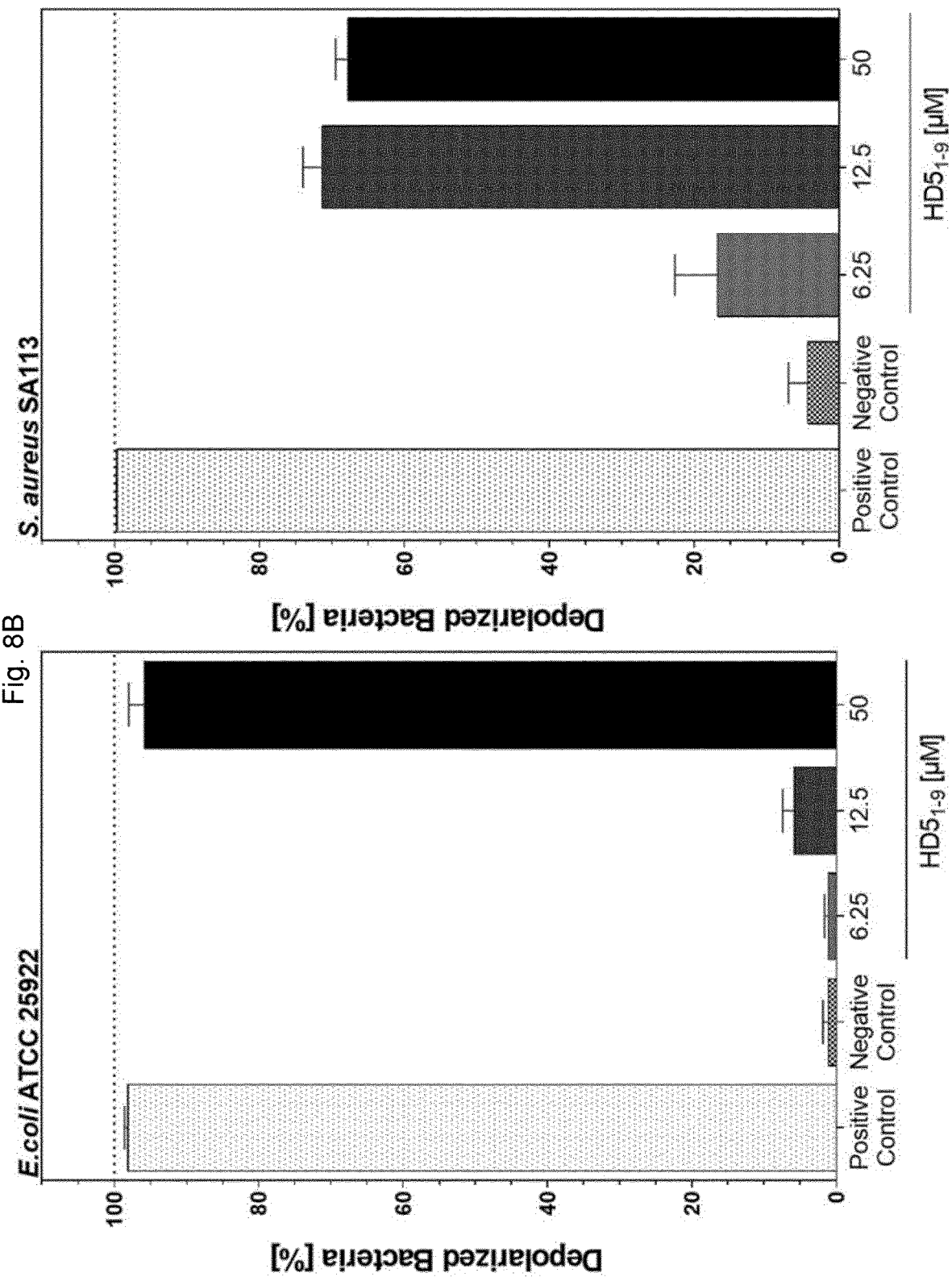
Figure 8C:
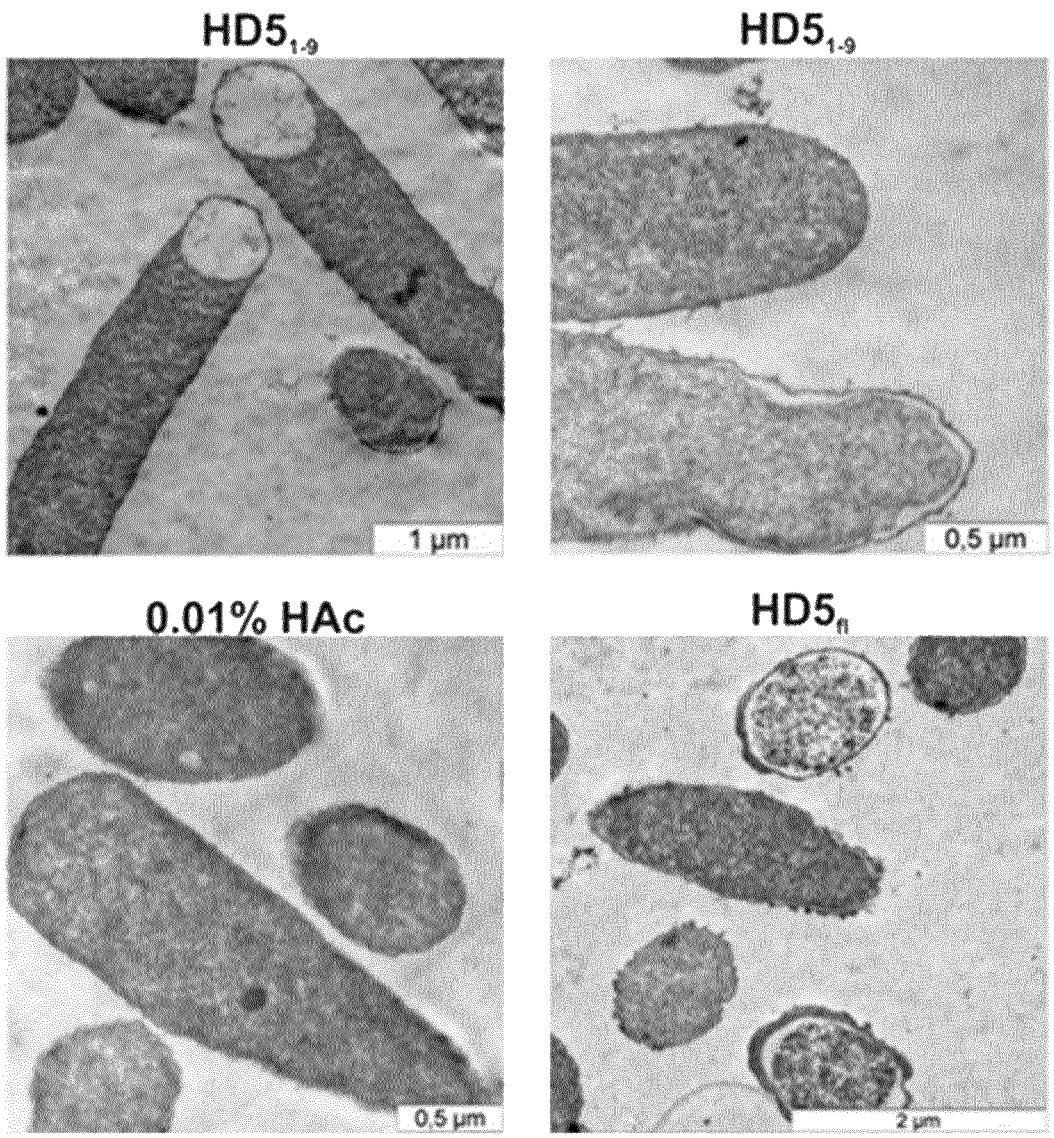

To test the antimicrobial activity from the HD-5 fragments, selected fragments were chemically synthesized to investigate antimicrobial functions in vitro (FIG. 2C). Several radial diffusion assays were performed with an amount of 4 μg of the different fragments and 2 μg of the full-length peptide against commensal gut and pathogenic bacteria. Interestingly and surprisingly, it was observed that most of HD-5 derived fragments to varying degree were antimicrobially active against commensal and pathogenic bacteria. Additionally, it was found that the different fragments exhibited distinct activity patterns (FIGS. 3A and B) against the applied bacteria strains. As expected the full length HD-5 displayed broad antimicrobial activity. Still and surprisingly HD-5$_{1-9}$ was identified as the most active peptide in terms of antimicrobial activity but also in terms of versatility since it was active against all tested bacteria. In contrast to HD-5$_{1-9}$, HD-5$_{10-27}$ did not exhibit measurable activity. Of note, HD-5$_{1-13}$, HD-5$_{1-28}$, HD-5$_{7-32}$ and HD-5$_{26-32}$ also exhibited antimicrobial properties, albeit to a lesser extent than HD-5$_{1-9}$. To further assess the resulting phenotype of peptide treated bacteria, E. coli MC1000 was incubated with all fragments and performed transmission electron microscopy (TEM) (FIG. 3C). It was observed that HD-5f treatment led to a detached inner membrane and small vesicular structures around the bacteria cell envelope (FIG. 8). Of interest, the bacteria surprisingly showed different typical phenotypes after incubation with the HD-5 different fragments which indicates discrepant modes of action. For HD-5$_{1-9}$ a detached inner membrane with additional big vacuole structures at one pole of the bacteria could be observed, while HD-5$_{1-13}$ and HD-5$_{1-28}$ treatment led to bigger aggregation inside the bacteria (FIG. 8). The findings indicate different kinds of bacterial phenotypes, and this variety suggests that minor sequence differences (e.g. HD-5$_{1-9}$ and HD-5$_{1-13}$) likely result in different mechanisms of host microbial interaction.

Of note and surprisingly, these observations showed that the antimicrobial activity of the different peptides did not apply to a certain group of bacteria. As an example the Bifidobacteria strains, *B. adolescentis* and *B. longum* were highly susceptible to the peptides, while *B. breve* was not. Collectively, the above-mentioned results demonstrate that a proteolytic digest of Paneth cell HD-5 leads to small, antimicrobial active fragments, which modulate commensal gut bacteria.

HD-5 Fragments and their Minimal Inhibitory Concentration Against Antibiotic-Resistant Bacteria In order to further investigate the potential of these fragments for a potential antibiotic therapeutic use, we measured the minimal inhibitory concentration (MIC) of our peptides against different antibiotic-resistant Gram-negative and Gram-positive bacterial strains. The results of the previous described RDA experiment indicated a promising antimicrobial activity against commensal and pathogenic bacteria. To gain a more detailed understanding of the antimicrobial abilities of the different HD-5 fragments, we performed turbidity broth assays to determine the MIC of these peptides. We determined the MIC as the concentration in which during all experiments no bacterial growth was detectable after 12 hours. Using this parameter we were able to detect antimicrobial activity of HD-5$_{1-9}$, HD-5$_{1-13}$, HD-5$_{1-28}$, HD-5$_{7-32}$ and HD-5$_{10-32}$ (see Table 2 below).

TABLE 2

MIC of HD-5 fragments in µM and µg/ml against pathogenic bacteria. Each experiment was carried out at least three times. The MIC was determined as the concentration without any bacterial growth in every experiment after 12 hours of incubation.

| | Bacteria | | | | | | | | | |
|---|---|---|---|---|---|---|---|---|---|---|
| | *A. baumannii* 4-MRGN | | *K. pneumoniae* 3-MRGN | | *P. aeruginosa* ATCC 27853 | | *E. faecium* 475747 | | *S. aureus* USA300 | |
| Peptides | MIC µM | MIC µg/ml | MIC µM | MIC µg/ml | MIC µM | MIC µg/ml | MIC µM | MIC µg/ml | µM | MIC, µg/ml |
| fl | 6.25 | 22.4 | — | — | 25 | 89.7 | 3,125 | 11.2 | 3,125 | 11.2 |
| 1-9 | 25 | 25.75 | — | — | 50 | 51.5 | 12.5 | 25.75 | 50 | 51.5 |
| 1-13 | >100 | >146 | — | — | >100 | >146 | — | — | — | — |
| 1-28 | >100 | >311 | — | — | >100 | >311 | 100 | 311 | — | — |
| 7-32 | 25 | 72.25 | — | — | 50 | 144.5 | 25 | 72.2 | — | — |
| 10-32 | >100 | >257 | — | — | >100 | >257 | 100 | 257 | — | — |
| 14-32 | — | — | — | — | >100 | >214.4 | — | — | — | — |
| 10-27 | — | — | — | — | — | — | — | — | — | — |
| 26-32 | — | — | — | — | — | — | — | — | — | — |

Figure 3B:
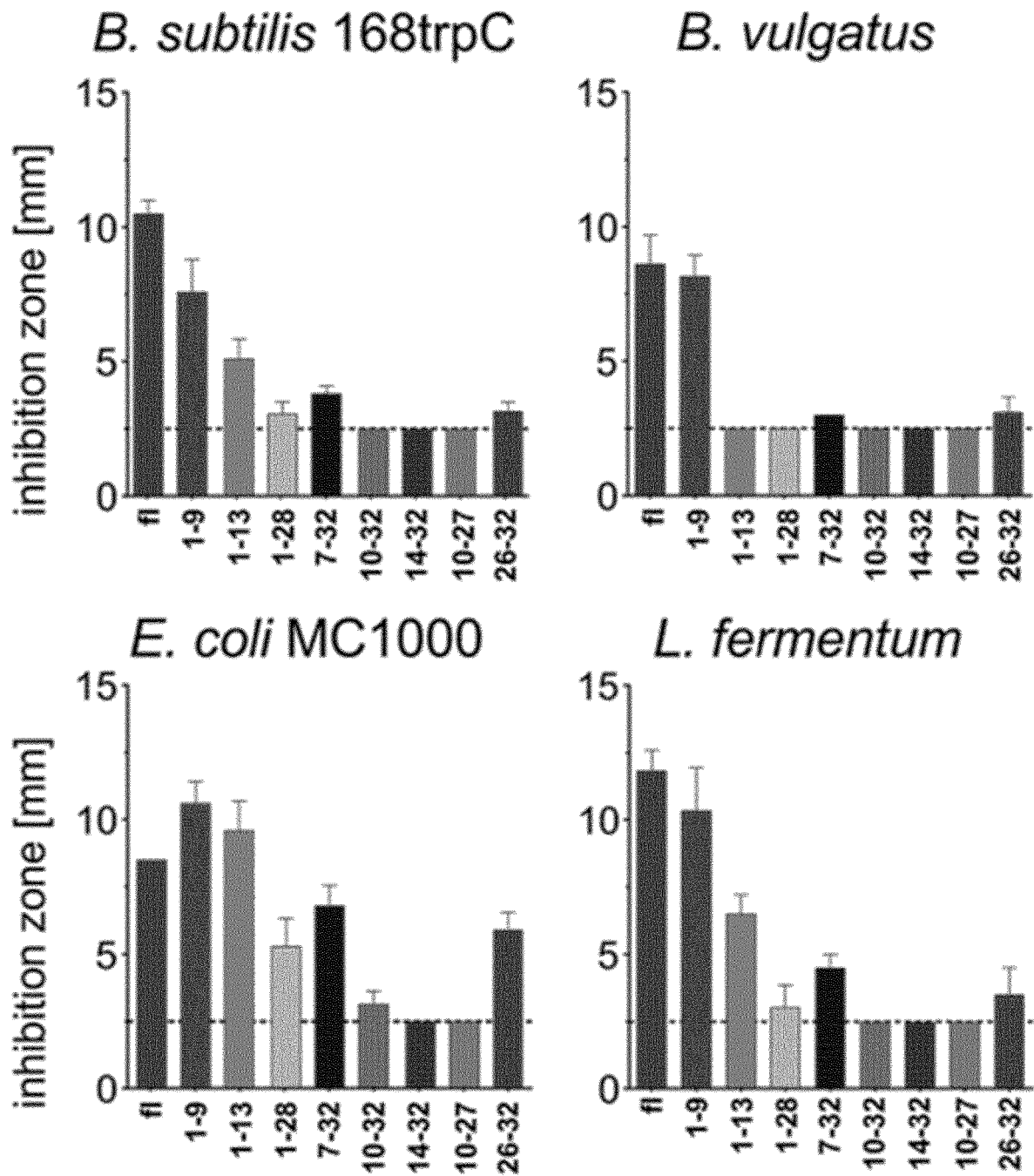
Figure 4B:
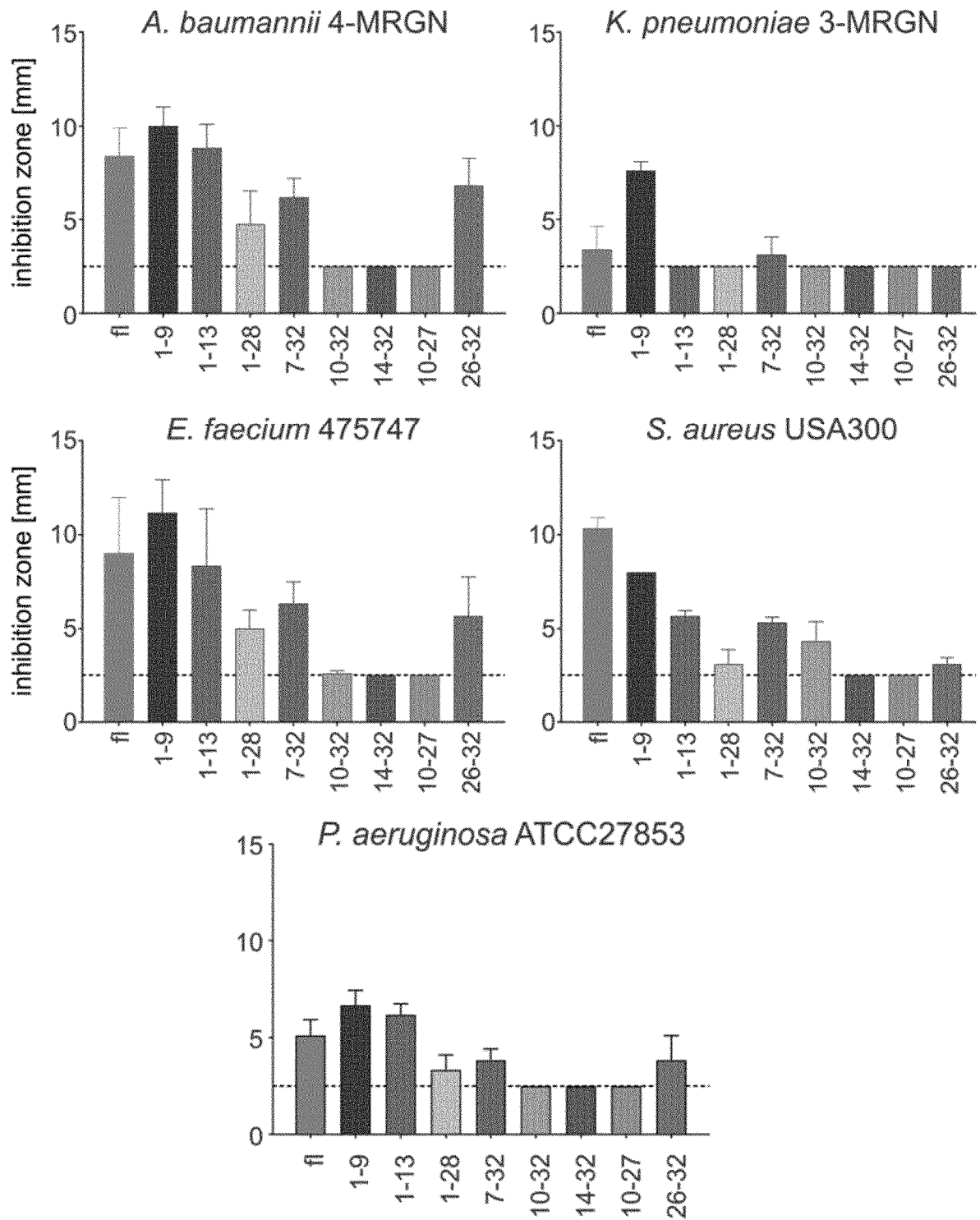

Next, the antimicrobial activity against pathogenic Gram-positive and Gram-negative bacteria (FIGS. 4A and B) was investigated. Here it was found, similar to the previous tested commensal bacteria, that the fragments were antimicrobially active but that the anti-microbial effect varied dramatically among the fragments. Surprisingly it was observed that HD-5$_{1-9}$, HD-5$_{1-13}$, HD-5$_{7-32}$ and HD-5, had a strong effect on the growth of every tested bacterium, while other fragments like HD-5$_{1-28}$, HD-5$_{10-32}$ and HD-5$_{26-32}$ were only minimally active or more selective in terms of different strains. In contrast, HD-5$_{14-32}$ and HD-5$_{10-27}$ were inactive against the tested bacteria under tested conditions. Of interest, the activity of HD-5$_{10-32}$ was limited to the two Gram-positive bacteria. Consistent with the findings described in the first experiment (FIG. 3), and in terms of their efficiency to kill commensals, HD-5$_{1-9}$ was active against all tested strains independent of Gram status, suggesting that this specific fragment is highly protective against bacterial barrier breach. In contrast, HD-5$_{1-13}$ potently regulated tested pathogenic bacteria, with the exception of *K. pneumoniae* 3-MRGN. Altogether these results indicate that a proteolytic digestion of Paneth-cell HD-5 but not HD-6 leads to the generation of a number of short and active antimicrobial fragments. The significance of this surprising finding may prove highly important because these fragments broaden the antimicrobial variance based on a single full length peptide depending on local environmental conditions.

Comparing the MIC (in µM) of these fragments with the full-length peptide, most of the defensin fragments surprisingly were as active, as the full length peptide. However, when the µg/ml MIC concentrations of the peptide fragments were compared, less was needed and—based on this concentration—especially HD-5$_{1-9}$ was more active than the full-length peptide. Of note, the observed MIC's were relatively high, except for HD-5$_{1-9}$ for *A. baumannii* 4-MRGN and *E. faecium* 475747, indicating that the role of antimicrobial active substances in the intestinal barrier is restricted to areas with high concentrations like the crypts. To clarify their functional capacity in vivo it was aimed to investigate their intestinal microbiome modulatory functions, in particular because Paneth cells are naturally located in the intestinal tract.

The antimicrobial activity was determined by the minimal inhibition concentration against Gram-negative and -positive bacteria as well as *Candida* species (Table 3) to investigate if the HD5$_{1-9}$ Mode of Action was disulfide bond and charge dependent. Thus, several variants of HD5$_{1-9}$ were synthesized including an exchange of cysteines with α-aminobutyric acid (Abu) and arginine substitutions with citrulline (Cit). Additionally, a reverse (RGTRCYCTA) and random (CTRATYCRG) amino acid structure of HD5$_{1-9}$ was tested. HD5$_{1-9}$ displayed strong bactericidal effects against *E. coli* BW 25113 whereas HD5$_{1-9}$ was less antimicrobial active against *S. enterica* serovar *Enteritidis*. Similar effects were observed for the reversed variant RGTRCYCTA against both Gram-negative bacteria.

The HD5$_{1-9}$ variants surprisingly lost their antimicrobial activity against tested Gram-negative bacteria if the sequence was random and when lacking either cysteine or arginine amino acids. For both *Staphylococcus* species no bactericidal effects were determined for HD5$_{1-9}$ or its variants. In contrast, HD5$_{1-9}$ displayed a strong bacterial activity against *E. faecalis*. However, cysteine and arginine substitutions of HD5$_{1-9}$ lead to a complete dissolving of bactericidal effects as well as random sequences RGTRCYCTA and CTRATYCRG. Unlike *E. faecalis*, neither HD5$_{1-9}$ nor its variants showed bactericidal effects against *E. faecium*. The antimicrobial activity of HD5$_{1-9}$ and variants was additionally investigated against two *Candida* species after 24 h. Inhibition of fungal growth could be observed for *C. tropicalis* displaying a low antimicrobial spectrum. Cysteine and arginine substitutions of HD5$_{1-9}$ had no effect on fungal growth inhibition. Similar effects were observed for *C. albicans* while HD5$_{1-9}$ and variants displayed no antimicrobial activity. In summary, results strongly emphasize the importance of present cysteine and arginine residues and an original amino acid structure of HD5$_{1-9}$ in order to induce antimicrobial effects.

TABLE 3 below shows the antimicrobial activity of HD51-9 against tested bacteria and *Candida* species. The minimal inhibition concentration (MIC) was determined of *E. coli* BW 25113, *S. enterica* serovar Enteritidis, *S. aureus* SA113, *S. epidermidis* Evans 1916, *E. faecalis* ATCC 19433, *E. faecium* ATCC 19434, *C. tropicalis* ATCC 4563 and *C. albicans* ATCC 10231 with different HD51-9 concentrations due to the optical density after 18 h or 24 h. Results from three independent experiments are presented:

| HD51-9 and variants | Gram negative | | Gram positive | | | | Candida | |
|---|---|---|---|---|---|---|---|---|
| | *E. coli* | *S. enterica* | *S. aureus* | *S. epidermidis* | *E. faecalis* | *E. faecium* | *C. tropicalis* | *C. albicans* |
| ATCYCRTGR SEQ ID NO 1 | XX | X | | | XX | | XX | |
| AT-Abu-YCRTGR SEQ ID NO 91 | | | | | | | | |
| ATCY-Abu-RTGR SEQ ID NO 92 | | | | | | | | |
| AT-Abu-Y-Abu-RTGR SEQ ID NO 93 | | | | | | | | |
| ATCYC-Cit-TGR SEQ ID NO 94 | | | | | | | | |
| ATCYCRTG-Cit SEQ ID NO 95 | | | | | | | | |
| ATCYC-Cit-TG-Cit SEQ ID NO 96 | | | | | | | | |
| RGTRCYCTA SEQ ID NO 97 | XX | X | | | | | | |
| CTRATYCRG SEQ ID NO 98 | | | | | | | | |

XX High activity

X Low activity

No activity

Table 4 below shows also the effect of HNP-4 fragments according to the invention. From this table can be seen that the HNP-4 peptide fragment according to the invention displays similar anti-microbial behavior as the HD-$5_{1\text{-}9}$ peptide.

TABLE 4

Table 4 below shows the antimicrobial activity of HD$5_{1\text{-}9}$, HD$5_{1\text{-}9;mod}$, HNP-$4_{1\text{-}11}$ and HNP-$4_{1\text{-}11;mod}$, against tested bacteria and *Candida albicans*. The minimal inhibition concentration (MIC) was determined of *A. baumannii* 4-MRGN, *A. baumannii* DSM 30007, *E. faecium* 475747, *E. faecium* DSM 20477, *K. pneumoniae* 3-MRGN, *K. pneumoniae* DSM 301404, *P. aeruginosa* 4-MRGN, *P. aeruginosa* ATCC 27853, *P. aeruginosa* PAO1, *P. aeruginosa* XPAT1, *P. aeruginosa* XPAT2, *S. aureus* USA300, *S. aureus* ATCC 25923, *S. entertidis*, *E. coli* BW 25113, *Y. enterocolitica*, and *C. albicans* 525L with different petide concentrations due to the optical density after 12 h. Results from three independent experiments are presented:

| MIC after 12 hours in μM | HD-$5_{1\text{-}9}$ | HD-$5_{1\text{-}9mod}$ |
|---|---|---|
| *A. baumannii* 4-MRGN | 25 | 12.5 |
| *A. baumannii* DSM 30007 | 100 | 25 |
| *E. faecium* 475747 | 12.5 | 3.125 |
| *E. faecium* DSM 20477 | 25 | 6.25 |
| *K. pneumoniae* 3-MRGN | >>> | >>> |
| *K. pneumoniae* DSM 30104 | >>> | >>> |
| *P. aeruginosa* 4-MRGN | 100 | 50 |
| *P. aeruginosa* ATCC 27853 | 50 | 12.5 |
| *P. aeruginosa* PAO1 | 50 | 50 |
| *P. aeruginosa* XPAT1 | >100 | >100 |
| *P. aeruginosa* XPAT2 | >100 | 100 |
| *S. aureus* USA300 | 50 | 12.5 |
| *S. aureus* ATCC 25923 | 50 | 12.5 |
| *S. entertidis* | 50 | >>> |
| *E. coli* | 25 | 25 |
| *Y. enterocolitica* | 50-100 | 50-100 |
| *C. albicans* 529L | >>> | >100 |

Figure 12A:
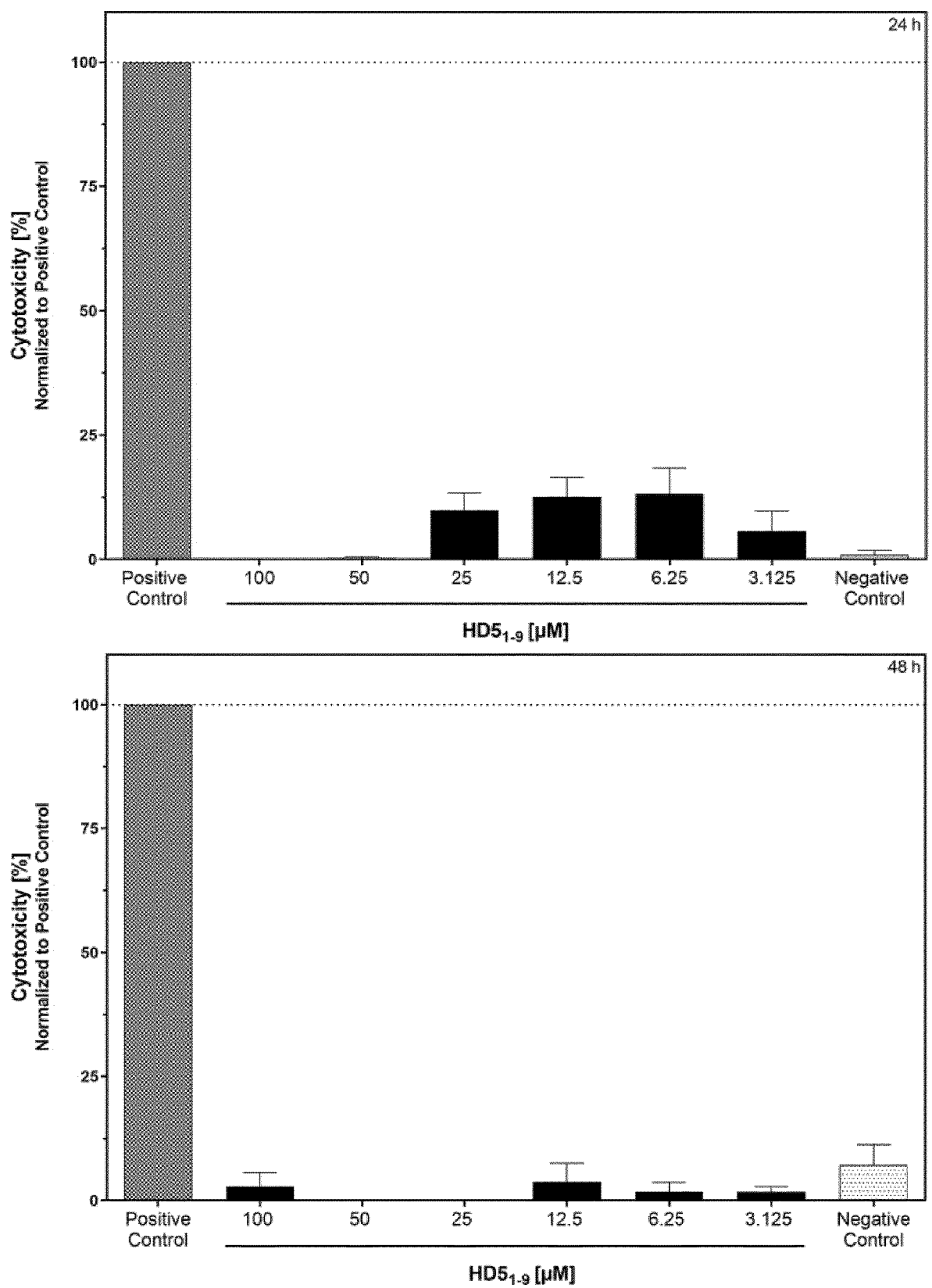
Figure 12B:
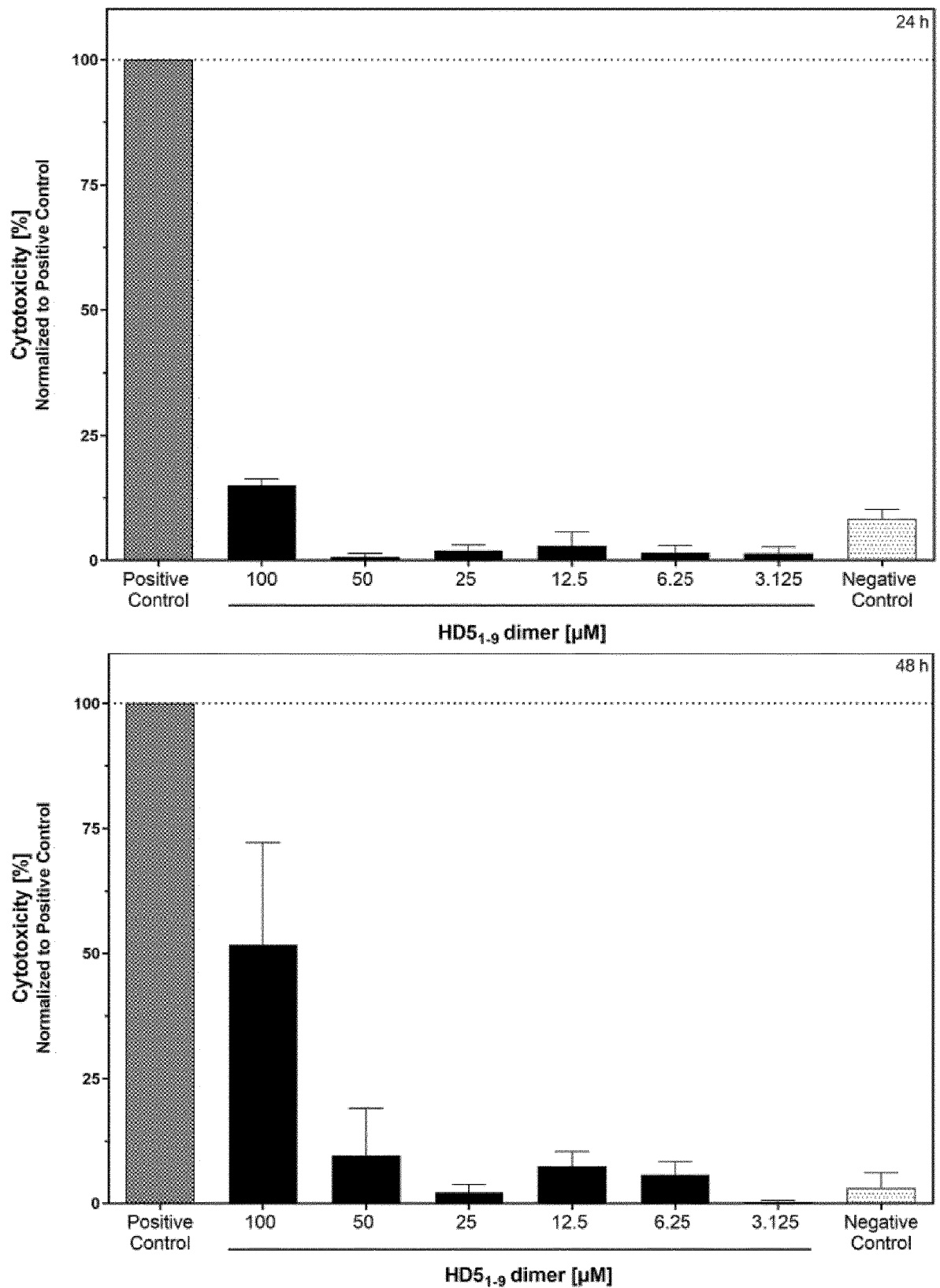
Figure 12C:
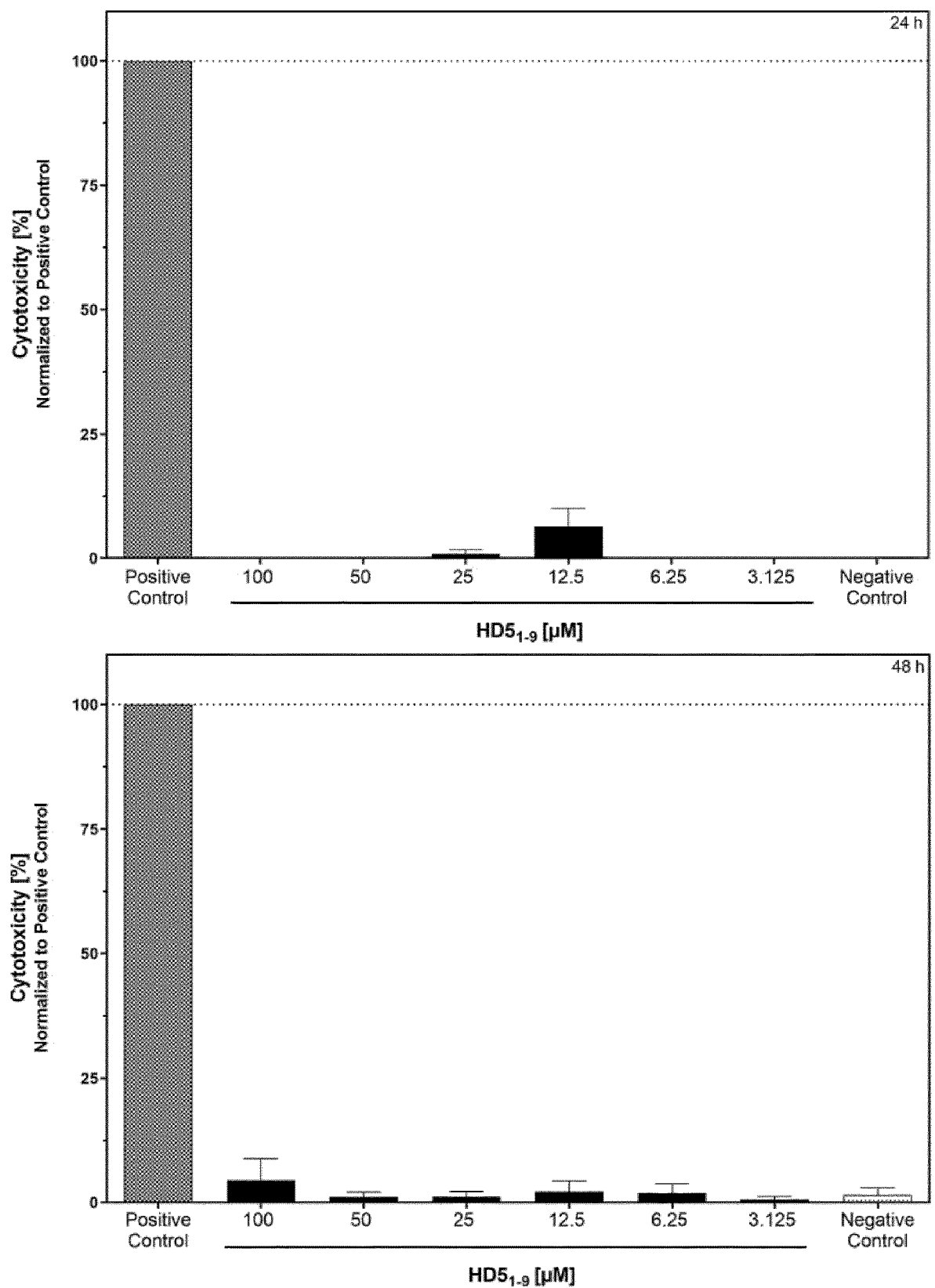
Figure 13:
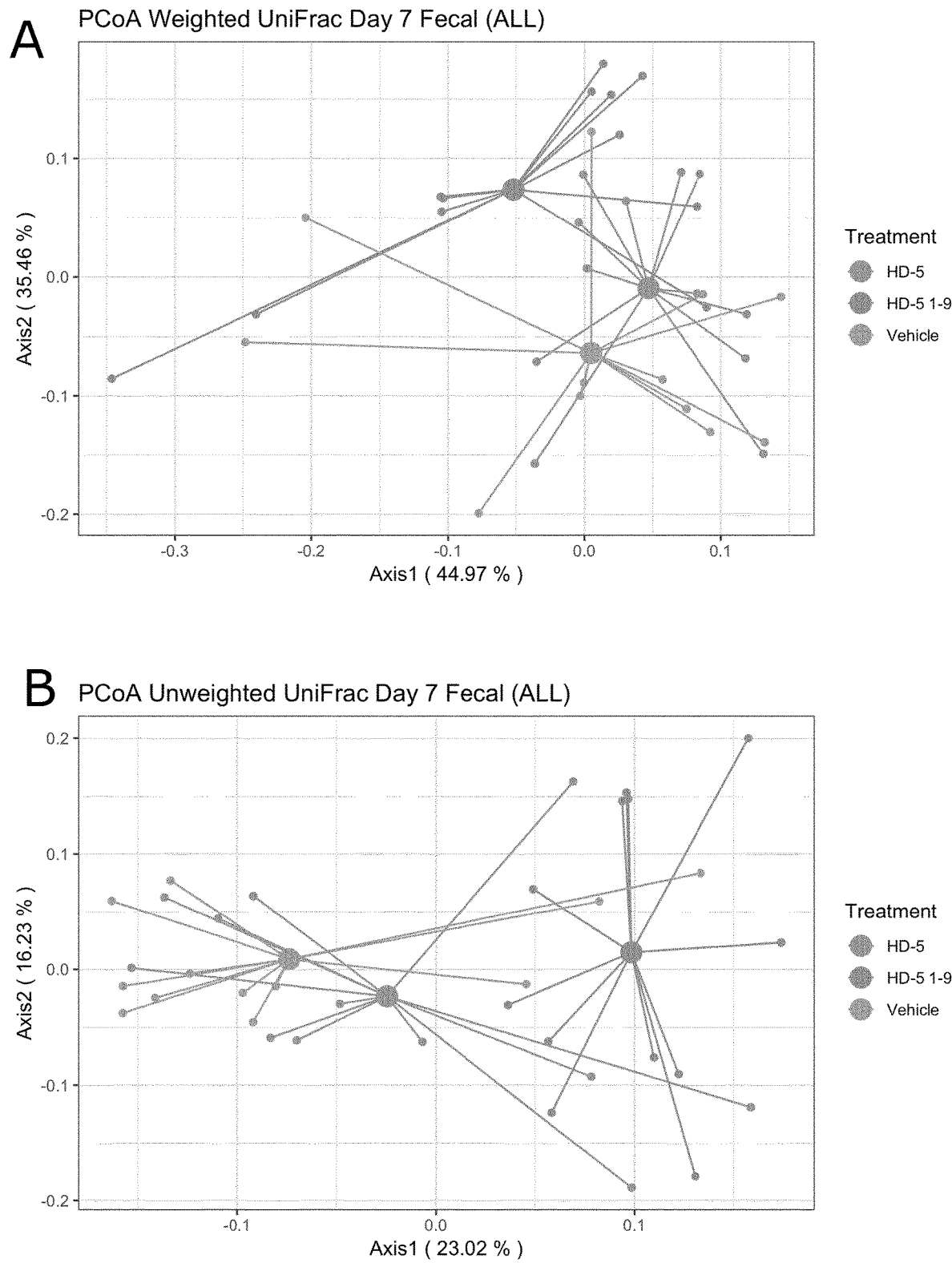
FIGS. 13A and 13B show the overall fecal microbial community. PCoA of weighted and unweighted UniFrac distances using all mice (n=12 per group) after 1 week of treatment comparing HD5 fl with $HD5_{1-9}$.

HD-519 Treatment Affects Certain Bacterial Genera, but not the Microbial Diversity To investigate the microbiome modulatory function of the identified HD-5 fragments, chow fed mice were treated with HD-$5_{1\text{-}9}$ or PBS orally for 7 days (7.19 μg/mouse), followed by 7 days washout. The microbiota composition of the two groups of mice were indistinguishable at baseline (Adonis PERMANOVA using Bray Curtis-distance, p=0.22). After 7 days of HD-$5_{1\text{-}9}$ treatment there was a borderline divergence in the overall microbiota composition in fecal samples compared to the control (Adonis PERMANOVA using Bray Curtis-distance, p=0.08) but not compared to the group's baseline microbiota (Adonis PERMANOVA using Bray Curtis-distance, p=0.38, data not shown). As HD-5 is naturally secreted by Paneth cells of the small intestine we therefore investigated the microbial community of the small intestine at necropsy. HD-$5_{1\text{-}9}$ treated mice exhibited no statistical change in the microbial community structure in the small intestine compared to the control after 7 days of washout (Adonis PERMANOVA using Bray Curtis-distance, p=0.09, data not shown). The results were consistent with an initial experiment implying that HD-$5_{1\text{-}9}$ surprisingly does not change the overall fecal microbiota composition in healthy, chow fed mice despite its pronounced anti-microbial efficacy (FIG. 12).

Figure 5A:
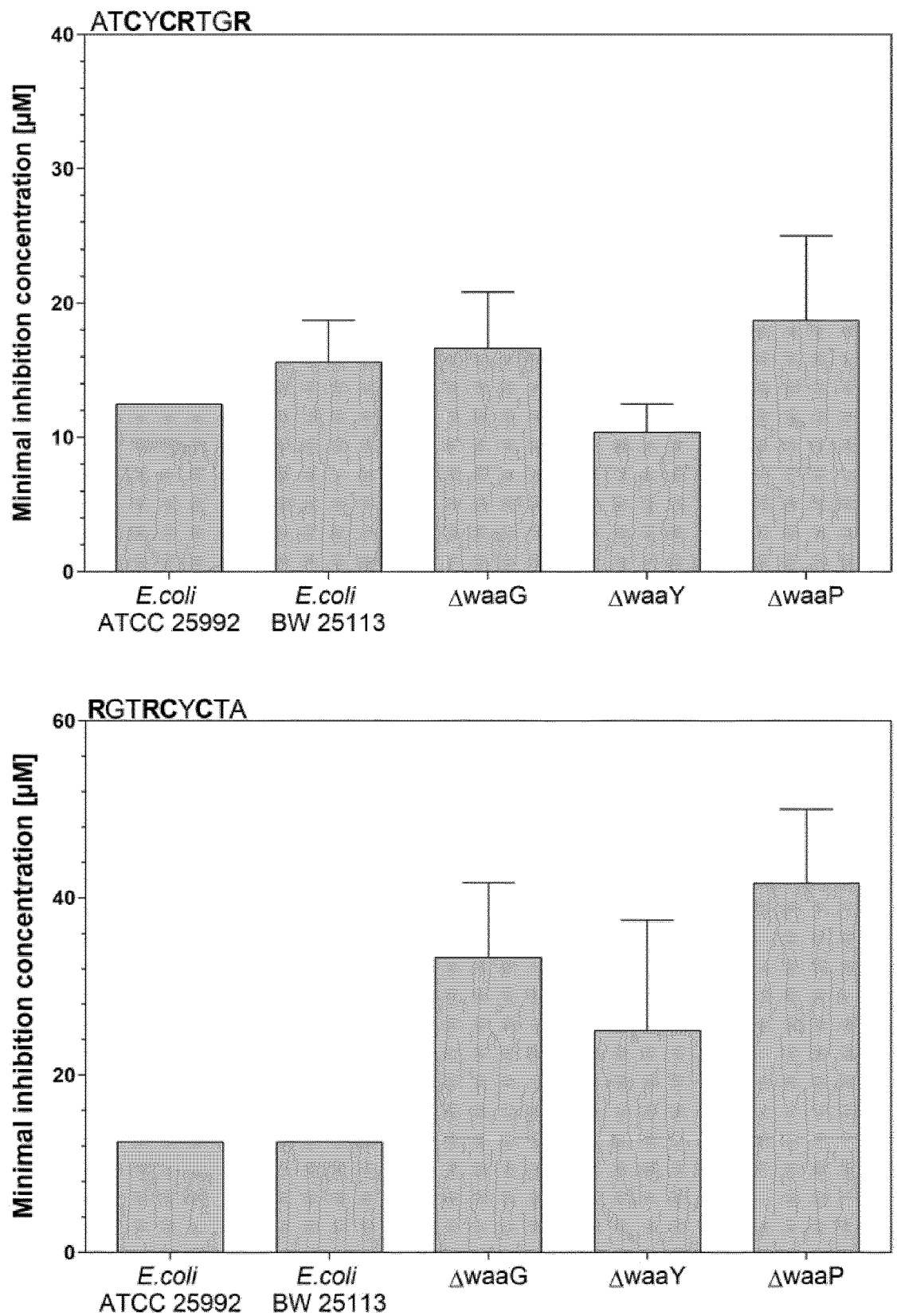
Figure 5B:
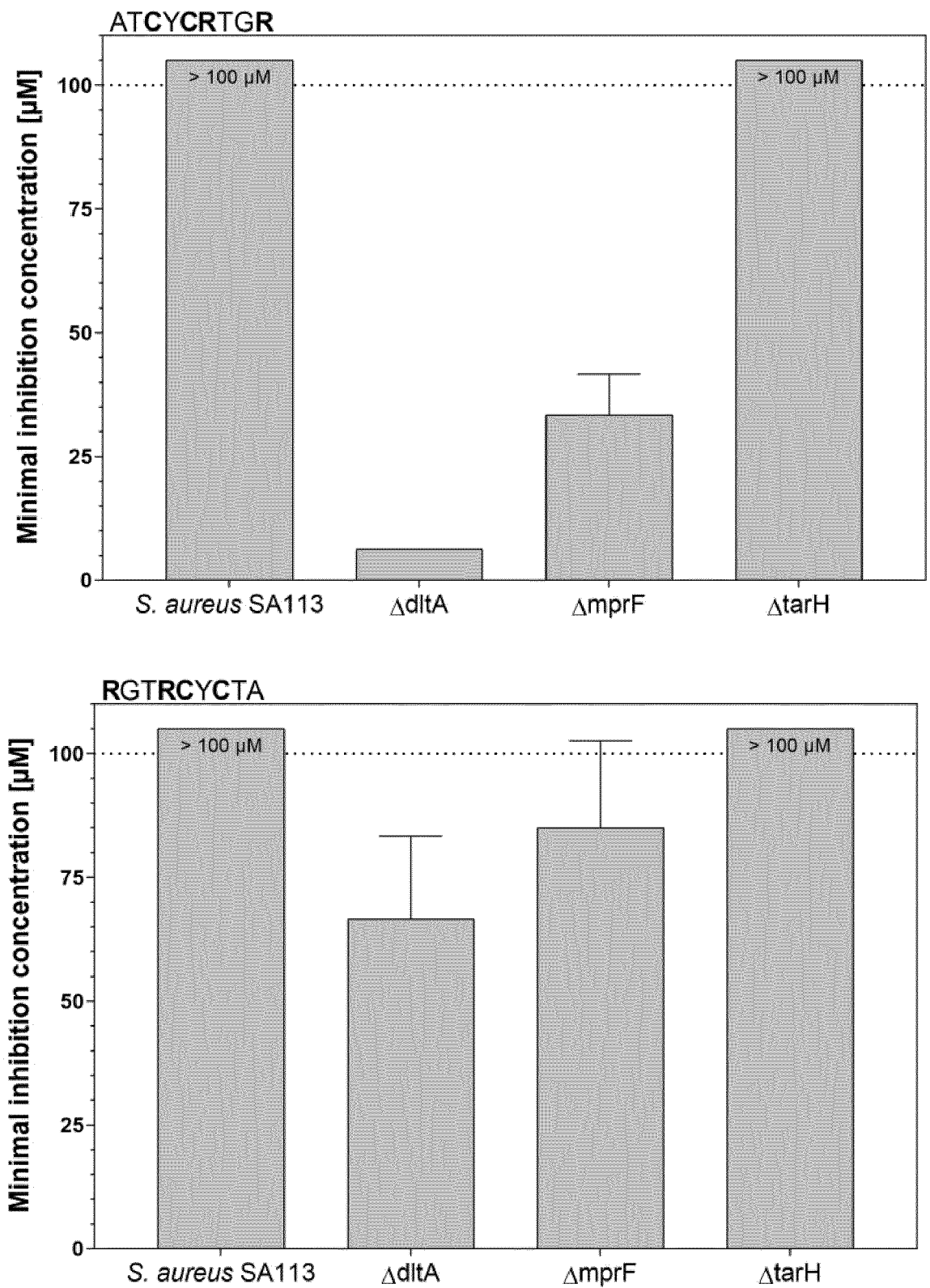
Figure 6:
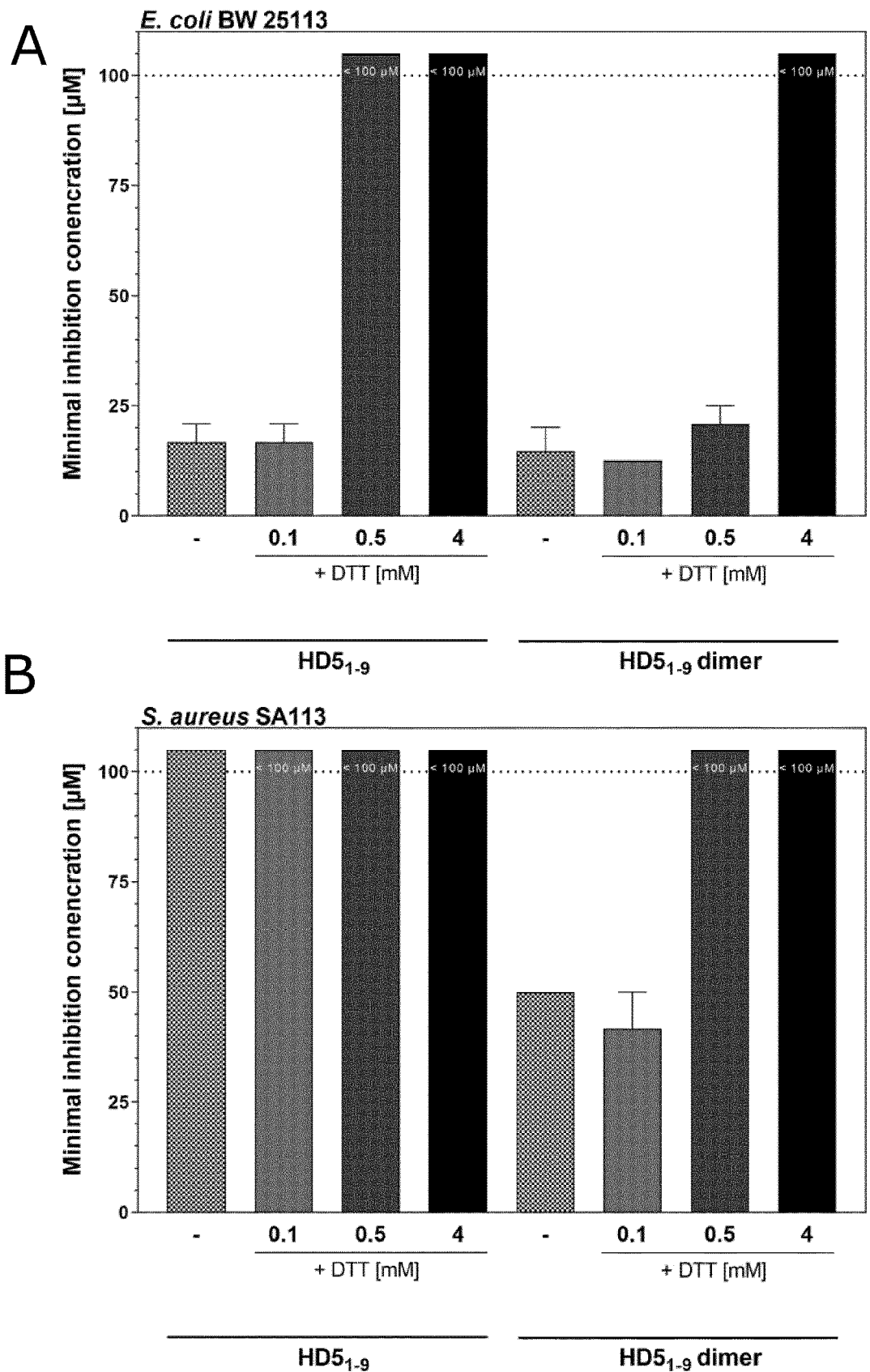
Figure 7A:
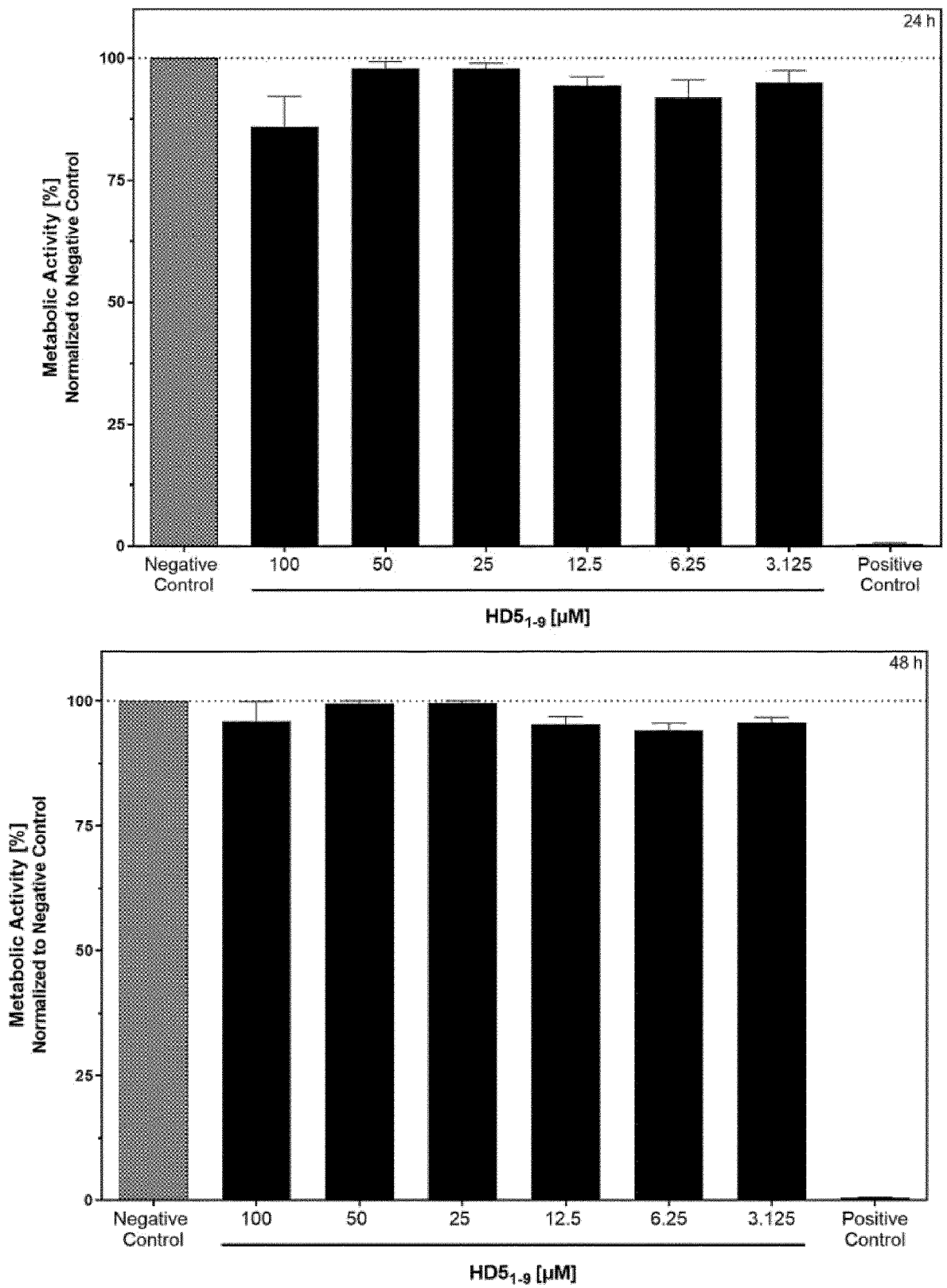
Figure 7B:
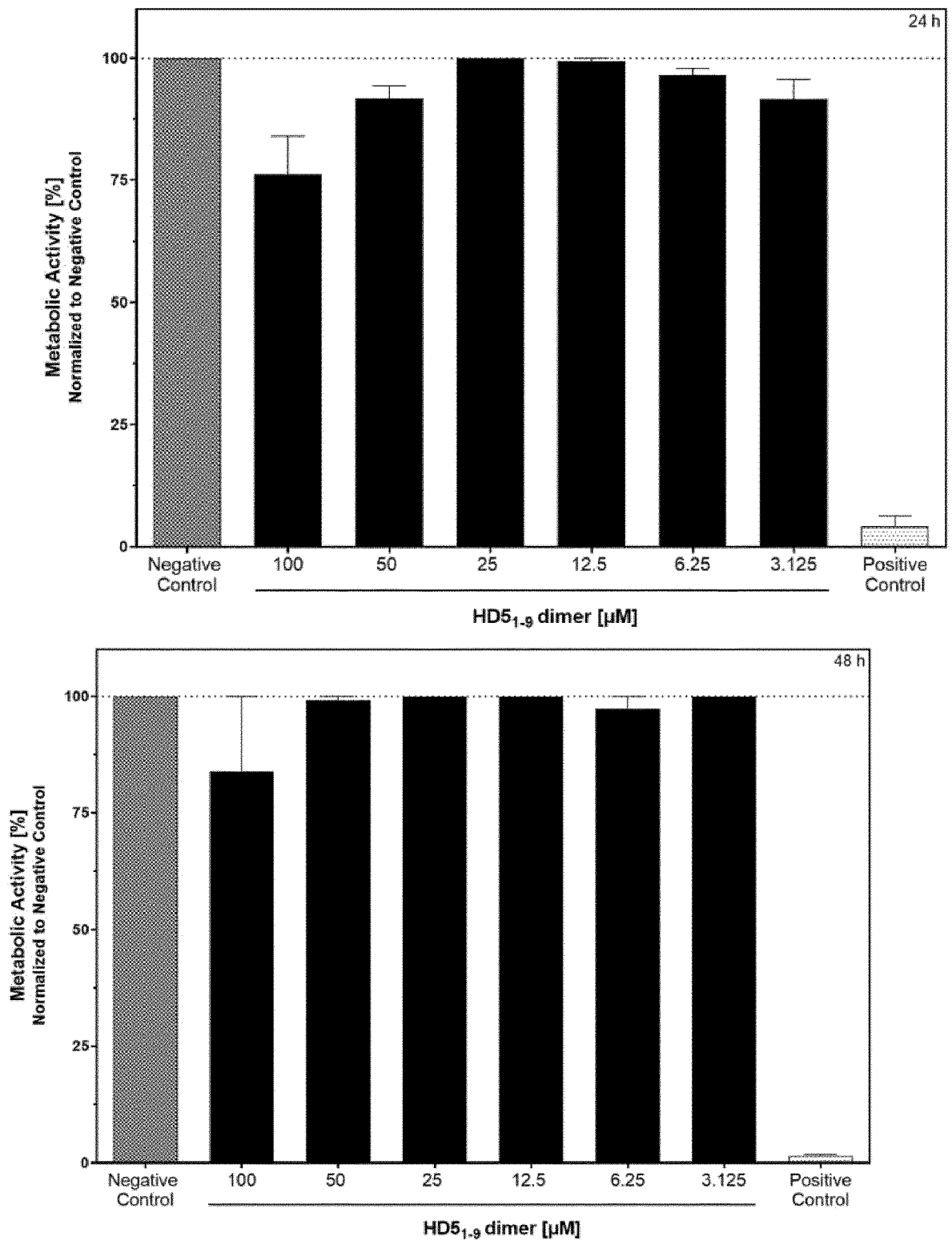
Figure 7C:
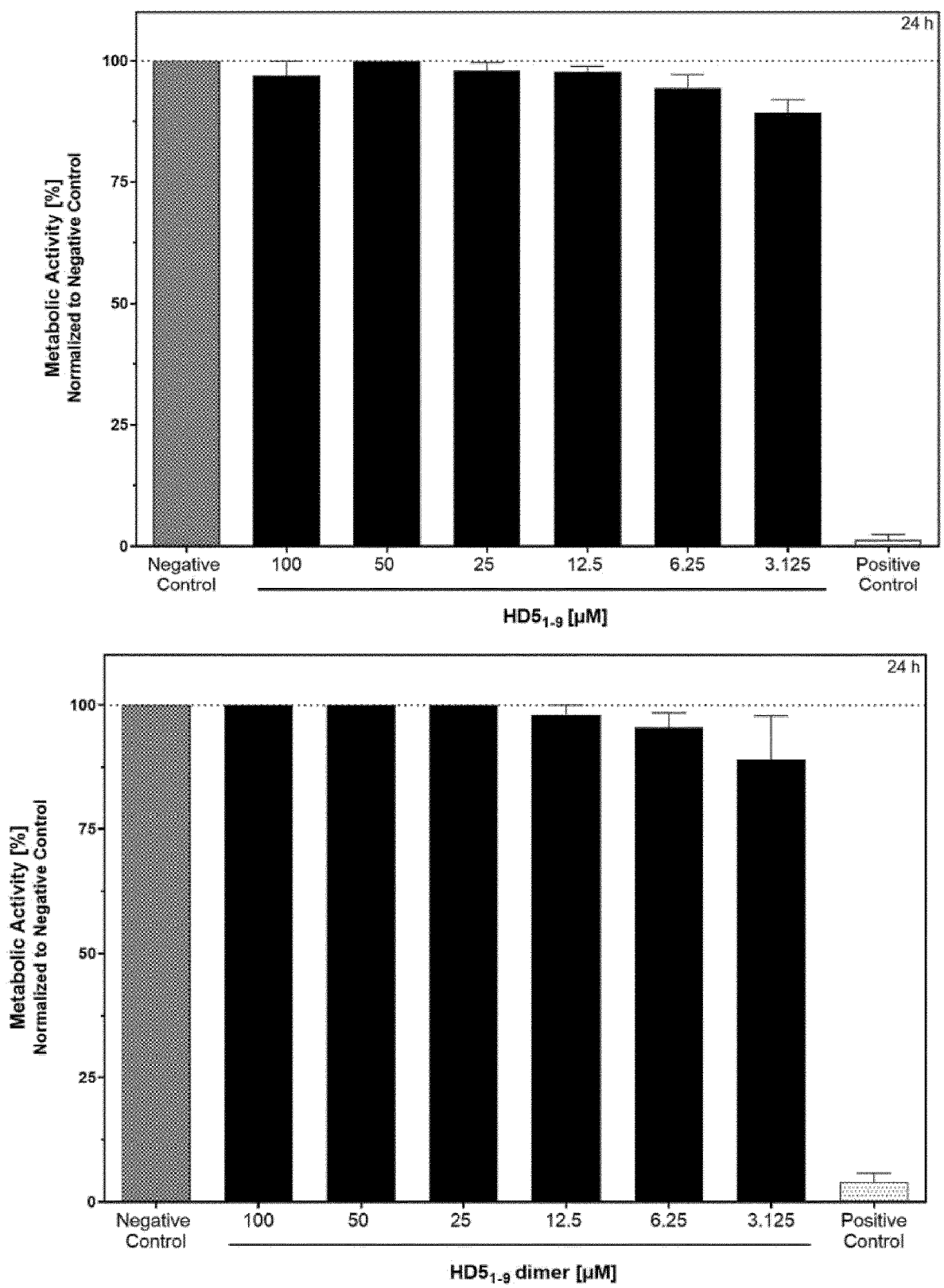

The Shannon diversity of the fecal microbiota composition was equal between the groups at baseline (Wilcoxon test, p=1), and remained similar after 7 days of HD-$5_{1\text{-}9}$ treatment (Wilcoxon test, p=0.18) and after the washout at day 14 (Wilcoxon test, p=0.07) (data not shown). The diversity of the small intestine microbiota was likewise similar between the two groups at day 14 (Wilcoxon test, p=0.45, FIG. 5B right), but not at day 7, where HD-519 treated mice surprisingly exhibited increased bacterial diversity compared to vehicle gavaged control mice (p=0.004, data now shown).

The experimental design further allowed to perform paired analyses of the fecal samples using a linear mixed model stratifying for potential co-caging effects and repeated sampling from the same mice. A significant effect of HD-$5_{1\text{-}9}$ on a few low-abundant microbial genera in the fecal samples was identified. More specifically, an increase in relative abundance of genera Parasutterella and Candidatus Stoquefichus was observed while GCA-900066575 of the Lacnospiraceae family and Hydrogenoanaero bacterium were decreased by HD-$5_{1\text{-}9}$ treatment. The genus Akkermansia was borderline increased by HD-519 in the fecal samples (Linear mixed model, p=0.0754, (data not shown), which confirmed the findings of an initial experiment in which Akkermansia was specifically increased by HD-$5_{1\text{-}9}$ treatment (Linear mixed model, p=0.0748). The small intestine microbiota was broadly similar between the two groups at day 14, although the relative abundance of Akkermansia was increased by HD-$5_{1\text{-}9}$ (Linear mixed model, p=0.0085), matching our result from the previous experiment (Linear mixed model, p=0.017. In addition the genus Ruminococcus_1 of the Ruminococcaceae family was increased in relative abundance while Intestinimonas, ASF356 of the Clostridiaceae family, and Ruminococcaceae_UCG-013 of the Ruminococcaceae family were decreased in relative abundances (data not shown).

Combined, these results demonstrate that HD-$5_{1\text{-}9}$ alters the amount of certain low-abundant bacteria in the fecal microbiota, surprisingly without affecting the overall community structure or diversity in healthy chow-fed mice.

Figure 9A:
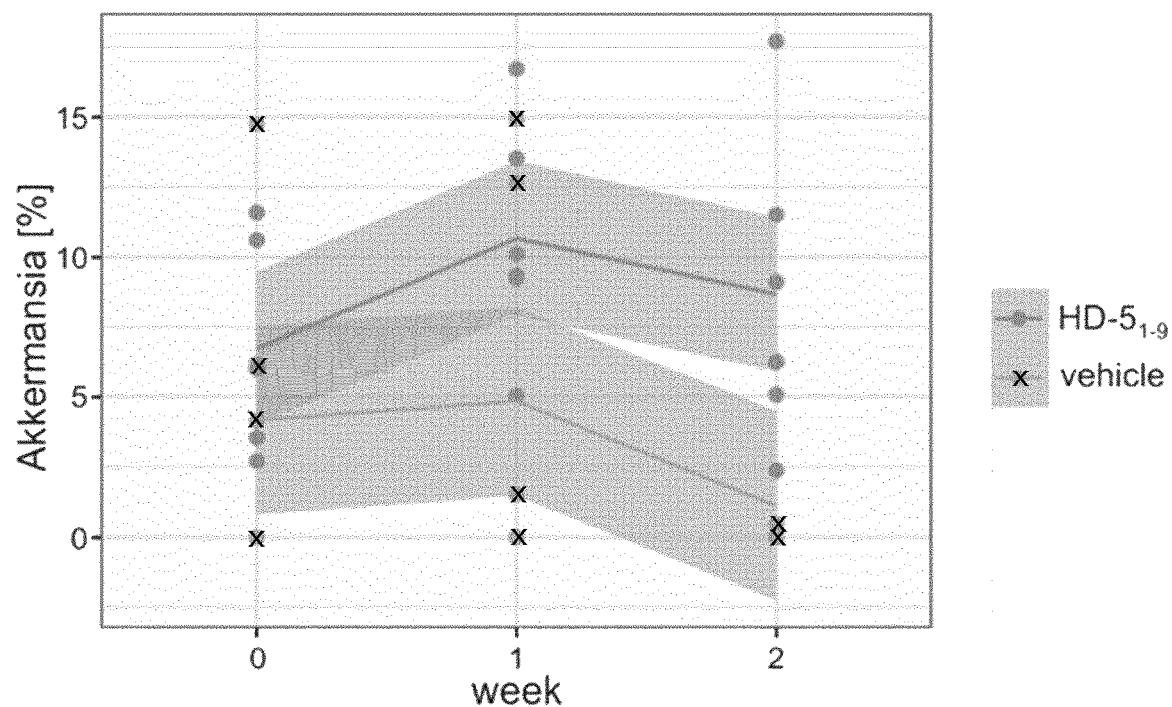
Figure 9B:
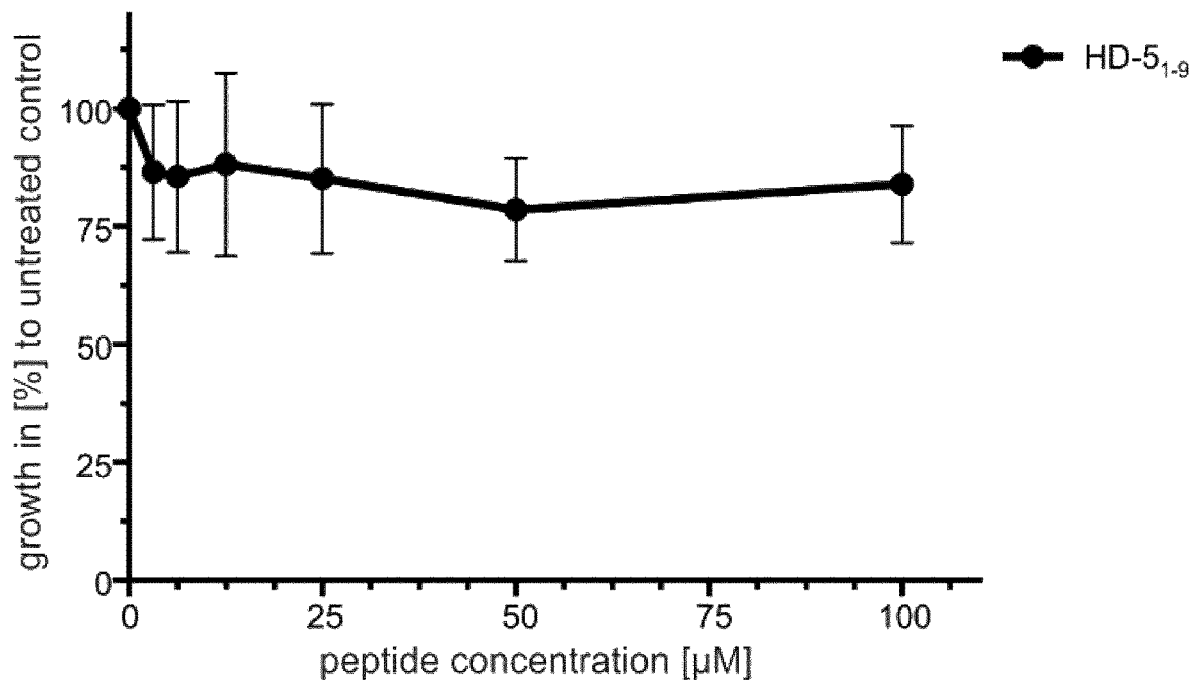

Additionally, it was tested if *A. muciniphila* is susceptible to HD-519 in a turbidity broth assay. The findings indicate, that even small concentrations of HD-$5_{1\text{-}9}$ decrease the growth of *A. muciniphila* slightly, but did not kill the bacteria (FIG. 9B).

Figure 10:
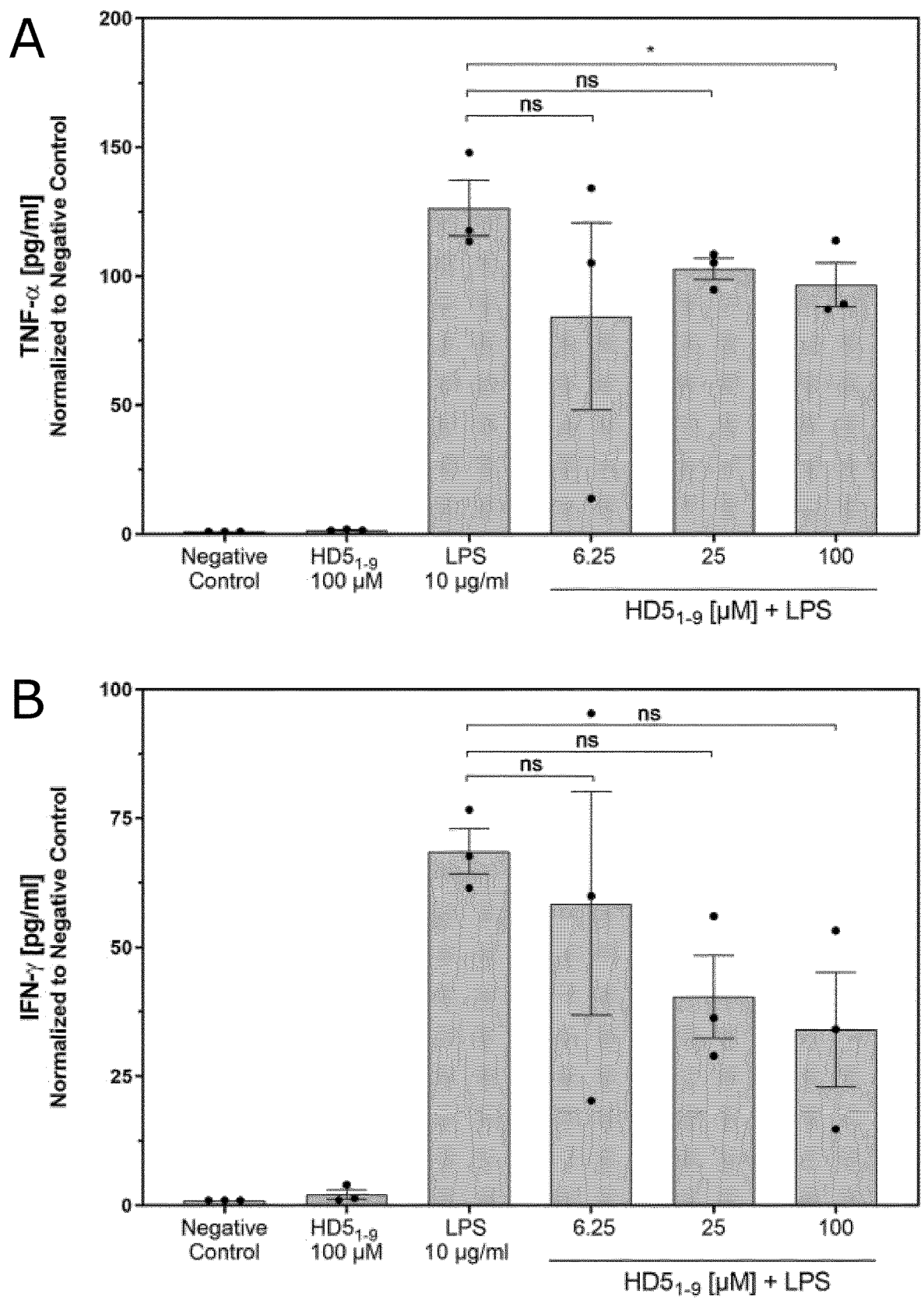

The pro- and anti-inflammatory effect of HD$5_{1\text{-}9}$ was tested and despite the fact that there was a low anti-inflammatory effect with a dose dependent tendency to reduce IFN-γ and IL-8 this was not statistically significant and neither was the dose dependent tendency to increase IL-10 (FIG. 10).

Figure 11A:
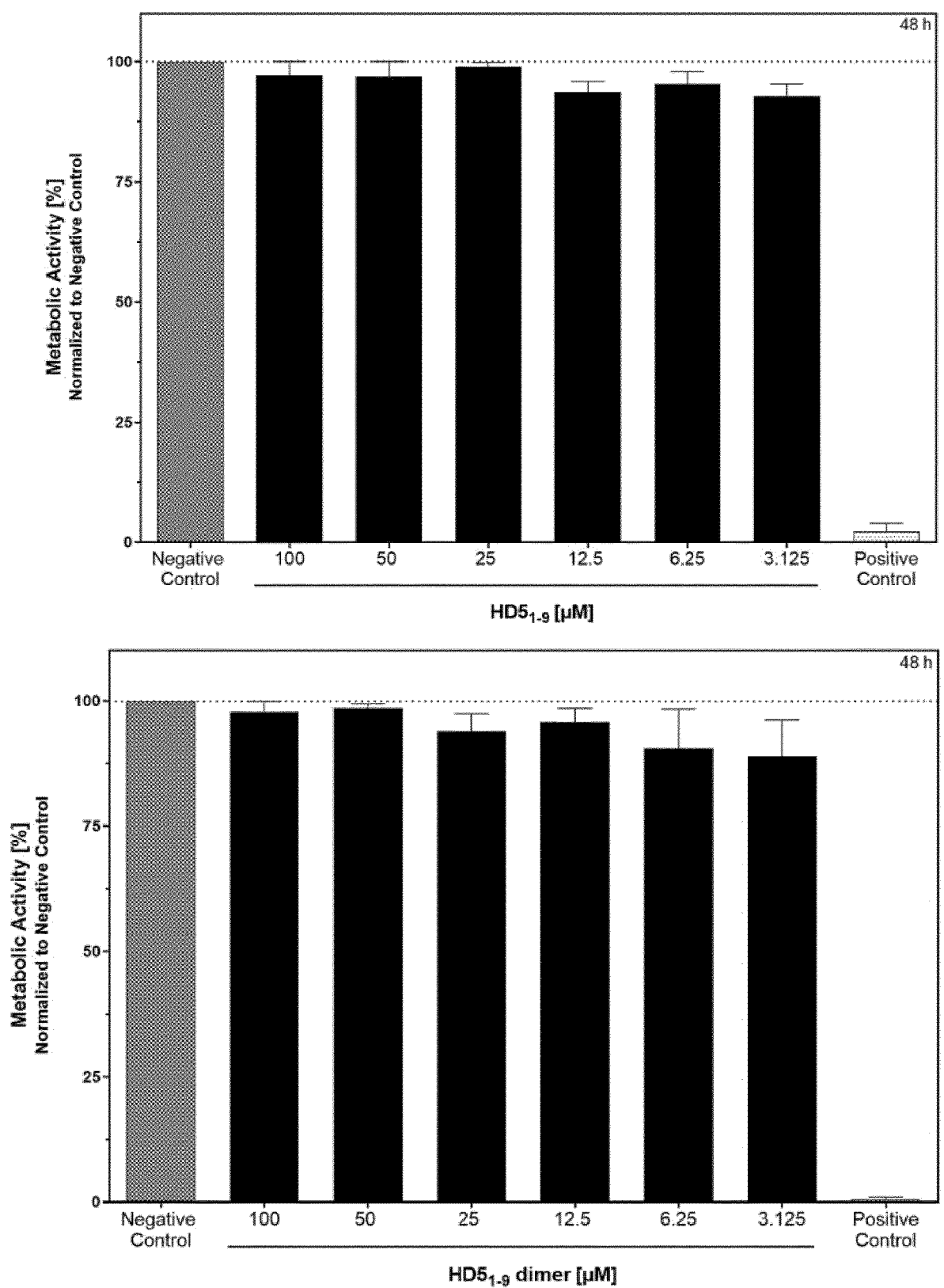
Figure 11B:
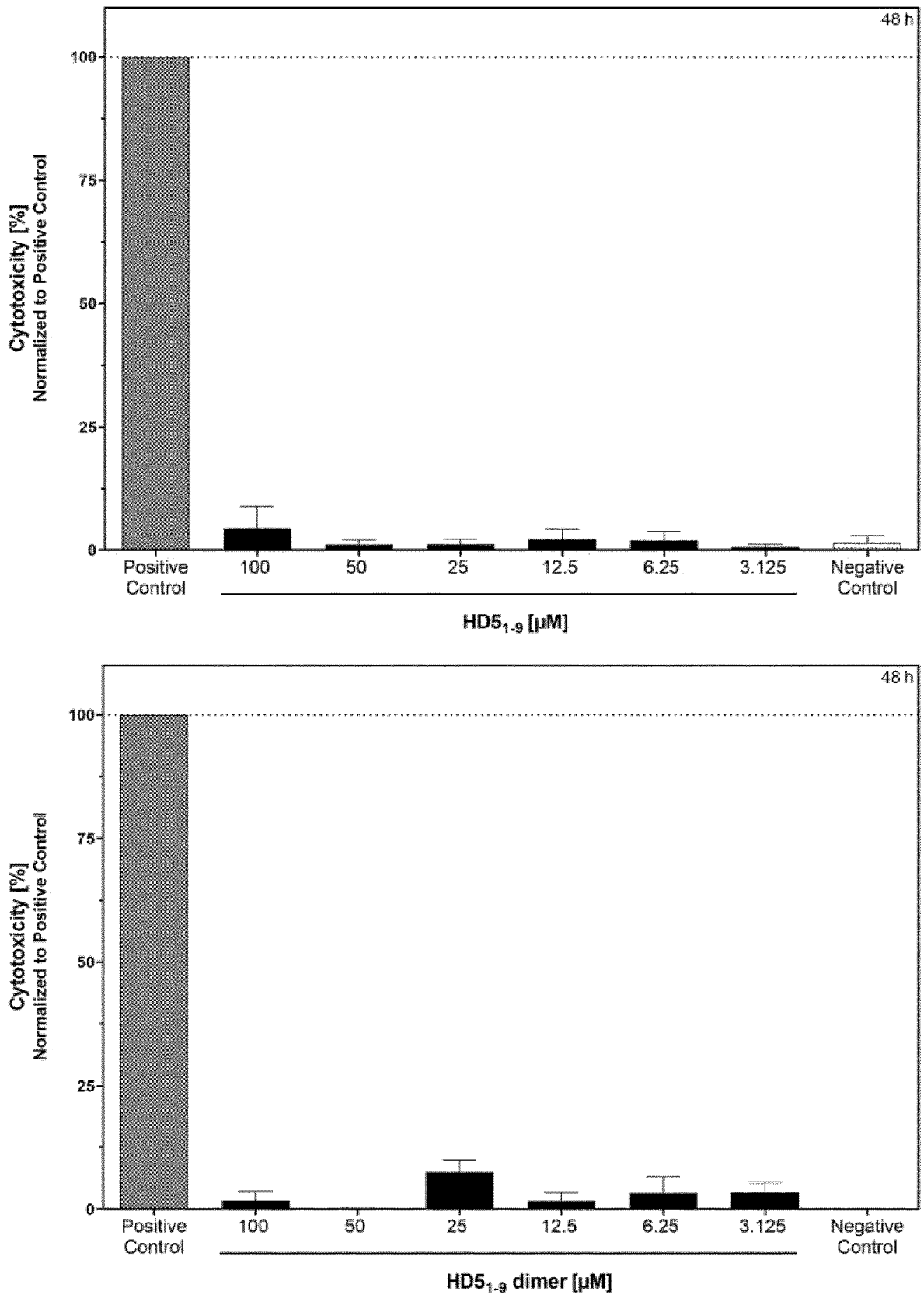
Figure 11C:
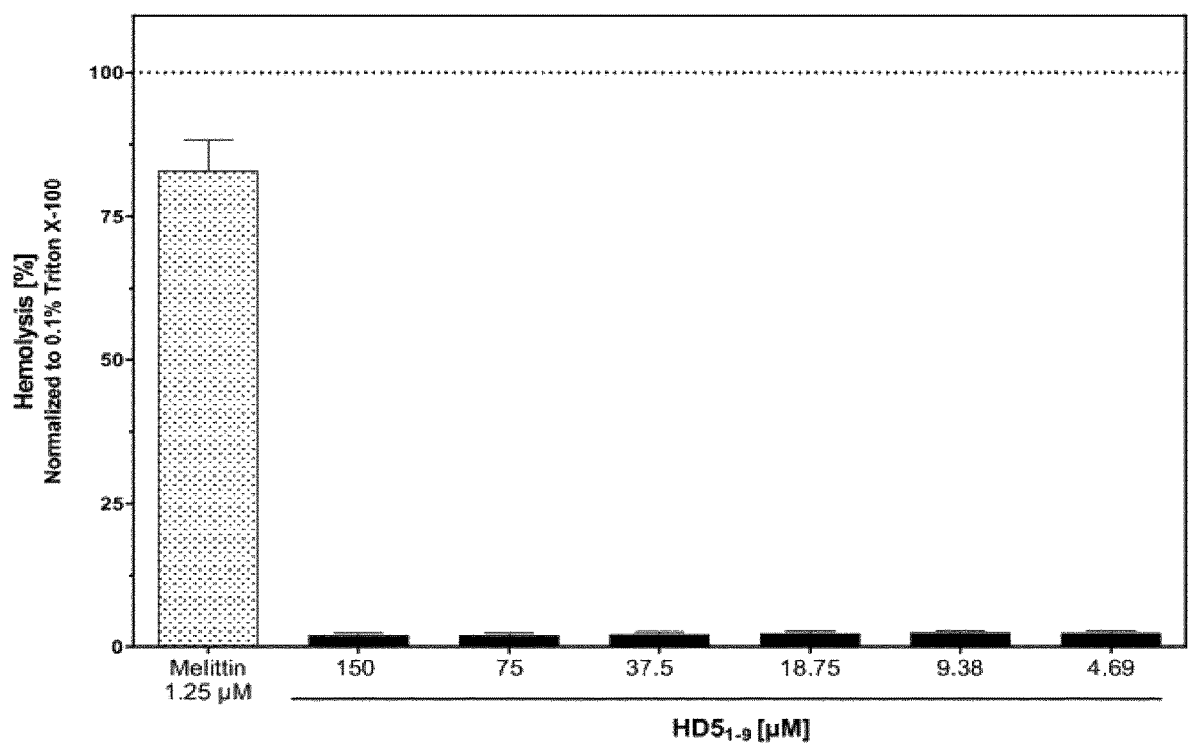

The toxic effect of HD$5_{1\text{-}9}$ was also tested in a number of in vitro experiments (FIGS. 11 and 12) but despite HD$5_{1\text{-}9}$ being a short linear peptide surprisingly no toxicity was observed.

Identification of Cell Wall Targets in Mutants of *E. coli* BW 25113 and *S. aureus* SA113

The mode of action of HD$5_{1\text{-}9}$, was identified employing cell wall mutants of *E. coli* BW 25113 and *S. aureus* SA113. The aim was to analyze which components of the cell wall are important for binding of HD$5_{1\text{-}9}$ and whether the charge plays a crucial role. A turbidity assay was performed as described above. *E. coli* strains with different LPS structures were investigated by determining the MIC (FIG. 16). The wild type *E. coli* BW 25113 as well as *E. coli* ATCC 25922 were used as controls. The last one contains a similar cell wall composition as *E. coli* BW 25113 but additionally an O-antigen thus possesses the full-length LPS. The mutant *E. coli* BW 25113 ΔwaaG contains the same amount of phosphate residues in the inner membrane as the wild type thus possess a similar charge, but the outer core is missing. The mutant ΔwaaY includes an outer core while some phosphate residues in the inner core are missing. The last *E. coli* mutant ΔwaaP possess an outer membrane as well, but no phosphate residues in the inner membrane leading to a more positive charge of the inner membrane[19].

The antimicrobial activity of HD5$_{1-9}$ was analyzed against different *E. coli* strains and mutants. *E. coli* ATCC 25922 with full-length LPS was as highly susceptible towards HD5$_{1-9}$ as the tested *E. coli* BW25113 lacking the O antigen. In order to clarify the function of the outer core during HD5$_{1-9}$ binding to the bacterial cell wall the mutant ΔwaaG was used. Determination of the MIC shows similar antimicrobial effects of HD5$_{1-9}$ against ΔwaaG like *E. coli* ATCC 25922 and *E. coli* BW25113. Surprisingly, *E. coli* ΔwaaY, lacking one inner core phosphate, and *E. coli* ΔwaaP, lacking two inner core phosphates, were not more resistant towards HD5$_{1-9}$. This observation is surprising as it is known that cationic antimicrobial peptides interact with anionic phospholipids in the cell wall due to electrostatic interactions. Lacking this negative charge in the inner core of the cell wall would normally reduce the capability of the peptide to bind on the bacterial cell wall. But HD5$_{1-9}$ surprisingly shows bactericidal effects at a concentration of approximately 12.5 μM for all the described *E. coli* mutants. An explanation could be that the antimicrobial activity not only depends on the negative charge of the cell wall but that also an additional binding site must be present in Gram-negative bacteria.

Figure 15:
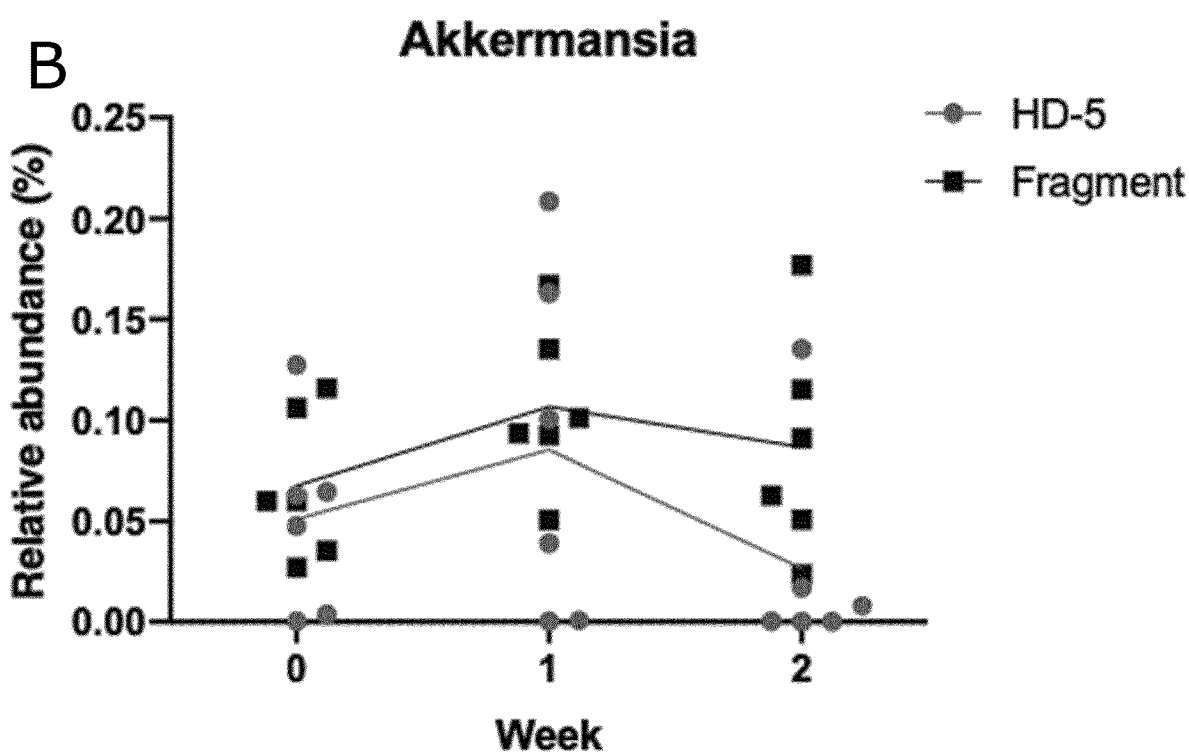

The antimicrobial activity of HD5$_{1-9}$ and variants was investigated against various *S. aureus* SA113 strains with different cell wall mutations (FIG. 17). The aim was to investigate how HD5$_{1-9}$ is capable to bind to the cell wall of Gram-positive bacteria and whether the charge plays a decisive role for the antimicrobial activity of HD5$_{1-9}$. The first mutant ΔdltA does not contain D-alanine in the peptidoglycan layer leading to a more negative charge of the peptidoglycan layer[20]. The mutant ΔmprF lacks L-lysine resulting in a more negative charge of the cell membrane[21]. The last mutant ΔtarH contains additionally wall teichoic acid causing a strengthening of the peptidoglycan[22]. HD5$_{1-9}$ showed no growth inhibition against the wild type strain *S. aureus* SA113 whereas the *S. aureus* ΔdltA mutant containing a more negative peptidoglycan layer was much more susceptible towards HD5$_{1-9}$ showing a MIC at 6.25 μM (FIG. 15). HD5$_{1-9}$ also displayed bactericidal effects against the ΔmprF mutant lacking L-lysin, which results in a more negative charge of the bacterial cell membrane. However, surprisingly strengthening of the peptidoglycan layer due to additional teichoic acid in the *S. aureus* ΔtarH mutant decreased the antimicrobial effects of HD5$_{1-9}$. These results emphasize the importance of the cell wall charge for the binding of HD5$_{1-9}$ to Gram-positive bacteria, whereas the cell wall charge seems of less importance for the binding to Gram-negative bacteria.

Characterization of the Antimicrobial Activity of HD5$_{1-9}$ and HD5$_{1-9}$-Dimer Against Different Bacteria HD5 possess leucine residues enabling it to form dimers. Leucine substitutions of HD5 cause a decline of the antimicrobial activity and ability to kill microorganisms indicating that dimerization of HD5 is important for its function (Rajabi et al., 2008, 2012; Szyk et al., 2006)[23-25]. In addition, cysteine residues of HD5 are capable of composing dimers due to disulfide or hydrogen bonds. Studies showed that cysteine mutations of HD5 influence the oxidative folding, antibacterial activity, Gram-negative bacterial membrane permeabilization as well as proteolytic stability (Wanniarachchi et al., 2011)[26].

It is thus reasonable to assume that also HD5$_{1-9}$ is able to form dimers due to the existence of cysteine residues. Two monomers of HD5$_{1-9}$ were linked via disulfide bonds resulting in dimerization. The aim was the investigation of the antimicrobial activity of HD5$_{1-9}$ structured in its dimer form compared to the monomer form against selected bacteria. HLPC and Mass Spectometry identified the dimer as having a MW of 2058 consistent with the existence of one disulphide bridge between the two monomers.

The minimal inhibition concentration was determined in a turbidity assay for Gram-positive bacteria (*S. aureus* species) and Gram-negative bacteria (*Salmonella* species) treated with the same concentrations as for HD5$_{1-9}$.

The conducted experiments demonstrated, that the antimicrobial activity of HD5$_{1-9}$ surprisingly is similar to its dimer form or even better against tested bacteria. The antimicrobial activity of HD5$_{1-9}$ as well as its dimer form is almost the same against different *Salmonella* species (FIG. 18). However, surprisingly dimerized HD5$_{1-9}$ displayed a much better bactericidal activity against *S. aureus* species compared to the monomer form of HD5$_{1-9}$ (FIG. 19). This implicates a surprising different mode of action for the two forms of HD5$_{1-9}$.

Identification of a Novel HNP-4 Fragment after a Tryptic Digestion

We incubated HNP-4 with 2 mM TCEP to open the disulphide bonds leading to a more linear structure susceptible to proteolytic digest. We analyzed the trypsin incubated reduced HNP-4 via LC/MS methods and were able to detect several fragments (FIG. 20A). According to the observed ions and their mass to charge ratio we were able to clearly identify these fragments, which are mostly located in the N-terminal region based on the cleaving sites of trypsin. As it is commonly accepted that the net charge of AMPs could play an important role to their antimicrobial activity, we focused on HNP-4$_{1-11}$ with a positive net charge of +3.

Antimicrobial Efficacy of HNP-4$_{1-11}$

Because the natural stability of short linear peptides is weak, we used an additional modified form of HNP-4$_{1-11}$ (HNP-4$_{1-11mod}$). Here we exchanged the L-amino acids with D-amino acids and modified the N-terminus (acetylation) and C-terminus (amidation). Both modifications should result in a gain of stability[27,28], hence potentially leading to a stronger antimicrobial activity. To analyze the antimicrobial activity of HNP-4$_{fl}$, HNP-4$_{1-11}$ and HNP-4$_{1-11mod}$ we used RDAs against a subset of different commensal and pathogenic bacteria. All of our tested peptides showed a strong antimicrobial activity against most of the tested bacteria (FIG. 21). While the RDA is the suitable assay to determine a general antimicrobial activity of different peptides, a comparison between different peptides is not possible according to their different abilities (e.g. diffusion) in an agarose gel. We therefore next used a turbidity broth assay to determine the MIC of HNP-4$_{fl}$, HNP-4$_{1-11}$ and HNP-4$_{1-11mod}$ against pathogenic (some multi-drug resistant) Gram negative and positive bacteria and one fungal strain (Table 5). While all peptides displayed antimicrobial activity against tested bacteria (sole exception: HNP-4$_{fl}$ against *K. pneumoniae* DSM30104), HNP-4$_{1-11}$ was surprisingly equimolar to HNP-4$_{fl}$, indicating that the antimicrobial efficacy of the natural complex-to-produce HNP-4$_{fl}$ is solely dependent on the first 11 amino acids (HNP-4$_{1-11}$). Pointing further towards enhanced bactericidal efficacy of this linear fragment, HNP-4$_{1-11mod}$, which is expected to exhibit increased stability over the non-modified version, was superior to both HNP-4$_{fl}$ and HNP-4$_{1-11}$ with a MIC several fold lower than the one observed for the natural occurring full length peptide. We have thus unleashed the antimicrobial activity of the full length peptide by tryptic digestion whereby we identified a single fragment with a remarkable antimicrobial potential, exceeding that of the full length peptide on molar level. Surprisingly, we observed the antimicrobial efficacy of the peptides to be equally efficient between multi-drug-resistant and non-resistant strains. Thus, a proteolytic digestion of AMPs could be used to generate new active sequences which could lead to new strategies to overcome antibiotic-resistant bacteria.

TABLE 5

Comparison of the MIC of HNP-$4_{fl}$, HNP-$4_{1\text{-}11}$ and HNP-$4_{1\text{-}11mod}$

|  |  | HNP-$4_{fl}$ | | HNP-$4_{1\text{-}11}$ | | HNP-$4_{1\text{-}11mod}$ | |
| --- | --- | --- | --- | --- | --- | --- | --- |
|  |  | µM | µg/ml | µM | µg/ml | µM | µg/ml |
|  | MIC after 12 hours | | | | | | |
| gram negative | A. baumannii 4-MRGN | 12.5 | 46.4 | 25 | 33.5 | 6.25 | 8.6 |
|  | A. baumannii DSM30007 | 3.125 | 11.6 | 6.25 | 8.4 | 6.25 | 8.6 |
|  | E. coli JM83 | 12.5 | 46.4 | 6.25 | 8.4 | 6.25 | 8.6 |
|  | K. pneumoniae 3-MRGN | >>> | >>> | 25 | 33.5 | 6.25 | 8.6 |
|  | K. pneumoniae DSM30104 | 100 | 371.5 | 25 | 33.5 | 6.25 | 8.6 |
|  | P. aeruginosa 4-MRGN | 50 | 185.8 | 50 | 67.1 | 6.25 | 8.6 |
|  | P. aeruginosa ATCC27853 | 6.25 | 23.2 | 12.5 | 16.8 | 6.25 | 8.6 |
|  | P. aeruginosa PAO1 | 12.5 | 46.4 | 12.5 | 16.8 | 12.5 | 17.3 |
|  | P. aeruginosa XPAT1 | 12.5 | 46.4 | 12.5 | 16.8 | 12.5 | 17.3 |
|  | P. aeruginosa XPAT2 | 12.5 | 46.4 | 12.5 | 16.8 | 12.5 | 17.3 |
|  | Y. enterocolitica | 12.5 | 46.4 | 12.5 | 16.8 | 6.25 | 8.6 |
| gram positive | S. aureus USA300 | 6.25 | 23.2 | 50 | 67.1 | 12.5 | 17.3 |
|  | S. aureus ATCC25923 | 6.25 | 23.2 | 12.5 | 16.8 | 3.125 | 4.3 |
|  | S. enterica serovar enteriditis | 100 | 371.5 | 25 | 33.5 | 12.5 | 17.3 |
|  | E. faecium 475747 | 3.125 | 11.6 | 3.125 | 4.2 | 3.125 | 4.3 |
|  | E. faecium DSM20477 | 6.25 | 23.2 | 12.5 | 16.8 | 6.25 | 8.6 |
|  | MIC after 24 hours | | | | | | |
|  | C. albicans 529L | 50 | 185.8 | 100 | 134.2 | 25 | 34.6 |

We determine the MIC as the lowest concentration without detectable bacterial growth in all experiment after 12 hours of incubation at 37° C. For C. albicans we used 24 hours of incubation..
Each experiment was carried out at least three independent times.
The concentration is expressed both in molarity (µM) and mass (µg/ml).

Figure 22B:
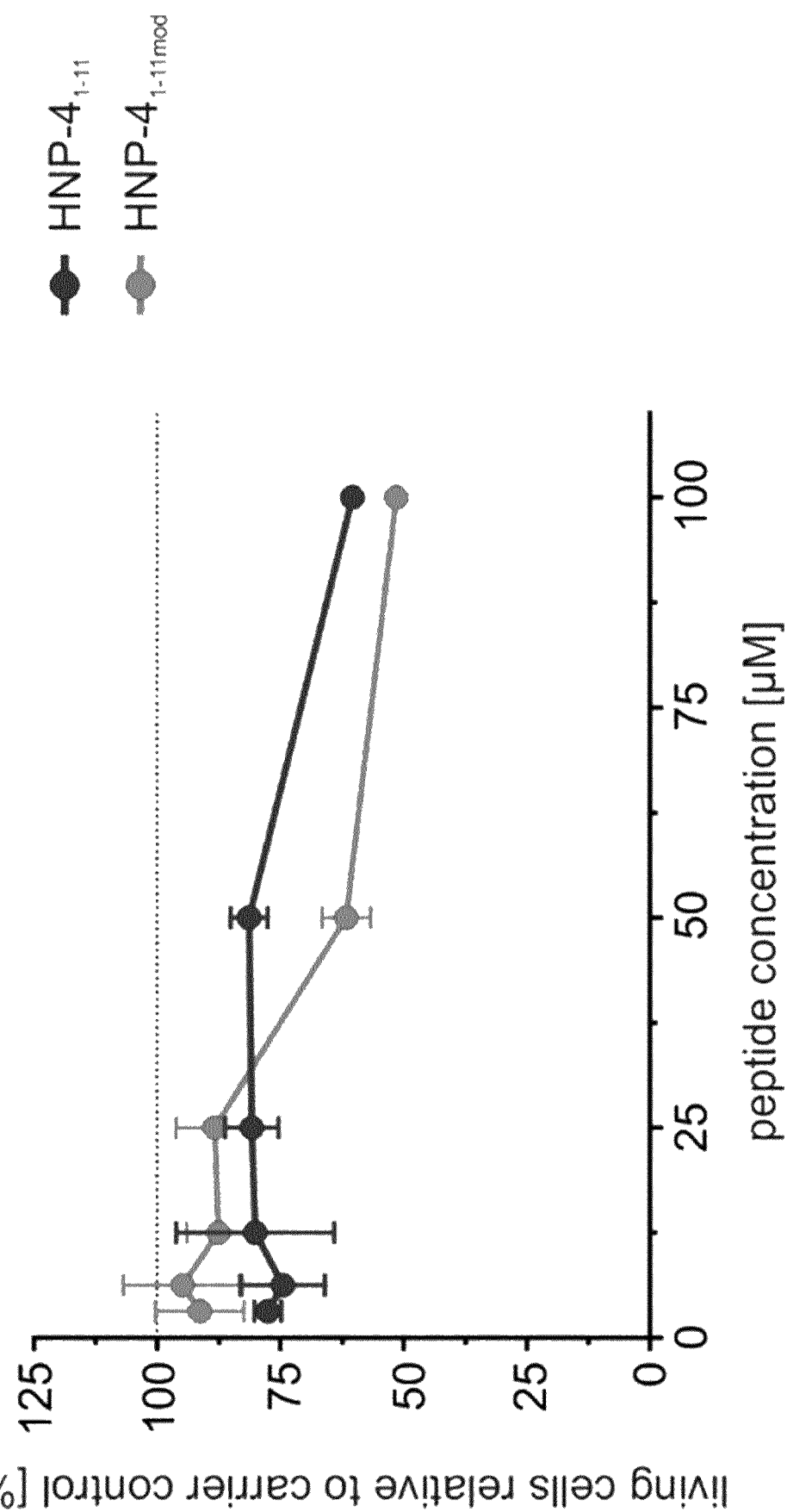
Figure 22C:
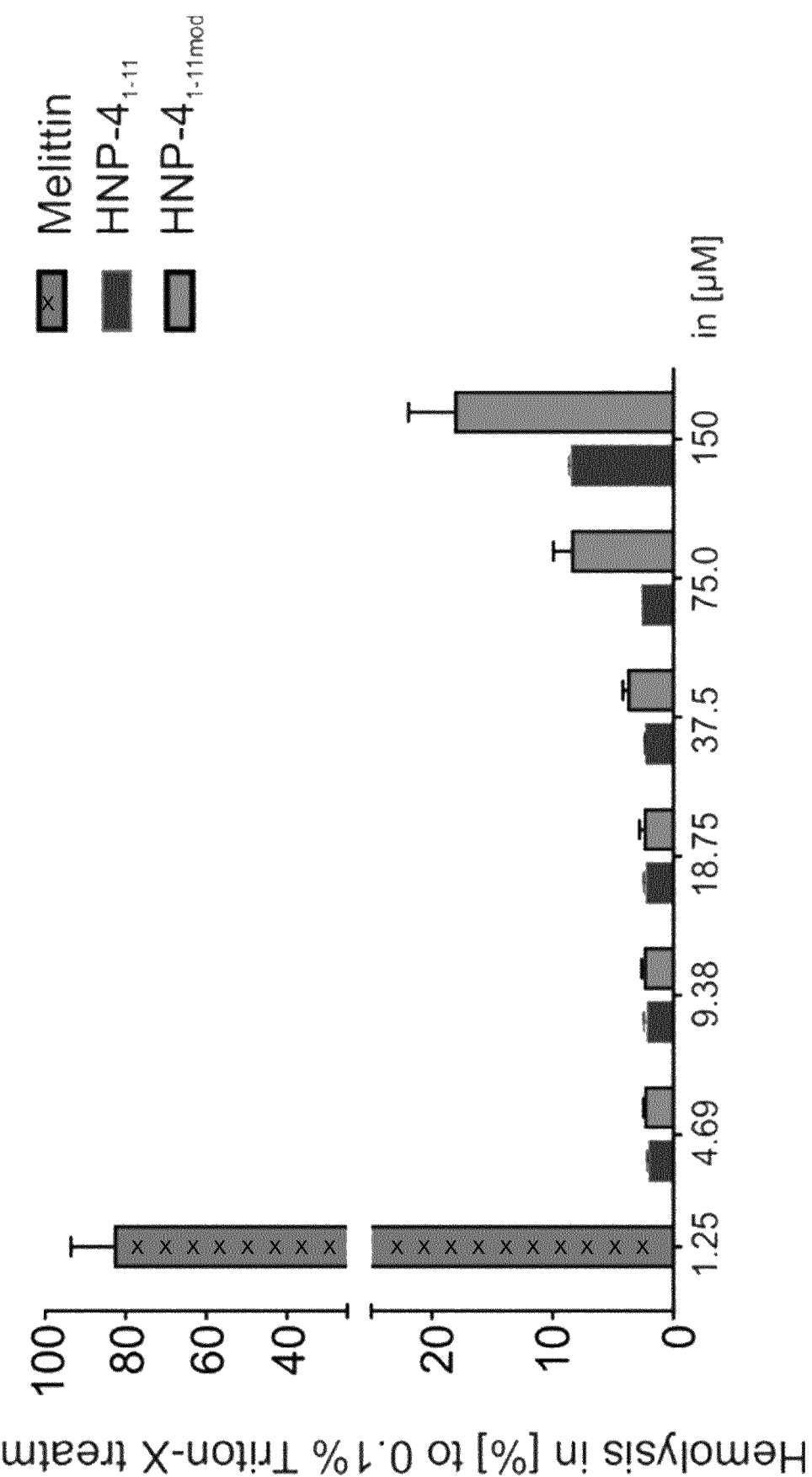

Cytotoxic and Hemolytic Effects of HNP-$4_{1\text{-}11}$ and HNP-$4_{1\text{-}11mod}$ To determine the potential of HNP-$4_{1\text{-}11}$ and HNP-$4_{1\text{-}11mod}$ for an in vivo application as therapeutic agents, we used two different cell lines to investigate their cytotoxic abilities. While we only observed minor cytotoxic effects on CaCo2/TC7 cells at higher peptide concentration (FIG. 22A), HT29 MTX E29 cells were more susceptible to both tested peptide-derivates (FIG. 22B). Importantly, at lower concentrations (e.g. 12.5 µM, where HNP-$4_{1\text{-}11mod}$ has a strong antibacterial effect), the fragments exhibited only modest cytotoxicity. We additionally examined the hemolytic activity of said peptides (FIG. 22C). While HNP-$4_{1\text{-}11mod}$ has a 20% hemolytic effect at 150 µM (by far exceeding the highest concentration needed for bactericidal efficacy) there were negligible toxicity at ≤18.75 µM, i.e. the highest biological relevant concentration. Thus, compared to the honey bee toxin, Melittin, which showed an 80% hemolytic effect at 1.25 µM both HNP-$4_{1\text{-}11}$ and HNP-$4_{1\text{-}11mod}$ appeared with low hemolytic activity. In conclusion, the cytotoxic concentrations identified were magnitudes higher the corresponding bactericidal concentration.

SUMMARY

Within the study and invention as presented above several new findings regarding alpha-defensins and their susceptibility to proteases were made. Indicating from the in silico digest of HD-6, it was rather surprising that HD-6 was unaffected by the naturally occurring proteases in the duodenal fluid. Unlike HD-6, HD-5 was degraded and its fragments surprisingly contained antimicrobial activity against commensal and pathogenic bacteria.

Determination of the antimicrobial spectrum of the HD-5 fragments revealed a high antimicrobial activity against both commensal and pathogenic bacteria. The antimicrobial spectrum was different from the spectrum of the mother peptide as well as different between the HD5 fragments, and these HD-5 fragments thus seem to add additional bacterial killing or microbiota modulation capability. This interesting and surprising phenomenon also contributes to the understanding of how a few intestinal defensins can modulate or support very different commensal colonizations in different parts of the intestine.

Within the present study and the invention, it was shown that $HD5_{1\text{-}9}$, $HD5_{1\text{-}13}$, $HD5_{1\text{-}28}$, $HD5_{7\text{-}32}$, $HD5_{10\text{-}32}$, $HD5_{14\text{-}32}$, $HD5_{10\text{-}27}$ and $HD5_{26\text{-}32}$ possessed microbiota modulating effects. Beside the effects on some low abundant bacterial strains, the present results showed that surprisingly only mice treated orally with $HD5_{1\text{-}9}$ had an increased amount of A. muciniphila compared to non-treated mice, moreover different to other bacteria A. muciniphila was not susceptible to $HD5_{1\text{-}9}$ in a turbidity broth assay, fitting to the findings that Akkermansia sp. was increased in the microbiome analysis. Such a surprising influence on A. muciniphila has not previously been described for the full length in the HD-5 peptide. This underlines the different spectra between the full-length peptides and its fragments.

The present study and the invention emphasize the importance of the cell wall charge for the binding of $HD5_{1\text{-}9}$ to Gram-positive bacteria, whereas the cell wall charge seems of less importance for the binding to Gram-negative bacteria. The conducted experiments further surprisingly demonstrated that dimerized $HD5_{1\text{-}9}$ displayed a much better bactericidal activity against S. aureus species compared to the monomer form of $HD5_{1\text{-}9}$. This implicates a different mode of action for the two forms of $HD5_{1\text{-}9}$. HNP-$4_{1\text{-}11}$ was surprisingly equimolar to HNP-$4_{fl}$, indicating that the antimicrobial efficacy of the natural complex-to-produce HNP- $4_{fl}$ is solely dependent on the first 11 amino acids (HNP-$4_{1-11}$). Surprisingly and pointing further towards enhanced bactericidal efficacy of the linear fragment, HNP-$4_{1-11mod}$, which was expected to exhibit increased stability over the non-modified version, was superior to both HNP-$4_{fl}$ and HNP-$4_{1-11}$ with a MIC several fold lower than the one observed for the natural occurring full length peptide. We have thus unleashed the antimicrobial activity of the full length HNP-4 peptide by tryptic digestion, whereby we have identified a single fragment with a remarkable antimicrobial potential, exceeding that of the full length peptide on molar level. Surprisingly, we observed the antimicrobial efficacy of the peptides to be equally efficient between multi-drug-resistant and non-resistant strains.

Beside their microbiota modulating abilities another important field for antimicrobial active peptides is the rapidly increasing number of antibiotic-resistant bacteria. The antimicrobial spectrum of the peptide fragments identified herein allows to use these peptides as a source of new antibiotics against multi drug resistant bacteria. Also, the discovery of these easy and cheap to produce peptide fragments is a new alternative approach to therapeutically manipulate microbiome composition and treat Paneth cell associated diseases such as Crohn's disease of the small intestine.

REFERENCES

1. Lehrer, R. I. & Lu, W. α-Defensins in human innate immunity. *Immunol. Rev.* 245, 84-112 (2012).
2. Ericksen, B., Wu, Z., Lu, W. & Lehrer, R. I. Antibacterial Activity and Specificity of the Six Human α-Defensins. *Antimicrob. Agents Chemother.* 49, 269-275 (2005).
3. Schroeder, B. O. et al. Reduction of disulphide bonds unmasks potent antimicrobial activity of human β-defensin 1. *Nature* 469, 419-423 (2011).
4. Chu, H. et al. Human α-defensin 6 promotes mucosal innate immunity through self-assembled peptide nanonets. *Science* 337, 477-481 (2012).
5. Schroeder, B. O., Stange, E. F. & Wehkamp, J. Waking the wimp: redox-modulation activates human beta-defensin 1. *Gut Microbes* 2, 262-266 (2011).
6. Wendler, J. et al. Bacterial periplasmic oxido-reductases are essential for the activity of oxidized human antimicrobial β-defensin 1. *Infect. Immun.* IAI.00875-17 (2018) doi: 10.1128/IAI.00875-17.
7. Stawikowski, M. & Fields, G. B. Introduction to peptide synthesis. *Curr Protoc Protein Sci* Chapter 18, Unit 18.1 (2012).
8. Davis, L. *Basic Methods in Molecular Biology*. (Elsevier, 2012).
9. Sambrook, J., Fritsch, E. F. & Maniatis, T. Molecular cloning: a laboratory manual. *Molecular cloning: a laboratory manual*. (1989).
10. Rowe, R. C., Sheskey, P. J., Cook, W. G. & Fenton, M. E. *Handbook of Pharmaceutical Excipients*. (Pharmaceutical Press, 2012).
11. Schroeder, B. O. et al. Reduction of disulphide bonds unmasks potent antimicrobial activity of human β-defensin 1. *Nature* 469, 419-423 (2011).
12. Lehrer, R. I., Rosenman, M., Harwig, S. S., Jackson, R. & Eisenhauer, P. Ultrasensitive assays for endogenous antimicrobial polypeptides. *J. Immunol. Methods* 137, 167-173 (1991).
13. Oddo, A. & Hansen, P. R. Hemolytic Activity of Antimicrobial Peptides. *Methods Mol. Biol.* 1548, 427-435 (2017).
14. Callahan, B. J. et al. DADA2: High-resolution sample inference from Illumina amplicon data. *Nat. Methods* 13, 581-583 (2016).
15. McMurdie, P. J. & Holmes, S. phyloseq: An R Package for Reproducible Interactive Analysis and Graphics of Microbiome Census Data. *PLoS One* 8, (2013).
16. Paulson, J. N., Stine, O. C., Bravo, H. C. & Pop, M. Differential abundance analysis for microbial marker-gene surveys. *Nature Methods* 10, 1200-1202 (2013).
17. Oksanen, J. et al. vegan: *Community Ecology Package*. (2018).
18. ggplot2-Elegant Graphics for Data Analysis (2nd Edition)|Gómez-|Journal of Statistical Software. doi: 10.18637/jss.v077.b02.
19. Baba, T. et al. Construction of *Escherichia coli* K-12 in-frame, single-gene knockout mutants: the Keio collection. *Mol Syst Biol* 2, 2006.0008 (2006).
20. Weidenmaier, C. et al. Lack of wall teichoic acids in *Staphylococcus aureus* leads to reduced interactions with endothelial cells and to attenuated virulence in a rabbit model of endocarditis. *J. Infect. Dis.* 191, 1771-1777 (2005).
21. Peschel, A. & Collins, L. V. Staphylococcal resistance to antimicrobial peptides of mammalian and bacterial origin. *Peptides* 22, 1651-1659 (2001).
22. Wanner, S. et al. Wall teichoic acids mediate increased virulence in *Staphylococcus aureus*. *Nat Microbiol* 2, 16257 (2017).
23. Rajabi, M. et al. The conserved salt bridge in human alpha-defensin 5 is required for its precursor processing and proteolytic stability. *J. Biol. Chem.* 283, 21509-21518 (2008).
24. Rajabi, M. et al. Functional determinants of human enteric α-defensin HD5: crucial role for hydrophobicity at dimer interface. *J. Biol. Chem.* 287, 21615-21627 (2012).
25. Szyk, A. et al. Crystal structures of human alpha-defensins HNP4, HD5, and HD6. *Protein Sci.* 15, 2749-2760 (2006).
26. Wanniarachchi, Y. A., Kaczmarek, P., Wan, A. & Nolan, E. M. Human Defensin 5 Disulfide Array Mutants: Disulfide Bond Deletion Attenuates Antibacterial Activity Against *Staphylococcus aureus*. *Biochemistry* 50, 8005-8017 (2011).
27. Hong, S. Y., Oh, J. E. & Lee, K. H. Effect of D-amino acid substitution on the stability, the secondary structure, and the activity of membrane-active peptide. *Biochem. Pharmacol.* 58, 1775-1780 (1999).
28. Brinckerhoff, L. H. et al. Terminal modifications inhibit proteolytic degradation of an immunogenic MART-1 (27-35) peptide: implications for peptide vaccines. *Int. J. Cancer* 83, 326-334 (1999).

The invention claimed is:

1. A peptide having antimicrobial activity, which peptide is a fragment of human defensin-5 (HD-5) or a fragment of human neutrophil peptide 4 (HNP-4), wherein the peptide consists of the sequence of:

ATCYCRTGR, (SEQ ID No: 1)

RGTRCYCTA, (SEQ ID No: 2)

Ac-atcycrtGr-NH$_2$, (SEQ ID No: 5)

VCSCRLVFCRR, (SEQ ID No: 3)

RRCFVLRCSCV, (SEQ ID No: 4)

Ac-vcscrlvfcrr-NH$_2$ (SEQ ID No: 6)

LYRLCCR, (SEQ ID No: 41)

ATCYCRTGRCATR, (SEQ ID No: 34)

ATCYCRTGRCATRESLSGVCEISGRLYR, (SEQ ID No: 12)

TGRCATRESLSGVCEISGRLYRLCCR, (SEQ ID No: 14)

CATRESLSGVCEISGRLYRLCCR, (SEQ ID No: 19)

ESLSGVCEISGRLYRLCCR, (SEQ ID No: 25)

CATRESLSGVCEISGRLY, (SEQ ID No: 28)

or multimers thereof, or N- or C-terminal non-amino acid modifications thereof.

2. The peptide of claim 1, wherein the peptide consists of the sequence of:

ATCYCRTGR, (SEQ ID No: 1)

RGTRCYCTA, (SEQ ID No: 2)

Ac-atcycrtGr-NH$_2$, (SEQ ID No: 5)

LYRLCCR, (SEQ ID No: 41)

ATCYCRTGRCATR, (SEQ ID No: 34)

ATCYCRTGRCATRESLSGVCEISGRLYR, (SEQ ID No: 12)

or

TGRCATRESLSGVCEISGRLYRLCCR. (SEQ ID No: 14)

3. The peptide of claim 1, wherein the peptide consists of the sequence of:

ATCYCRTGR, (SEQ ID No: 1)

RGTRCYCTA, (SEQ ID No: 2)

Ac-atcycrtGr-NH$_2$, (SEQ ID No: 5)

or

LYRLCCR. (SEQ ID No: 41)

4. The peptide of claim 1, wherein the peptide consists of the sequence of:

ATCYCRTGR, (SEQ ID No: 1)

RGTRCYCTA, (SEQ ID No: 2)

or

Ac-atcycrtGr-NH$_2$. (SEQ ID No: 5)

5. The peptide of claim 1, wherein the peptide consists of the sequence of: ATCYCRTGR (SEQ ID No: 1), or RGTRCYCTA (SEQ ID NO: 2).

6. The peptide of claim 1, wherein the peptide is a homodimer linked through a cysteine-bridge.

7. The peptide of claim 1, further comprising an N-terminal modification selected from the group consisting of: acetyl-, formyl-, pyroglutamyl-, fatty acids-, urea-, carbamate-, and alkylamine.

8. The peptide of claim 1, further comprising a C-terminal modification selected from the group consisting of: -Amide, -Acid, -N-alkyl-Amide, -Aldehyde, -Ester, -p-Nitroanilide, and -7-Amino-4-Methylcoumarin.

9. The peptide of claim 1, wherein the peptide consists of a mixture of D- and L-amino acids.

10. A method of manufacturing the peptide of claim 1, the method comprising subjecting reduced HD-5 or human neutrophil peptide 4 (HNP-4) to protease activity followed by purification.

11. The method of claim 10, wherein the protease is trypsin or chymotrypsin.

12. The method of claim 10, further comprising dimerizing of the peptide through generation of an intramolecular disulfide.

13. The method of claim 10, further comprising modifying the N- or —C terminal of the peptide.

* * * * *

SEQUENCE LISTING

<160> NUMBER OF SEQ ID NOS: 98

<210> SEQ ID NO 1

```
<211> LENGTH: 9
<212> TYPE: PRT
<213> ORGANISM: Artificial sequence
<220> FEATURE:
<223> OTHER INFORMATION: synthesized peptide

<400> SEQUENCE: 1

Ala Thr Cys Tyr Cys Arg Thr Gly Arg
1               5

<210> SEQ ID NO 2
<211> LENGTH: 9
<212> TYPE: PRT
<213> ORGANISM: Artificial sequence
<220> FEATURE:
<223> OTHER INFORMATION: synthesized peptide

<400> SEQUENCE: 2

Arg Gly Thr Arg Cys Tyr Cys Thr Ala
1               5

<210> SEQ ID NO 3
<211> LENGTH: 11
<212> TYPE: PRT
<213> ORGANISM: Artificial sequence
<220> FEATURE:
<223> OTHER INFORMATION: synthesized peptide

<400> SEQUENCE: 3

Val Cys Ser Cys Arg Leu Val Phe Cys Arg Arg
1               5                   10

<210> SEQ ID NO 4
<211> LENGTH: 11
<212> TYPE: PRT
<213> ORGANISM: Artificial sequence
<220> FEATURE:
<223> OTHER INFORMATION: synthesized peptide

<400> SEQUENCE: 4

Arg Arg Cys Phe Val Leu Arg Cys Ser Cys Val
1               5                   10

<210> SEQ ID NO 5
<211> LENGTH: 9
<212> TYPE: PRT
<213> ORGANISM: Artificial sequence
<220> FEATURE:
<223> OTHER INFORMATION: synthesized peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(7)
<223> OTHER INFORMATION: D-amino acid
<220> FEATURE:
<221> NAME/KEY: MOD_RES
<222> LOCATION: (9)..(9)
<223> OTHER INFORMATION: AMIDATION
<220> FEATURE:
<221> NAME/KEY: MISC_FEATURE
<222> LOCATION: (9)..(9)
<223> OTHER INFORMATION: D-amino acid

<400> SEQUENCE: 5

Ala Thr Cys Tyr Cys Arg Thr Gly Arg
1               5
```

```
<210> SEQ ID NO 6
<211> LENGTH: 11
<212> TYPE: PRT
<213> ORGANISM: Artificial sequence
<220> FEATURE:
<223> OTHER INFORMATION: synthesized peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(11)
<223> OTHER INFORMATION: D-amino acid
<220> FEATURE:
<221> NAME/KEY: MOD_RES
<222> LOCATION: (11)..(11)
<223> OTHER INFORMATION: AMIDATION

<400> SEQUENCE: 6

Val Cys Ser Cys Arg Leu Val Phe Cys Arg Arg
1               5                   10

<210> SEQ ID NO 7
<211> LENGTH: 19
<212> TYPE: DNA
<213> ORGANISM: Artificial sequence
<220> FEATURE:
<223> OTHER INFORMATION: primer

<400> SEQUENCE: 7
gtgccagcmg ccgcggtaa                                             19

<210> SEQ ID NO 8
<211> LENGTH: 20
<212> TYPE: DNA
<213> ORGANISM: Artificial sequence
<220> FEATURE:
<223> OTHER INFORMATION: primer

<400> SEQUENCE: 8
ggactachvg ggtwtctaat                                            20

<210> SEQ ID NO 9
<211> LENGTH: 32
<212> TYPE: PRT
<213> ORGANISM: Homo sapiens

<400> SEQUENCE: 9

Ala Thr Cys Tyr Cys Arg Thr Gly Arg Cys Ala Thr Arg Glu Ser Leu
1               5                   10                  15

Ser Gly Val Cys Glu Ile Ser Gly Arg Leu Tyr Arg Leu Cys Cys Arg
            20                  25                  30

<210> SEQ ID NO 10
<211> LENGTH: 29
<212> TYPE: PRT
<213> ORGANISM: Homo sapiens

<400> SEQUENCE: 10

Ala Thr Cys Tyr Cys Arg Thr Gly Arg Cys Ala Thr Arg Glu Ser Leu
1               5                   10                  15

Ser Gly Val Cys Glu Ile Ser Gly Arg Leu Tyr Arg Leu
            20                  25

<210> SEQ ID NO 11
```

<211> LENGTH: 28
<212> TYPE: PRT
<213> ORGANISM: Homo sapiens

<400> SEQUENCE: 11

Cys Arg Thr Gly Arg Cys Ala Thr Arg Glu Ser Leu Ser Gly Val Cys
1               5                   10                  15

Glu Ile Ser Gly Arg Leu Tyr Arg Leu Cys Cys Arg
            20                  25

<210> SEQ ID NO 12
<211> LENGTH: 28
<212> TYPE: PRT
<213> ORGANISM: Homo sapiens

<400> SEQUENCE: 12

Ala Thr Cys Tyr Cys Arg Thr Gly Arg Cys Ala Thr Arg Glu Ser Leu
1               5                   10                  15

Ser Gly Val Cys Glu Ile Ser Gly Arg Leu Tyr Arg
            20                  25

<210> SEQ ID NO 13
<211> LENGTH: 27
<212> TYPE: PRT
<213> ORGANISM: Homo sapiens

<400> SEQUENCE: 13

Ala Thr Cys Tyr Cys Arg Thr Gly Arg Cys Ala Thr Arg Glu Ser Leu
1               5                   10                  15

Ser Gly Val Cys Glu Ile Ser Gly Arg Leu Tyr
            20                  25

<210> SEQ ID NO 14
<211> LENGTH: 26
<212> TYPE: PRT
<213> ORGANISM: Homo sapiens

<400> SEQUENCE: 14

Thr Gly Arg Cys Ala Thr Arg Glu Ser Leu Ser Gly Val Cys Glu Ile
1               5                   10                  15

Ser Gly Arg Leu Tyr Arg Leu Cys Cys Arg
            20                  25

<210> SEQ ID NO 15
<211> LENGTH: 26
<212> TYPE: PRT
<213> ORGANISM: Homo sapiens

<400> SEQUENCE: 15

Ala Thr Cys Tyr Cys Arg Thr Gly Arg Cys Ala Thr Arg Glu Ser Leu
1               5                   10                  15

Ser Gly Val Cys Glu Ile Ser Gly Arg Leu
            20                  25

<210> SEQ ID NO 16
<211> LENGTH: 25
<212> TYPE: PRT
<213> ORGANISM: Homo sapiens

<400> SEQUENCE: 16

Cys Arg Thr Gly Arg Cys Ala Thr Arg Glu Ser Leu Ser Gly Val Cys
1               5                   10                  15

```
Glu Ile Ser Gly Arg Leu Tyr Arg Leu
        20                  25

<210> SEQ ID NO 17
<211> LENGTH: 25
<212> TYPE: PRT
<213> ORGANISM: Homo sapiens

<400> SEQUENCE: 17

Ala Thr Cys Tyr Cys Arg Thr Gly Arg Cys Ala Thr Arg Glu Ser Leu
1               5                   10                  15

Ser Gly Val Cys Glu Ile Ser Gly Arg
            20                  25

<210> SEQ ID NO 18
<211> LENGTH: 24
<212> TYPE: PRT
<213> ORGANISM: Homo sapiens

<400> SEQUENCE: 18

Cys Arg Thr Gly Arg Cys Ala Thr Arg Glu Ser Leu Ser Gly Val Cys
1               5                   10                  15

Glu Ile Ser Gly Arg Leu Tyr Arg
            20

<210> SEQ ID NO 19
<211> LENGTH: 23
<212> TYPE: PRT
<213> ORGANISM: Homo sapiens

<400> SEQUENCE: 19

Cys Ala Thr Arg Glu Ser Leu Ser Gly Val Cys Glu Ile Ser Gly Arg
1               5                   10                  15

Leu Tyr Arg Leu Cys Cys Arg
            20

<210> SEQ ID NO 20
<211> LENGTH: 23
<212> TYPE: PRT
<213> ORGANISM: Homo sapiens

<400> SEQUENCE: 20

Cys Arg Thr Gly Arg Cys Ala Thr Arg Glu Ser Leu Ser Gly Val Cys
1               5                   10                  15

Glu Ile Ser Gly Arg Leu Tyr
            20

<210> SEQ ID NO 21
<211> LENGTH: 22
<212> TYPE: PRT
<213> ORGANISM: Homo sapiens

<400> SEQUENCE: 21

Thr Gly Arg Cys Ala Thr Arg Glu Ser Leu Ser Gly Val Cys Glu Ile
1               5                   10                  15

Ser Gly Arg Leu Tyr Arg
            20

<210> SEQ ID NO 22
<211> LENGTH: 22
<212> TYPE: PRT
<213> ORGANISM: Homo sapiens
```

```
<400> SEQUENCE: 22

Cys Arg Thr Gly Arg Cys Ala Thr Arg Glu Ser Leu Ser Gly Val Cys
1               5                   10                  15

Glu Ile Ser Gly Arg Leu
            20

<210> SEQ ID NO 23
<211> LENGTH: 21
<212> TYPE: PRT
<213> ORGANISM: Homo sapiens

<400> SEQUENCE: 23

Thr Gly Arg Cys Ala Thr Arg Glu Ser Leu Ser Gly Val Cys Glu Ile
1               5                   10                  15

Ser Gly Arg Leu Tyr
            20

<210> SEQ ID NO 24
<211> LENGTH: 21
<212> TYPE: PRT
<213> ORGANISM: Homo sapiens

<400> SEQUENCE: 24

Cys Arg Thr Gly Arg Cys Ala Thr Arg Glu Ser Leu Ser Gly Val Cys
1               5                   10                  15

Glu Ile Ser Gly Arg
            20

<210> SEQ ID NO 25
<211> LENGTH: 19
<212> TYPE: PRT
<213> ORGANISM: Homo sapiens

<400> SEQUENCE: 25

Glu Ser Leu Ser Gly Val Cys Glu Ile Ser Gly Arg Leu Tyr Arg Leu
1               5                   10                  15

Cys Cys Arg

<210> SEQ ID NO 26
<211> LENGTH: 19
<212> TYPE: PRT
<213> ORGANISM: Homo sapiens

<400> SEQUENCE: 26

Cys Ala Thr Arg Glu Ser Leu Ser Gly Val Cys Glu Ile Ser Gly Arg
1               5                   10                  15

Leu Tyr Arg

<210> SEQ ID NO 27
<211> LENGTH: 19
<212> TYPE: PRT
<213> ORGANISM: Homo sapiens

<400> SEQUENCE: 27

Thr Gly Arg Cys Ala Thr Arg Glu Ser Leu Ser Gly Val Cys Glu Ile
1               5                   10                  15

Ser Gly Arg

<210> SEQ ID NO 28
<211> LENGTH: 18
<212> TYPE: PRT
```

```
<213> ORGANISM: Homo sapiens

<400> SEQUENCE: 28

Cys Ala Thr Arg Glu Ser Leu Ser Gly Val Cys Glu Ile Ser Gly Arg
1               5                   10                  15

Leu Tyr

<210> SEQ ID NO 29
<211> LENGTH: 16
<212> TYPE: PRT
<213> ORGANISM: Homo sapiens

<400> SEQUENCE: 29

Ser Gly Val Cys Glu Ile Ser Gly Arg Leu Tyr Arg Leu Cys Cys Arg
1               5                   10                  15

<210> SEQ ID NO 30
<211> LENGTH: 16
<212> TYPE: PRT
<213> ORGANISM: Homo sapiens

<400> SEQUENCE: 30

Ala Thr Cys Tyr Cys Arg Thr Gly Arg Cys Ala Thr Arg Glu Ser Leu
1               5                   10                  15

<210> SEQ ID NO 31
<211> LENGTH: 15
<212> TYPE: PRT
<213> ORGANISM: Homo sapiens

<400> SEQUENCE: 31

Glu Ser Leu Ser Gly Val Cys Glu Ile Ser Gly Arg Leu Tyr Arg
1               5                   10                  15

<210> SEQ ID NO 32
<211> LENGTH: 16
<212> TYPE: PRT
<213> ORGANISM: Homo sapiens

<400> SEQUENCE: 32

Cys Ala Thr Arg Glu Ser Leu Ser Gly Val Cys Glu Ile Ser Gly Arg
1               5                   10                  15

<210> SEQ ID NO 33
<211> LENGTH: 14
<212> TYPE: PRT
<213> ORGANISM: Homo sapiens

<400> SEQUENCE: 33

Glu Ser Leu Ser Gly Val Cys Glu Ile Ser Gly Arg Leu Tyr
1               5                   10

<210> SEQ ID NO 34
<211> LENGTH: 13
<212> TYPE: PRT
<213> ORGANISM: Homo sapiens

<400> SEQUENCE: 34

Ala Thr Cys Tyr Cys Arg Thr Gly Arg Cys Ala Thr Arg
1               5                   10

<210> SEQ ID NO 35
<211> LENGTH: 13
<212> TYPE: PRT
```

<213> ORGANISM: Homo sapiens

<400> SEQUENCE: 35

Ser Gly Val Cys Glu Ile Ser Gly Arg Leu Tyr Arg Leu
1               5                   10

<210> SEQ ID NO 36
<211> LENGTH: 12
<212> TYPE: PRT
<213> ORGANISM: Homo sapiens

<400> SEQUENCE: 36

Cys Arg Thr Gly Arg Cys Ala Thr Arg Glu Ser Leu
1               5                   10

<210> SEQ ID NO 37
<211> LENGTH: 12
<212> TYPE: PRT
<213> ORGANISM: Homo sapiens

<400> SEQUENCE: 37

Glu Ser Leu Ser Gly Val Cys Glu Ile Ser Gly Arg
1               5                   10

<210> SEQ ID NO 38
<211> LENGTH: 11
<212> TYPE: PRT
<213> ORGANISM: Homo sapiens

<400> SEQUENCE: 38

Ser Gly Val Cys Glu Ile Ser Gly Arg Leu Tyr
1               5                   10

<210> SEQ ID NO 39
<211> LENGTH: 9
<212> TYPE: PRT
<213> ORGANISM: Homo sapiens

<400> SEQUENCE: 39

Cys Arg Thr Gly Arg Cys Ala Thr Arg
1               5

<210> SEQ ID NO 40
<211> LENGTH: 10
<212> TYPE: PRT
<213> ORGANISM: Homo sapiens

<400> SEQUENCE: 40

Ser Gly Val Cys Glu Ile Ser Gly Arg Leu
1               5                   10

<210> SEQ ID NO 41
<211> LENGTH: 7
<212> TYPE: PRT
<213> ORGANISM: Homo sapiens

<400> SEQUENCE: 41

Leu Tyr Arg Leu Cys Cys Arg
1               5

<210> SEQ ID NO 42
<211> LENGTH: 6
<212> TYPE: PRT
<213> ORGANISM: Homo sapiens

```
<400> SEQUENCE: 42

Tyr Arg Leu Cys Cys Arg
1               5

<210> SEQ ID NO 43
<211> LENGTH: 7
<212> TYPE: PRT
<213> ORGANISM: Homo sapiens

<400> SEQUENCE: 43

Thr Gly Arg Cys Ala Thr Arg
1               5

<210> SEQ ID NO 44
<211> LENGTH: 6
<212> TYPE: PRT
<213> ORGANISM: Homo sapiens

<400> SEQUENCE: 44

Ala Thr Cys Tyr Cys Arg
1               5

<210> SEQ ID NO 45
<211> LENGTH: 5
<212> TYPE: PRT
<213> ORGANISM: Homo sapiens

<400> SEQUENCE: 45

Arg Leu Cys Cys Arg
1               5

<210> SEQ ID NO 46
<211> LENGTH: 5
<212> TYPE: PRT
<213> ORGANISM: Homo sapiens

<400> SEQUENCE: 46

Cys Arg Thr Gly Arg
1               5

<210> SEQ ID NO 47
<211> LENGTH: 32
<212> TYPE: PRT
<213> ORGANISM: Homo sapiens

<400> SEQUENCE: 47

Ala Phe Thr Cys His Cys Arg Arg Ser Cys Tyr Ser Thr Glu Tyr Ser
1               5                   10                  15

Tyr Gly Thr Cys Thr Val Met Gly Ile Asn His Arg Phe Cys Cys Leu
            20                  25                  30

<210> SEQ ID NO 48
<211> LENGTH: 30
<212> TYPE: PRT
<213> ORGANISM: Homo sapiens

<400> SEQUENCE: 48

Thr Cys His Cys Arg Arg Ser Cys Tyr Ser Thr Glu Tyr Ser Tyr Gly
1               5                   10                  15

Thr Cys Thr Val Met Gly Ile Asn His Arg Phe Cys Cys Leu
            20                  25                  30

<210> SEQ ID NO 49
```

<211> LENGTH: 29
<212> TYPE: PRT
<213> ORGANISM: Homo sapiens

<400> SEQUENCE: 49

Ala Phe Thr Cys His Cys Arg Arg Ser Cys Tyr Ser Thr Glu Tyr Ser
1               5                   10                  15

Tyr Gly Thr Cys Thr Val Met Gly Ile Asn His Arg Phe
            20                  25

<210> SEQ ID NO 50
<211> LENGTH: 28
<212> TYPE: PRT
<213> ORGANISM: Homo sapiens

<400> SEQUENCE: 50

Ala Phe Thr Cys His Cys Arg Arg Ser Cys Tyr Ser Thr Glu Tyr Ser
1               5                   10                  15

Tyr Gly Thr Cys Thr Val Met Gly Ile Asn His Arg
            20                  25

<210> SEQ ID NO 51
<211> LENGTH: 27
<212> TYPE: PRT
<213> ORGANISM: Homo sapiens

<400> SEQUENCE: 51

Thr Cys His Cys Arg Arg Ser Cys Tyr Ser Thr Glu Tyr Ser Tyr Gly
1               5                   10                  15

Thr Cys Thr Val Met Gly Ile Asn His Arg Phe
            20                  25

<210> SEQ ID NO 52
<211> LENGTH: 26
<212> TYPE: PRT
<213> ORGANISM: Homo sapiens

<400> SEQUENCE: 52

Thr Cys His Cys Arg Arg Ser Cys Tyr Ser Thr Glu Tyr Ser Tyr Gly
1               5                   10                  15

Thr Cys Thr Val Met Gly Ile Asn His Arg
            20                  25

<210> SEQ ID NO 53
<211> LENGTH: 25
<212> TYPE: PRT
<213> ORGANISM: Homo sapiens

<400> SEQUENCE: 53

Arg Ser Cys Tyr Ser Thr Glu Tyr Ser Tyr Gly Thr Cys Thr Val Met
1               5                   10                  15

Gly Ile Asn His Arg Phe Cys Cys Leu
            20                  25

<210> SEQ ID NO 54
<211> LENGTH: 24
<212> TYPE: PRT
<213> ORGANISM: Homo sapiens

<400> SEQUENCE: 54

Ser Cys Tyr Ser Thr Glu Tyr Ser Tyr Gly Thr Cys Thr Val Met Gly
1               5                   10                  15

Ile Asn His Arg Phe Cys Cys Leu
            20

<210> SEQ ID NO 55
<211> LENGTH: 23
<212> TYPE: PRT
<213> ORGANISM: Homo sapiens

<400> SEQUENCE: 55

Ala Phe Thr Cys His Cys Arg Arg Ser Cys Tyr Ser Thr Glu Tyr Ser
1               5                   10                  15

Tyr Gly Thr Cys Thr Val Met
            20

<210> SEQ ID NO 56
<211> LENGTH: 22
<212> TYPE: PRT
<213> ORGANISM: Homo sapiens

<400> SEQUENCE: 56

Arg Ser Cys Tyr Ser Thr Glu Tyr Ser Tyr Gly Thr Cys Thr Val Met
1               5                   10                  15

Gly Ile Asn His Arg Phe
            20

<210> SEQ ID NO 57
<211> LENGTH: 21
<212> TYPE: PRT
<213> ORGANISM: Homo sapiens

<400> SEQUENCE: 57

Thr Cys His Cys Arg Arg Ser Cys Tyr Ser Thr Glu Tyr Ser Tyr Gly
1               5                   10                  15

Thr Cys Thr Val Met
            20

<210> SEQ ID NO 58
<211> LENGTH: 21
<212> TYPE: PRT
<213> ORGANISM: Homo sapiens

<400> SEQUENCE: 58

Arg Ser Cys Tyr Ser Thr Glu Tyr Ser Tyr Gly Thr Cys Thr Val Met
1               5                   10                  15

Gly Ile Asn His Arg
            20

<210> SEQ ID NO 59
<211> LENGTH: 21
<212> TYPE: PRT
<213> ORGANISM: Homo sapiens

<400> SEQUENCE: 59

Ser Cys Tyr Ser Thr Glu Tyr Ser Tyr Gly Thr Cys Thr Val Met Gly
1               5                   10                  15

Ile Asn His Arg Phe
            20

<210> SEQ ID NO 60
<211> LENGTH: 21
<212> TYPE: PRT
<213> ORGANISM: Homo sapiens

```
<400> SEQUENCE: 60

Ser Thr Glu Tyr Ser Tyr Gly Thr Cys Thr Val Met Gly Ile Asn His
1               5                   10                  15

Arg Phe Cys Cys Leu
            20

<210> SEQ ID NO 61
<211> LENGTH: 20
<212> TYPE: PRT
<213> ORGANISM: Homo sapiens

<400> SEQUENCE: 61

Ser Cys Tyr Ser Thr Glu Tyr Ser Tyr Gly Thr Cys Thr Val Met Gly
1               5                   10                  15

Ile Asn His Arg
            20

<210> SEQ ID NO 62
<211> LENGTH: 17
<212> TYPE: PRT
<213> ORGANISM: Homo sapiens

<400> SEQUENCE: 62

Ala Phe Thr Cys His Cys Arg Arg Ser Cys Tyr Ser Thr Glu Tyr Ser
1               5                   10                  15

Tyr

<210> SEQ ID NO 63
<211> LENGTH: 18
<212> TYPE: PRT
<213> ORGANISM: Homo sapiens

<400> SEQUENCE: 63

Ser Thr Glu Tyr Ser Tyr Gly Thr Cys Thr Val Met Gly Ile Asn His
1               5                   10                  15

Arg Phe

<210> SEQ ID NO 64
<211> LENGTH: 17
<212> TYPE: PRT
<213> ORGANISM: Homo sapiens

<400> SEQUENCE: 64

Ser Thr Glu Tyr Ser Tyr Gly Thr Cys Thr Val Met Gly Ile Asn His
1               5                   10                  15

Arg

<210> SEQ ID NO 65
<211> LENGTH: 17
<212> TYPE: PRT
<213> ORGANISM: Homo sapiens

<400> SEQUENCE: 65

Ser Tyr Gly Thr Cys Thr Val Met Gly Ile Asn His Arg Phe Cys Cys
1               5                   10                  15

Leu

<210> SEQ ID NO 66
<211> LENGTH: 15
<212> TYPE: PRT
<213> ORGANISM: Homo sapiens
```

<400> SEQUENCE: 66

Thr Cys His Cys Arg Arg Ser Cys Tyr Ser Thr Glu Tyr Ser Tyr
1               5                   10                  15

<210> SEQ ID NO 67
<211> LENGTH: 15
<212> TYPE: PRT
<213> ORGANISM: Homo sapiens

<400> SEQUENCE: 67

Ala Phe Thr Cys His Cys Arg Arg Ser Cys Tyr Ser Thr Glu Tyr
1               5                   10                  15

<210> SEQ ID NO 68
<211> LENGTH: 15
<212> TYPE: PRT
<213> ORGANISM: Homo sapiens

<400> SEQUENCE: 68

Gly Thr Cys Thr Val Met Gly Ile Asn His Arg Phe Cys Cys Leu
1               5                   10                  15

<210> SEQ ID NO 69
<211> LENGTH: 13
<212> TYPE: PRT
<213> ORGANISM: Homo sapiens

<400> SEQUENCE: 69

Thr Cys His Cys Arg Arg Ser Cys Tyr Ser Thr Glu Tyr
1               5                   10

<210> SEQ ID NO 70
<211> LENGTH: 14
<212> TYPE: PRT
<213> ORGANISM: Homo sapiens

<400> SEQUENCE: 70

Ser Tyr Gly Thr Cys Thr Val Met Gly Ile Asn His Arg Phe
1               5                   10

<210> SEQ ID NO 71
<211> LENGTH: 13
<212> TYPE: PRT
<213> ORGANISM: Homo sapiens

<400> SEQUENCE: 71

Ser Tyr Gly Thr Cys Thr Val Met Gly Ile Asn His Arg
1               5                   10

<210> SEQ ID NO 72
<211> LENGTH: 11
<212> TYPE: PRT
<213> ORGANISM: Homo sapiens

<400> SEQUENCE: 72

Ala Phe Thr Cys His Cys Arg Arg Ser Cys Tyr
1               5                   10

<210> SEQ ID NO 73
<211> LENGTH: 12
<212> TYPE: PRT
<213> ORGANISM: Homo sapiens

<400> SEQUENCE: 73

Ser Thr Glu Tyr Ser Tyr Gly Thr Cys Thr Val Met
1               5                   10

<210> SEQ ID NO 74
<211> LENGTH: 12
<212> TYPE: PRT
<213> ORGANISM: Homo sapiens

<400> SEQUENCE: 74

Gly Thr Cys Thr Val Met Gly Ile Asn His Arg Phe
1               5                   10

<210> SEQ ID NO 75
<211> LENGTH: 10
<212> TYPE: PRT
<213> ORGANISM: Homo sapiens

<400> SEQUENCE: 75

Arg Ser Cys Tyr Ser Thr Glu Tyr Ser Tyr
1               5                   10

<210> SEQ ID NO 76
<211> LENGTH: 11
<212> TYPE: PRT
<213> ORGANISM: Homo sapiens

<400> SEQUENCE: 76

Gly Thr Cys Thr Val Met Gly Ile Asn His Arg
1               5                   10

<210> SEQ ID NO 77
<211> LENGTH: 9
<212> TYPE: PRT
<213> ORGANISM: Homo sapiens

<400> SEQUENCE: 77

Thr Cys His Cys Arg Arg Ser Cys Tyr
1               5

<210> SEQ ID NO 78
<211> LENGTH: 9
<212> TYPE: PRT
<213> ORGANISM: Homo sapiens

<400> SEQUENCE: 78

Ser Cys Tyr Ser Thr Glu Tyr Ser Tyr
1               5

<210> SEQ ID NO 79
<211> LENGTH: 9
<212> TYPE: PRT
<213> ORGANISM: Homo sapiens

<400> SEQUENCE: 79

Gly Ile Asn His Arg Phe Cys Cys Leu
1               5

<210> SEQ ID NO 80
<211> LENGTH: 8
<212> TYPE: PRT
<213> ORGANISM: Homo sapiens

<400> SEQUENCE: 80

Arg Ser Cys Tyr Ser Thr Glu Tyr

```
<210> SEQ ID NO 81
<211> LENGTH: 8
<212> TYPE: PRT
<213> ORGANISM: Homo sapiens

<400> SEQUENCE: 81

Ala Phe Thr Cys His Cys Arg Arg
1               5

<210> SEQ ID NO 82
<211> LENGTH: 8
<212> TYPE: PRT
<213> ORGANISM: Homo sapiens

<400> SEQUENCE: 82

Ser Tyr Gly Thr Cys Thr Val Met
1               5

<210> SEQ ID NO 83
<211> LENGTH: 7
<212> TYPE: PRT
<213> ORGANISM: Homo sapiens

<400> SEQUENCE: 83

Ser Cys Tyr Ser Thr Glu Tyr
1               5

<210> SEQ ID NO 84
<211> LENGTH: 7
<212> TYPE: PRT
<213> ORGANISM: Homo sapiens

<400> SEQUENCE: 84

Ala Phe Thr Cys His Cys Arg
1               5

<210> SEQ ID NO 85
<211> LENGTH: 6
<212> TYPE: PRT
<213> ORGANISM: Homo sapiens

<400> SEQUENCE: 85

Thr Cys His Cys Arg Arg
1               5

<210> SEQ ID NO 86
<211> LENGTH: 6
<212> TYPE: PRT
<213> ORGANISM: Homom sapiens

<400> SEQUENCE: 86

Ser Thr Glu Tyr Ser Tyr
1               5

<210> SEQ ID NO 87
<211> LENGTH: 6
<212> TYPE: PRT
<213> ORGANISM: Homo sapiens

<400> SEQUENCE: 87

Gly Ile Asn His Arg Phe
1               5
```

```
<210> SEQ ID NO 88
<211> LENGTH: 5
<212> TYPE: PRT
<213> ORGANISM: Homo sapiens

<400> SEQUENCE: 88

Thr Cys His Cys Arg
1               5

<210> SEQ ID NO 89
<211> LENGTH: 6
<212> TYPE: PRT
<213> ORGANISM: Homo sapiens

<400> SEQUENCE: 89

Gly Thr Cys Thr Val Met
1               5

<210> SEQ ID NO 90
<211> LENGTH: 4
<212> TYPE: PRT
<213> ORGANISM: Homo sapiens

<400> SEQUENCE: 90

Arg Ser Cys Tyr
1

<210> SEQ ID NO 91
<211> LENGTH: 9
<212> TYPE: PRT
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (3)..(3)
<223> OTHER INFORMATION: X is (2S)-2-aminobutanoic acid (Abu)

<400> SEQUENCE: 91

Ala Thr Xaa Tyr Cys Arg Thr Gly Arg
1               5

<210> SEQ ID NO 92
<211> LENGTH: 9
<212> TYPE: PRT
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (5)..(5)
<223> OTHER INFORMATION: X is (2S)-2-aminobutanoic acid (Abu)

<400> SEQUENCE: 92

Ala Thr Cys Tyr Xaa Arg Thr Gly Arg
1               5

<210> SEQ ID NO 93
<211> LENGTH: 9
<212> TYPE: PRT
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (3)..(3)
<223> OTHER INFORMATION: X is (2S)-2-aminobutanoic acid (Abu)
<220> FEATURE:
```

```
<221> NAME/KEY: MISC_FEATURE
<222> LOCATION: (5)..(5)
<223> OTHER INFORMATION: X is (2S)-2-aminobutanoic acid (Abu)

<400> SEQUENCE: 93

Ala Thr Xaa Tyr Xaa Arg Thr Gly Arg
1               5

<210> SEQ ID NO 94
<211> LENGTH: 9
<212> TYPE: PRT
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (6)..(6)
<223> OTHER INFORMATION: X is citrullin (Cit)

<400> SEQUENCE: 94

Ala Thr Cys Tyr Cys Xaa Thr Gly Arg
1               5

<210> SEQ ID NO 95
<211> LENGTH: 9
<212> TYPE: PRT
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (9)..(9)
<223> OTHER INFORMATION: X is citrullin (Cit)

<400> SEQUENCE: 95

Ala Thr Cys Tyr Cys Arg Thr Gly Xaa
1               5

<210> SEQ ID NO 96
<211> LENGTH: 9
<212> TYPE: PRT
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (6)..(6)
<223> OTHER INFORMATION: X is citrullin (Cit)
<220> FEATURE:
<221> NAME/KEY: MISC_FEATURE
<222> LOCATION: (9)..(9)
<223> OTHER INFORMATION: X is citrullin (Cit)

<400> SEQUENCE: 96

Ala Thr Cys Tyr Cys Xaa Thr Gly Xaa
1               5

<210> SEQ ID NO 97
<211> LENGTH: 9
<212> TYPE: PRT
<213> ORGANISM: Artificial Sequence
<220> FEATURE:
<223> OTHER INFORMATION: Synthesized peptide

<400> SEQUENCE: 97

Arg Gly Thr Arg Cys Tyr Cys Thr Ala
1               5

<210> SEQ ID NO 98
```

```
<211> LENGTH: 9
<212> TYPE: PRT
<213> ORGANISM: Artificial Sequence
<220> FEATURE:
<223> OTHER INFORMATION: Synthesized peptide

<400> SEQUENCE: 98

Cys Thr Arg Ala Thr Tyr Cys Arg Gly
1               5
```